(12) United States Patent
Komistek

(10) Patent No.: US 10,064,729 B2
(45) Date of Patent: Sep. 4, 2018

(54) METHODS FOR MAINTAINING PROPER MECHANICS THA

(71) Applicant: DePuy Ireland Unlimited Company, Cork (IE)

(72) Inventor: Richard D. Komistek, Knoxville, TN (US)

(73) Assignee: Depuy Ireland Unlimited Company, Cork (IE)

( * ) Notice: Subject to any disclaimer, the term of this patent is extended or adjusted under 35 U.S.C. 154(b) by 0 days.

(21) Appl. No.: 15/292,825

(22) Filed: Oct. 13, 2016

(65) Prior Publication Data

US 2017/0027704 A1    Feb. 2, 2017

Related U.S. Application Data

(60) Division of application No. 14/700,988, filed on Apr. 30, 2015, which is a continuation of application No.
(Continued)

(51) Int. Cl.
*A61F 2/34* (2006.01)
*A61F 2/32* (2006.01)
(Continued)

(52) U.S. Cl.
CPC .................. *A61F 2/34* (2013.01); *A61F 2/32* (2013.01); *A61F 2/36* (2013.01); *A61F 2/3603* (2013.01); *A61F 2/3609* (2013.01); *A61F 2/4609* (2013.01); *A61F 2002/30079* (2013.01); *A61F 2002/30365* (2013.01); *A61F 2002/30367* (2013.01); *A61F 2002/30378* (2013.01); *A61F 2002/30383* (2013.01); *A61F 2002/30563* (2013.01); *A61F 2002/30578* (2013.01);
(Continued)

(58) Field of Classification Search
CPC .. A61F 2/32; A61F 2/34; A61F 2/4081; A61F 2002/30654; A61F 2002/3409; A61F 2002/30365; A61F 2002/30367
See application file for complete search history.

(56) References Cited

U.S. PATENT DOCUMENTS 3,510,883 A    5/1970  Cathcart
3,656,184 A    4/1972  Chambers
(Continued)

FOREIGN PATENT DOCUMENTS

DE    2139878 A1    2/1973
DE    3643815       6/1988
(Continued)

OTHER PUBLICATIONS

International Search Report, International Application No. PCT/US2013/40107, dated Jun. 12, 2013, 11 pages.
(Continued)

*Primary Examiner* — Alvin Stewart
(74) *Attorney, Agent, or Firm* — Barnes & Thornburg LLP

(57) ABSTRACT

A method of assembling a mobile bearing acetabular component of a prosthetic hip joint is disclosed. The method includes mounting an acetabular cup insert to an acetabular cup. The method includes concurrently repositioning the acetabular cup insert deeper into an interior of the acetabular cup and repositioning the acetabular cup insert outside of an outline of the acetabular cup.

7 Claims, 42 Drawing Sheets

Related U.S. Application Data

13/034,226, filed on Feb. 24, 2011, now Pat. No. 9,023,112.

(51) Int. Cl.
*A61F 2/36* (2006.01)
*A61F 2/30* (2006.01)
*A61F 2/46* (2006.01)

(52) U.S. Cl.
CPC ........... *A61F 2002/30662* (2013.01); *A61F 2002/30688* (2013.01); *A61F 2002/30695* (2013.01); *A61F 2002/30919* (2013.01); *A61F 2002/30948* (2013.01); *A61F 2002/3208* (2013.01); *A61F 2002/3233* (2013.01); *A61F 2002/3422* (2013.01); *A61F 2002/3448* (2013.01); *A61F 2002/3496* (2013.01); *A61F 2002/368* (2013.01); *A61F 2002/3621* (2013.01); *A61F 2002/3623* (2013.01); *A61F 2002/3647* (2013.01); *A61F 2002/4677* (2013.01); *A61F 2210/009* (2013.01); *Y10T 29/49* (2015.01)

(56) References Cited

U.S. PATENT DOCUMENTS

| | | |
|---|---|---|
| 3,891,997 A | 7/1975 | Herbert |
| 3,903,549 A * | 9/1975 | Deyerle ............... A61F 2/34 606/309 |
| 3,925,824 A | 12/1975 | Freeman et al. |
| 4,024,588 A | 5/1977 | Janssen et al. |
| 4,032,994 A | 7/1977 | Frey |
| 4,068,324 A | 1/1978 | Townley et al. |
| 4,318,191 A | 3/1982 | Tepic |
| 4,532,660 A | 8/1985 | Field |
| 4,795,469 A | 1/1989 | Oh |
| 4,795,470 A | 1/1989 | Goymann et al. |
| 4,878,916 A | 11/1989 | Rhenter et al. |
| 4,911,723 A | 3/1990 | Menschik |
| 4,955,919 A | 9/1990 | Pappas et al. |
| 4,960,427 A * | 10/1990 | Noiles ............... A61F 2/32 623/22.18 |
| 5,009,665 A | 4/1991 | Serbousek et al. |
| 5,047,062 A | 9/1991 | Pappas et al. |
| 5,326,368 A | 7/1994 | Collazo |
| 5,370,703 A | 12/1994 | Willert et al. |
| 5,431,657 A | 7/1995 | Rohr |
| 5,549,698 A | 8/1996 | Averill et al. |
| 5,553,476 A | 9/1996 | Oehy et al. |
| 5,593,447 A | 1/1997 | Angell |
| 5,676,704 A | 10/1997 | Ries et al. |
| 5,702,474 A | 12/1997 | McCandliss |
| 5,824,108 A * | 10/1998 | Huebner ............... A61F 2/32 623/22.29 |
| 5,879,401 A | 3/1999 | Besemer et al. |
| 5,879,405 A | 3/1999 | Ries et al. |
| 5,951,605 A | 9/1999 | Dennis et al. |
| 6,002,859 A | 12/1999 | DiGioia et al. |
| 6,066,176 A | 5/2000 | Oshida |
| 6,093,208 A | 7/2000 | Tian |
| 6,120,545 A | 9/2000 | Hamelijnck et al. |
| 6,126,695 A | 10/2000 | Semlitsch |
| 6,152,961 A | 11/2000 | Ostiguy et al. |
| 6,200,350 B1 | 3/2001 | Masini |
| 6,206,929 B1 | 3/2001 | Ochoa et al. |
| 6,224,633 B1 | 5/2001 | Kalberer et al. |
| 6,248,132 B1 | 6/2001 | Harris |
| 6,258,097 B1 | 7/2001 | Cook et al. |
| 6,447,550 B1 | 9/2002 | Hunter et al. |
| 6,488,715 B1 | 12/2002 | Pope et al. |
| 6,503,281 B1 | 1/2003 | Mallory |
| 6,537,321 B1 * | 3/2003 | Horber ............... A61F 2/34 623/22.22 |
| 6,641,617 B1 | 11/2003 | Merrill et al. |
| 6,682,566 B2 | 1/2004 | Draenert |
| 6,726,725 B2 | 4/2004 | Hunter et al. |
| 6,811,569 B1 | 11/2004 | Atrial et al. |
| 7,004,972 B2 | 2/2006 | Yoon |
| 7,044,974 B2 * | 5/2006 | Garber ............... A61F 2/34 623/22.21 |
| 7,108,720 B2 * | 9/2006 | Hanes ............... A61F 2/32 623/22.11 |
| 7,179,298 B2 | 2/2007 | Greenlee |
| 7,211,113 B2 | 5/2007 | Zelener et al. |
| 7,335,231 B2 | 2/2008 | McLean |
| 7,455,694 B2 | 11/2008 | Epaules et al. |
| 7,494,509 B1 | 2/2009 | Hershberger et al. |
| 7,572,296 B2 | 8/2009 | Scott et al. |
| 7,682,398 B2 | 3/2010 | Croxton et al. |
| 7,794,504 B2 | 9/2010 | Case |
| 7,985,261 B2 | 7/2011 | Masini |
| 8,123,814 B2 * | 2/2012 | Meridew ............... A61F 2/30724 623/22.19 |
| 8,177,850 B2 | 5/2012 | Rudan et al. |
| 8,211,183 B2 | 7/2012 | Podolsky |
| 8,211,184 B2 | 7/2012 | Ries et al. |
| 8,268,383 B2 | 9/2012 | Langhorn |
| 8,308,810 B2 * | 11/2012 | Meridew ............... A61F 2/34 623/22.19 |
| 8,398,718 B2 | 3/2013 | Richardson |
| 8,465,549 B2 | 6/2013 | Richardson |
| 8,771,366 B2 | 7/2014 | Whitaker |
| 8,858,645 B2 * | 10/2014 | Grostefon ............... A61F 2/32 623/22.15 |
| 9,023,112 B2 * | 5/2015 | Komistek ............... A61F 2/32 623/22.15 |
| 9,241,799 B2 * | 1/2016 | Grostefon ............... A61F 2/32 |
| 9,700,416 B2 * | 7/2017 | Grostefon ............... A61F 2/32 |
| 2003/0171817 A1 * | 9/2003 | Rambert ............... A61F 2/32 623/22.17 |
| 2003/0212459 A1 | 11/2003 | Gibbs |
| 2003/0236572 A1 | 12/2003 | Bertram, III |
| 2004/0078083 A1 | 4/2004 | Gibbs et al. |
| 2004/0143341 A1 | 7/2004 | McLean |
| 2004/0193282 A1 | 9/2004 | Hanes |
| 2004/0204767 A1 | 10/2004 | Park et al. |
| 2004/0225371 A1 | 11/2004 | Roger |
| 2005/0096748 A1 | 5/2005 | Yoon |
| 2005/0261776 A1 | 11/2005 | Taylor |
| 2006/0167556 A1 | 7/2006 | Lazennec et al. |
| 2006/0206211 A1 | 9/2006 | Daniels et al. |
| 2006/0217815 A1 | 9/2006 | Gibbs et al. |
| 2007/0100447 A1 | 5/2007 | Steinberg |
| 2007/0106389 A1 * | 5/2007 | Croxton ............... A61F 2/30942 623/22.17 |
| 2007/0225818 A1 | 9/2007 | Reubelt et al. |
| 2008/0015707 A1 | 1/2008 | Lambert et al. |
| 2008/0114459 A1 | 5/2008 | Scott et al. |
| 2008/0177395 A1 | 7/2008 | Stinnette |
| 2008/0208350 A1 | 8/2008 | Roger |
| 2008/0221699 A1 * | 9/2008 | Meridew ............... A61F 2/34 623/22.29 |
| 2008/0294258 A1 | 11/2008 | Revie et al. |
| 2009/0018666 A1 | 1/2009 | Grundei et al. |
| 2009/0088866 A1 | 4/2009 | Case |
| 2009/0093887 A1 | 4/2009 | Walter et al. |
| 2009/0105714 A1 | 4/2009 | Kozak |
| 2009/0171464 A1 | 7/2009 | Imhof |
| 2009/0204225 A1 | 8/2009 | Meridew et al. |
| 2009/0259317 A1 | 10/2009 | Steinberg |
| 2009/0281545 A1 | 11/2009 | Stubbs |
| 2009/0287311 A1 | 11/2009 | Preuss et al. |
| 2010/0261998 A1 | 10/2010 | Stiehl |
| 2011/0009975 A1 * | 1/2011 | Allen ............... A61F 2/30767 623/22.24 |
| 2011/0032184 A1 | 2/2011 | Roche et al. |
| 2011/0054628 A1 | 3/2011 | Banks et al. |
| 2011/0087335 A1 * | 4/2011 | Newsome ............... A61F 2/30721 623/22.29 |
| 2012/0029651 A1 | 2/2012 | Ashton et al. |
| 2012/0065737 A1 | 3/2012 | Chow |

(56) References Cited

U.S. PATENT DOCUMENTS

| | | | |
|---|---|---|---|
| 2012/0109327 A1 | 5/2012 | Forsell | |
| 2012/0209397 A1 | 8/2012 | Richardson | |
| 2012/0209398 A1* | 8/2012 | Richardson | A61F 2/34 623/22.17 |
| 2012/0221115 A1 | 8/2012 | Komistek | |
| 2013/0158557 A1 | 6/2013 | Komistek | |
| 2013/0158674 A1 | 6/2013 | Chow et al. | |
| 2013/0165938 A1 | 6/2013 | Chow et al. | |
| 2013/0304225 A1 | 11/2013 | Komistek | |
| 2013/0345822 A1* | 12/2013 | Grostefon | A61F 2/32 623/22.16 |
| 2015/0305872 A1* | 10/2015 | Komistek | A61F 2/32 623/22.29 |
| 2017/0027704 A1* | 2/2017 | Komistek | A61F 2/32 |

FOREIGN PATENT DOCUMENTS

| | | |
|---|---|---|
| DE | 10212982 A1 | 10/2003 |
| EP | 0380045 A1 | 8/1990 |
| EP | 0524857 A1 | 1/1993 |
| EP | 0648478 A2 | 7/1994 |
| EP | 0649640 A2 | 4/1995 |
| EP | 0797964 A1 | 10/1997 |
| EP | 1406203 A2 | 4/2004 |
| EP | 1508315 A2 | 2/2005 |
| EP | 1574183 A1 | 9/2005 |
| FR | 2785523 A1 | 5/2000 |
| FR | 27862390 A1 | 6/2000 |
| FR | 2843294 A1 | 2/2004 |
| FR | 2889446 A1 | 2/2007 |
| GB | 1573608 A | 8/1980 |
| JP | 63-19141 A | 1/1988 |
| JP | 2003-190194 A | 7/2003 |
| JP | 2004-526532 A | 9/2004 |
| JP | 2009-56341 A | 3/2009 |
| JP | 2009-78188 A | 4/2009 |
| JP | 4387177 B2 | 12/2009 |
| JP | 2010-12288 A | 1/2010 |
| JP | 4417373 B2 | 2/2010 |
| JP | 4849999 B2 | 1/2012 |
| RU | 2042345 C1 | 8/1995 |
| RU | 2116769 C1 | 10/1998 |
| WO | 9615735 A1 | 3/1996 |
| WO | 0064384 A1 | 11/2000 |
| WO | 0155476 A1 | 8/2001 |
| WO | 2008058756 A2 | 5/2008 |
| WO | 2009106816 | 2/2009 |
| WO | 2009118673 A1 | 10/2009 |

OTHER PUBLICATIONS

International Search Report, International Application No. PCT/US2012/026492, dated Aug. 31, 2012, 16 pages.

English Translation, Office Action for Japanese Patent Application 2013-555594 dated Nov. 24, 2015, 3 pages.

English translation of Japanese Office Action issued in connection with Japanese Application No. 2016-119671, dated May 8, 2017, 6 pages.

European Search Report Application No. 12776797.8, dated Jul. 18, 2017, 9 pages.

European Search Report, European Application No. 18152814.2-1122, dated Apr. 5, 2018, 5 pages.

European Search Report and Written Opinion for European Patent Application No. 18152814.2, completed Apr. 5, 2018, 4 pages.

\* cited by examiner

METHODS FOR MAINTAINING PROPER MECHANICS THA

CROSS REFERENCE TO RELATED APPLICATIONS

This application is a divisional of pending U.S. patent application Ser. No. 14/700,988, which was filed on Apr. 30, 2015, which is a continuation of U.S. patent application Ser. No. 13/034,226, now U.S. Pat. No. 9,023,112, which was filed on Feb. 24, 2011, the disclosures of which are hereby incorporated by reference.

RELATED ART

Field of the Invention

The present disclosure relates to orthopedic hip implants, components thereof, and methods of preparing native tissue for implantation of a foreign object, as well as methods of implanting foreign objects such as orthopedic hips and components thereof.

Brief Discussion of Related Art

A common problem in artificial hips is dislocation resulting from the ball of the femoral head no longer being fully seated within the acetabular cup. Dislocation is particularly problematic immediately after artificial hip replacement or revision surgery. As those skilled in the art are aware, soft tissues surrounding the natural joint are damaged or removed during surgery in order to make way for the replacement orthopedic implant. Even in circumstances of artificial joint revision surgery, soft tissues are damaged to gain access to the artificial joint.

Dislocation is problematic in numerous respects. First, dislocation creates obvious kinematic problems as the joint components are not aligned to function as designed or intended. Second, dislocation usually results in joint pain from the unintended loads placed on surrounding tissues. Third, dislocation usually results in swelling of tissues surrounding the joint. Fourth, dislocation can create "popping" sounds that correlate with the ball entering and exiting the cup repetitively. Fifth, dislocation causes moments to be created in the joint. Sixth, dislocation leads to premature wear of the cup and/or femoral head, thereby increasing the likelihood of joint failure or loosening of the joint.

Many hypothesizes exist as to the cause of dislocation as well as methods and devices to reduce or inhibit dislocation. For example, certain orthopedic hip joints include permanent retention rings to lock the femoral head into the acetabular cup. But these retention rings come at a price—decreased range of motion. As the age of patients undergoing joint replacement and revision surgeries drops and activity level of older adults increases, decreased range of motion is not a trade-off most patients are willing to make to inhibit dislocation.

Another problem with existing THA is the incidence of femoral head separation within the acetabular cup, leading to the femoral head sliding out in the superior-lateral direction and then back in the inferior-medial direction. This incidence of sliding of the femoral head within the acetabular cup leads to the observation that present day THA do not function as a revolute joint, but rather have induced undesirable shear forces that do not exist in the native hip joint. This inducement of femoral head separation may be a main reason for the occurrence of hip dislocation.

INTRODUCTION

It is a first aspect of the present invention to provide an orthopedic hip joint comprising: (a) an implantable femoral component having a first resonant frequency; (b) an implantable acetabular component having a second resonant frequency; and, (c) a vibrational damper mounted to at least one of the implantable femoral component and the implantable acetabular component, where a frequency resulting from interaction between the femoral component and the acetabular component approximates a resonant frequency of at least one of a femur, a pelvis, and connective tissue around a hip joint.

In a more detailed embodiment of the first aspect, the implantable femoral component includes a femoral stem, a femoral neck, and a femoral head, the femoral neck is separable from the femoral head and, the vibrational dampener comprises at least a portion of the femoral neck. In yet another more detailed embodiment, the implantable femoral component includes a femoral stem, a femoral neck, and a femoral head, the femoral neck is separable from the femoral head and, the vibrational dampener interposes the femoral neck and the femoral head. In a further detailed embodiment, the implantable femoral component includes a femoral stem, a femoral neck, and a femoral head and, the vibrational dampener comprises a sleeve wrapped around the femoral stem. In still a further detailed embodiment, the implantable acetabular component includes an acetabular cup and an acetabular cup insert and, the vibrational dampener interposes the acetabular cup and the acetabular cup insert. In a more detailed embodiment, the implantable acetabular component includes an acetabular cup and an acetabular cup insert and, the vibrational dampener is mounted to a bone side of the acetabular cup. In a more detailed embodiment, the vibrational damper comprises at least one of silicone rubber, elastic silicone rubber, gutta percha, saline rubber, gore-tex, polystyrene, polytetrafluoroethylene, nylon, polyethylene, polyester, silk, polyethylene teraphthalate, and polyvinyl alcohol-hydrogel.

It is a second aspect of the present invention to provide a method of reducing propagation of vibrations through at least one component of an orthopedic hip joint, the method comprising mounting a vibrational damper to at least one of a femoral component and an acetabular component of an orthopedic hip joint.

In a more detailed embodiment of the second aspect, the femoral component includes a femoral stem, a femoral neck, and a femoral head and, the vibrational dampener comprises a sleeve wrapped around the femoral stem. In yet another more detailed embodiment, the femoral component includes a femoral stem, a femoral neck, and a femoral head and, the vibrational dampener interposes the femoral neck and femoral head. In a further detailed embodiment, the acetabular component includes an acetabular cup and an acetabular cup insert and, the vibrational dampener interposes the acetabular cup and the acetabular cup insert. In still a further detailed embodiment, the acetabular component includes an acetabular cup and an acetabular cup insert and, the vibrational dampener is mounted to a bone side of the acetabular cup.

It is a third aspect of the present invention to provide an orthopedic hip joint comprising: (a) an implantable femoral component includes a first magnet exhibiting a first magnetic field; and, (b) an implantable acetabular component includes a second magnet exhibiting a second magnetic field.

In a more detailed embodiment of the third aspect, the implantable femoral component includes a femoral stem, a femoral neck, and a femoral head, the femoral head includes the first magnet and, the first magnet is oriented so that upon implantation its positive pole is nearer the second magnet than a negative pole of the first magnet. In yet another more detailed embodiment, the implantable acetabular component includes an acetabular cup and an acetabular cup insert and, the second magnet is oriented so that upon implantation its negative pole is nearer the positive pole of the first magnet than is a positive pole of the second magnet. In a further detailed embodiment, the implantable acetabular component includes an acetabular cup and an acetabular cup insert and, the second magnet is oriented so that upon implantation its positive pole is nearer the positive pole of the first magnet than is a negative pole of the second magnet. In still a further detailed embodiment, the implantable femoral component includes a femoral stem, a femoral neck, and a femoral head, the femoral head includes the first magnet and, the first magnet is oriented so that upon implantation its negative pole is nearer the second magnet than a positive pole of the first magnet. In a more detailed embodiment, the implantable acetabular component includes an acetabular cup and an acetabular cup insert and, the second magnet is oriented so that upon implantation its negative pole is nearer the negative pole of the first magnet than is a positive pole of the second magnet. In a more detailed embodiment, the implantable acetabular component includes an acetabular cup and an acetabular cup insert and, the second magnet is oriented so that upon implantation its positive pole is nearer the negative pole of the first magnet than is a negative pole of the second magnet. In another more detailed embodiment, the acetabular component comprises an acetabular cup and an acetabular cup insert and, the second magnet is part of the acetabular cup. In yet another more detailed embodiment, the acetabular component comprises an acetabular cup and an acetabular cup insert and, the second magnet is part of the acetabular cup insert. In still another more detailed embodiment, the acetabular component comprises an acetabular cup and an acetabular cup insert, the acetabular component includes a plurality of magnets, where the plurality of magnets include the second magnet and, at least two of the plurality of magnets are oriented so that a negative pole of each magnet is upon implantation closer to a femoral head of the femoral component than is a positive pole of each magnet.

In yet another more detailed embodiment of the third aspect, the at least two of the plurality of magnets are symmetrically oriented with respect to an axis extending through the acetabular component. In still another more detailed embodiment, the at least two of the plurality of magnets are asymmetrically oriented with respect to an axis extending through the acetabular component. In a further detailed embodiment, the acetabular component comprises an acetabular cup and an acetabular cup insert, the acetabular component includes a plurality of magnets, where the plurality of magnets include the second magnet and, at least two of the plurality of magnets are oriented so that a positive pole of each magnet is upon implantation closer to a femoral head of the femoral component than is a negative pole of each magnet. In still a further detailed embodiment, the at least two of the plurality of magnets are symmetrically oriented with respect to an axis extending through the acetabular component. In a more detailed embodiment, the at least two of the plurality of magnets are asymmetrically oriented with respect to an axis extending through the acetabular component.

It is a fourth aspect of the present invention to provide a method of decreasing impact forces between orthopedic hip joint components, the method comprising: (a) associating a first magnetic field with a femoral component of an orthopedic joint, the first magnetic field having a positive pole and a negative pole; and, (b) associating a second magnetic field with an acetabular component of the orthopedic joint, the second magnetic field having a positive pole and a negative pole, where at least one of the positive poles and the negative poles are nearer one another than is the other of the positive poles and the negative poles.

In a more detailed embodiment of the fourth aspect, the act of associating the first magnetic field with the femoral component includes including a magnet as part of a femoral head, the magnet of the femoral head is oriented so the positive pole is nearer the acetabular component than is the negative pole, the act of associating the second magnetic field with the acetabular component includes including a magnet as part of at least one of an acetabular cup and an acetabular cup insert and, the magnet of the acetabular component is oriented so the positive pole is nearer the positive pole of the magnet of the femoral component than is the negative pole. In yet another more detailed embodiment, the act of associating the first magnetic field with the femoral component includes including a magnet as part of a femoral head, the magnet of the femoral head is oriented so the negative pole is nearer the acetabular component than is the positive pole, the act of associating the second magnetic field with the acetabular component includes including a magnet as part of at least one of an acetabular cup and an acetabular cup insert and, the magnet of the acetabular component is oriented so the negative pole is nearer the positive pole of the magnet of the femoral component than is the positive pole. In a further detailed embodiment, the magnet of the femoral component is part of the acetabular cup. In still a further detailed embodiment, the magnet of the femoral component is part of the acetabular cup insert. In a more detailed embodiment, the step of associating a second magnetic field with the acetabular component of the orthopedic joint includes establishing a plurality of positive poles and a plurality of negative poles.

It is a fifth aspect of the present invention to provide a method of retarding dislocation between a femoral component and an acetabular component of an orthopedic hip joint, the method comprising: (a) associating a first magnetic field with a femoral component of an orthopedic joint, the first magnetic field having a positive pole and a negative pole; and, (b) associating a second magnetic field with an acetabular component of the orthopedic joint, the second magnetic field having a positive pole and a negative pole, where an attraction force between one of the positive poles and one of the negative poles operates to retard dislocation between the femoral component and the acetabular component upon implantation.

In a more detailed embodiment of the fifth aspect, the act of associating the first magnetic field with the femoral component includes including a magnet as part of a femoral head, the magnet of the femoral head is oriented so the positive pole is nearer the acetabular component than is the negative pole, the act of associating the second magnetic field with the acetabular component includes including a magnet as part of at least one of an acetabular cup and an acetabular cup insert and, the magnet of the acetabular component is oriented so the negative pole is nearer the positive pole of the magnet of the femoral component than is the positive pole. In yet another more detailed embodiment, the act of associating the first magnetic field with the femoral component includes including a magnet as part of a femoral head, the magnet of the femoral head is oriented so the negative pole is nearer the acetabular component than is the positive pole, the act of associating the second magnetic field with the acetabular component includes including a magnet as part of at least one of an acetabular cup and an acetabular cup insert and, the magnet of the acetabular component is oriented so the positive pole is nearer the negative pole of the magnet of the femoral component than is the negative pole. In a further detailed embodiment, the magnet of the femoral component is part of the acetabular cup. In still a further detailed embodiment, the magnet of the femoral component is part of the acetabular cup insert. In a more detailed embodiment, the step of associating a second magnetic field with the acetabular component of the orthopedic joint includes establishing a plurality of positive poles and a plurality of negative poles.

It is a sixth aspect of the present invention to provide a prosthetic hip joint comprising: (a) a femoral component including a femoral head; and, (b) an acetabular component including an acetabular cup and an acetabular cup insert, the acetabular cup insert sized to receive the femoral head, where the femoral head is sized to have a spherical center that matches a spherical center of a patient's native femoral head, where the acetabular cup is sized to have a cavity with a spherical center that matches a spherical center of a cavity of a patient's native acetabulum and, where the femoral head center of the femoral component is concentric with the center of the cavity of the acetabular cup.

In a more detailed embodiment of the sixth aspect, the spherical center of the patient's native femoral head is determined from the interface of the native femoral head with the native acetabulum during walking. In yet another more detailed embodiment, the spherical center of the patient's native acetabulum is determined from the interface of the native femoral head with the native acetabulum during walking. In a further detailed embodiment, the patient's native femoral head includes cartilage mounted to the native femoral head. In still a further detailed embodiment, the cavity of the patient's native acetabulum includes cartilage mounted to the native acetabulum. In a more detailed embodiment, a radial thickness of the acetabular cup is nonuniform along a circumferential length. In a more detailed embodiment, a radial thickness of the femoral head is nonuniform along a circumferential length. In another more detailed embodiment, an outer aspect of the acetabular cup is nonspherical and an inner aspect of the acetabular cup is spherical. In yet another more detailed embodiment, an outer aspect of the acetabular cup is spherical and an inner aspect of the acetabular cup is nonspherical.

It is a seventh aspect of the present invention to provide a method of designing an orthopedic hip joint implant, the method comprising: (a) conducting a kinematic analysis of a population eligible for hip replacement surgery; (b) establishing contact points between a native femur and a native acetabulum for each person in the population using the kinematic analysis; (c) creating an imaginary sphere that correlates with the contact points for each person in the population; (d) determining a dimension of the imaginary sphere for each person in the population including at least one of radius, diameter, circumference, and center point; and, (e) designing at least one of a femoral component and an acetabular component using the dimension of the imaginary sphere for each person in the population.

In a more detailed embodiment of the seventh aspect, the determining step includes determining the center point of the imaginary sphere, where the center point represents the anatomical spherical center and, the designing step includes designing the femoral component to have a femoral ball with a spherical curvature, the spherical curvature corresponding to an imaginary prosthetic sphere having a center that is the same as the anatomical spherical center. In yet another more detailed embodiment, the population comprises a single person. In a further detailed embodiment, the population comprises a plurality of persons having at least one common trait taken from the group of age, gender, race, height, bone size. In still a further detailed embodiment, the conducting step includes observing a hip joint of each person in the population, where the observation takes place while the hip joint is under weight-bearing stress. In a more detailed embodiment, the observation includes using at least one of fluoroscopy, magnetic resonance imaging, CT imaging, ultrasound. In a more detailed embodiment, the conducting step includes observing a hip joint of each person in the population and, the conducting step includes creating a three dimensional model of the hip joint for each person in the population. In another more detailed embodiment, the establishing step includes utilizing a collision detection analysis to establish the contact points between the native femur and the native acetabulum for each person in the population using the three dimensional model of the hip joint. In yet another more detailed embodiment, the invention further includes mapping a location of the imaginary sphere for each person in the population with respect to boney landmarks.

It is a ninth aspect of the present invention to provide a method of fabricating an orthopedic hip joint, the method comprising: (a) conducting a kinematic analysis of a population eligible for hip replacement surgery; (b) establishing contact points between a native femur and a native acetabulum for each person in the population using the kinematic analysis; (c) creating a sphere that correlates with the contact points for each person in the population; (d) determining a dimension of the sphere for each person in the population including at least one of radius, diameter, circumference, and center point; (e) designing at least one of a femoral component and an acetabular component using the dimension of the sphere for each person in the population; and, (f) fabricating at least one of the femoral component and the acetabular component.

In a more detailed embodiment of the ninth aspect, the determining step includes determining the center point of the imaginary sphere, where the center point represents the anatomical spherical center and, the designing step includes designing the femoral component to have a femoral ball with a spherical curvature, the spherical curvature corresponding to an imaginary prosthetic sphere having a center that is the same as the anatomical spherical center. In yet another more detailed embodiment, the population comprises a single person. In a further detailed embodiment, the population comprises a plurality of persons having at least one common trait taken from the group of age, gender, race, height, bone size. In still a further detailed embodiment, the conducting step includes observing a hip joint of each person in the population, where the observation takes place while the hip joint is under weight-bearing stress. In a more detailed embodiment, the observation includes using at least one of fluoroscopy, magnetic resonance imaging, CT imaging, ultrasound. In a more detailed embodiment, the conducting step includes observing a hip joint of each person in the population and, the conducting step includes creating a three dimensional model of the hip joint for each person in the population. In another more detailed embodiment, the establishing step includes utilizing a collision detection analysis to establish the contact points between the native femur and the native acetabulum for each person in the population using the three dimensional model of the hip joint. In yet another more detailed embodiment, the invention further includes mapping a location of the imaginary sphere for each person in the population with respect to boney landmarks.

It is a tenth aspect of the present invention to provide an acetabular cup comprising a bowl-shaped wall at least partially delineating a concavity, the bowl-shaped wall including a top perimeter demarcating a first opening through the bowl-shaped wall, the bowl-shaped wall also demarcating a second opening sized to allow throughput of at least a portion of a femoral head ligament.

In a more detailed embodiment of the tenth aspect, the invention also includes at least one tab operatively coupled to the wall, the at least one tab including a through hole. In yet another more detailed embodiment, the invention also includes a plurality of tabs circumferentially distributed about the top perimeter of the wall, each of the plurality of tabs having a through hole. In a further detailed embodiment, the invention also includes a plurality of guide pins each sized to allow insertion into the through hole of each tab.

It is an eleventh aspect of the present invention to provide a femoral component of a prosthetic hip joint comprising a femoral stem adapted to be inserted into the intramedullary canal of a femur, the femoral stem coupled to a femoral neck, the femoral neck extending proximally away from the femoral stem, the femoral neck operatively coupled to a femoral ball mounted to a proximal end of the femoral neck, where the femoral ball includes a proximal cavity.

In a more detailed embodiment of the eleventh aspect, the proximal cavity of the femoral ball is a through hole extending through the femoral ball. In yet another more detailed embodiment, the proximal cavity extends into the femoral neck. In a further detailed embodiment, the proximal cavity extends into the femoral stem. In still a further detailed embodiment, the femoral stem, femoral neck, and femoral ball comprise a single piece. In a more detailed embodiment, the proximal cavity has at least one of a circular cross-section, a rectangular cross-section, and an irregular cross-section.

It is a twelfth aspect of the present invention to provide a method of mounting an acetabular component to a patient, the method comprising: (a) positioning and aligning an acetabular jig with respect to an acetabulum, where the acetabular jig includes a bowl-shaped wall having a through hole accommodating throughput of a portion of a femoral head ligament attached to the acetabulum; (b) drilling reference holes proximate the acetabulum using the acetabular jig as a guide; and, (c) inserting a pin into each reference hole, where the positioning and aligning step includes inserting the portion of the femoral head ligament attached to the acetabulum through the through hole of the acetabular jig.

In a more detailed embodiment of the twelfth aspect, the method further includes positioning a guide cup with respect to the pelvis using the pins, mounting a guide pin to the acetabulum while the guide cup is in position and, removing the guide cup after the guide pin is mounted to the acetabulum.

It is a thirteenth aspect of the present invention to provide a prosthetic hip joint comprising: (a) a femoral component including a femoral head with a femoral head cavity; and, (b) an acetabular component including an acetabular cup and an acetabular cup insert, the acetabular cup insert and the acetabular cup each having a through hole, where the through holes overlap a location of a native femoral head ligament.

In a more detailed embodiment of the thirteenth aspect, the femoral head cavity is sized to receive a portion of a native femur that remains attached to the native femoral head ligament. In yet another more detailed embodiment, the femoral head cavity extends into a neck of the femoral component. In a further detailed embodiment, the femoral head cavity extends through a neck of the femoral component and into a shaft of the femoral component. In still a further detailed embodiment, the through holes of the acetabular cup and acetabular cup insert are oriented to align with a location where a femoral head ligament is mounted to an acetabulum.

It is a fourteenth aspect of the present invention to provide a method of implanting an orthopedic hip joint, the method comprising: (a) implanting and mounting an acetabular component to a native acetabulum; (b) implanting and mounting a femoral component to a native femur; and, (c) maintaining a connection between a native femoral head ligament and at least one of the native acetabulum and the native femur after implanting and mounting the acetabular component and the femoral component.

In a more detailed embodiment of the fourteenth aspect, the method further includes reshaping a portion of a native femoral head attached to the native femoral head ligament to create a femoral revision and, coupling the femoral component to the femoral revision. In yet another more detailed embodiment, the invention further includes severing the native femoral head from the native femur, wherein the femoral revision comprises a femoral bone insert mounted to the native femoral head ligament, and wherein the act of coupling the femoral component to the femoral revision includes inserting the femoral bone insert into a cavity of the femoral component. In a further detailed embodiment, the cavity extends into a neck of the femoral component. In still a further detailed embodiment, the cavity extends through a neck of the femoral component and into a shaft of the femoral component.

It is a fifteenth aspect of the present invention to provide a method of implanting at least one orthopedic hip joint component, the method comprising: (a) implanting and mounting at least one of an acetabular component to a native acetabulum and a femoral component to a native femur; and, (b) maintaining a connection between a native femoral head ligament and at least one of the native acetabulum and the native femur.

In a more detailed embodiment of the fifteenth aspect, the implanting act includes mounting the acetabular component to the native acetabulum and, the acetabular component includes a cup having an orifice through which the native femoral head ligament extends. In yet another more detailed embodiment, the implanting act includes mounting the femoral component to the native femur and, the femoral component includes a cavity to receive at least a portion of the native femur connected to the native femoral head ligament. In a further detailed embodiment, the invention further includes reshaping a portion of a native femoral head attached to the native femoral head ligament to create a femoral revision, implanting and mounting the femoral component to the native femur and, coupling the femoral component to the femoral revision. In still a further detailed embodiment, the invention further includes severing the native femoral head from the native femur, wherein the femoral revision comprises a femoral bone insert, and wherein the act of coupling the femoral component to the femoral revision includes inserting the femoral bone insert into a cavity of the femoral component. In a more detailed embodiment, the implanting act includes implanting and mounting the acetabular component to the native acetabulum and, the implanting act includes implanting and mounting the femoral component to the native femur. In a more detailed embodiment, the invention further includes mounting a first portion of a tether to at least one of the native acetabulum and the acetabular component, and mounting a second portion of the tether to at least one of the native femur and the femoral component.

It is a sixteenth aspect of the present invention to provide an acetabular component of a prosthetic hip joint comprising: (a) an acetabular cup adapted to be mounted to a native acetabulum; (b) a first acetabular cup insert to be mounted to the acetabular cup and repositionable with respect to the acetabular cup; and, (c) a second acetabular cup insert to be mounted to the first acetabular cup insert and repositionable with respect to the first acetabular cup insert, the first acetabular cup insert interposing the second acetabular cup insert and the acetabular cup.

In a more detailed embodiment of the sixteenth aspect, the acetabular cup includes a circumferential groove on an interior surface thereof, the first acetabular cup includes a projection that is received within the circumferential groove and, the projection is repositionable with respect to the circumferential groove. In yet another more detailed embodiment, the first acetabular cup insert includes a circumferential groove on an exterior surface thereof, the acetabular cup includes a projection on an interior surface thereof and, the circumferential groove is repositionable with respect to the projection. In a further detailed embodiment, the first acetabular cup insert includes a circumferential groove on an interior surface thereof, the second acetabular cup includes a projection that is received within the circumferential groove and, the projection is repositionable with respect to the circumferential groove. In still a further detailed embodiment, the second acetabular cup insert includes a circumferential groove on an exterior surface thereof, the first acetabular cup insert includes a projection on an interior surface thereof and, the circumferential groove is repositionable with respect to the projection. In a more detailed embodiment, the first acetabular cup insert is slidably repositionable with respect to the acetabular cup within a first plane, the first acetabular cup insert is slidably repositionable with respect to the second acetabular cup insert within a second plane and, the first plane is generally perpendicular with respect to the second plane. In a more detailed embodiment, the first acetabular cup insert is rotationally repositionable with respect to the acetabular cup and, the first acetabular cup insert is slidably repositionable with respect to the second acetabular cup insert. In another more detailed embodiment, the first acetabular cup insert is slidably repositionable with respect to the acetabular cup and, the first acetabular cup insert is rotationally repositionable with respect to the second acetabular cup insert.

It is a seventeenth aspect of the present invention to provide a method of assembling a mobile bearing acetabular component of a prosthetic hip joint, the method comprising: (a) mounting a first acetabular cup insert to an acetabular cup, where mounting the first acetabular cup insert to the acetabular cup includes repositioning the first acetabular cup insert with respect to the acetabular cup without disengaging the first acetabular cup insert from the acetabular cup; and, (b) mounting a second acetabular cup insert to the first acetabular cup insert, where mounting the second acetabular cup insert to the first acetabular cup includes repositioning the second acetabular cup insert with respect to the first acetabular cup insert without disengaging the second acetabular cup insert from the first acetabular cup insert.

In a more detailed embodiment of the seventeenth aspect, repositioning the first acetabular cup insert with respect to the acetabular cup includes sliding the first acetabular cup insert against the acetabular cup and, repositioning the second acetabular cup insert with respect to the first acetabular cup insert includes sliding the second acetabular cup insert against the first acetabular cup insert. In yet another more detailed embodiment, repositioning the first acetabular cup insert with respect to the acetabular cup includes rotating the first acetabular cup insert against the acetabular cup and, repositioning the second acetabular cup insert with respect to the first acetabular cup insert includes sliding the second acetabular cup insert against the first acetabular cup insert. In a further detailed embodiment, repositioning the first acetabular cup insert with respect to the acetabular cup includes sliding the first acetabular cup insert against the acetabular cup and, repositioning the second acetabular cup insert with respect to the first acetabular cup insert includes rotating the second acetabular cup insert against the first acetabular cup insert.

It is an eighteenth aspect of the present invention to provide an acetabular component of a prosthetic hip joint comprising: (a) an acetabular cup adapted to be mounted to a native acetabulum; and, (b) a first acetabular cup insert to be mounted to the acetabular cup and repositionable with respect to the acetabular cup, the first acetabular cup insert is concurrently repositionable deeper into an interior of the acetabular cup and repositionable outside of an outline of the acetabular cup.

In a more detailed embodiment of the eighteenth aspect, the acetabular cup includes a circumferential groove on an interior surface thereof, the first acetabular cup includes a projection that is received within the circumferential groove and, the projection is repositionable with respect to the circumferential groove. In yet another more detailed embodiment, the first acetabular cup insert includes a circumferential groove on an exterior surface thereof, the acetabular cup includes a projection on an interior surface thereof and, the circumferential groove is repositionable with respect to the projection.

It is a nineteenth aspect of the present invention to provide a method of assembling a mobile bearing acetabular component of a prosthetic hip joint, the method comprising mounting a first acetabular cup insert to an acetabular cup, where mounting the first acetabular cup insert to the acetabular cup includes concurrently repositioning the first acetabular cup insert deeper into an interior of the acetabular cup and repositioning the first acetabular cup insert outside of an outline of the acetabular cup.

In a more detailed embodiment of the nineteenth aspect, repositioning the first acetabular cup insert with respect to the acetabular cup includes sliding the first acetabular cup insert against the acetabular cup.

It is a twentieth aspect of the present invention to provide a method of revising a proximal aspect of a native femur to receive a femoral component of a prosthetic hip joint, the method comprising: (a) removing a native femoral head from a native femur; (b) reshaping a neck of the native femur; and, (c) mounting a prosthetic femoral component onto the reshaped neck.

In a more detailed embodiment of the twentieth aspect, the prosthetic femoral component comprises a femoral ball. In yet another more detailed embodiment, the prosthetic femoral component comprises a femoral ball and a femoral neck sleeve. In a further detailed embodiment, the femoral neck sleeve is cylindrical. In still a further detailed embodiment, the femoral neck sleeve is frustoconical.

It is a twenty-first aspect of the present invention to provide an orthopedic hip joint comprising: (a) an implantable femoral component having a first resonant frequency; and, (b) an implantable acetabular component having a second resonant frequency, where a frequency resulting from interaction between the femoral component and the acetabular component is different from a resonant frequency of at least one of a femur, a pelvis, and connective tissue around a hip joint.

In a more detailed embodiment of the twenty-first aspect, the implantable femoral component includes a femoral stem, a femoral neck, and a femoral head and, the femoral neck is separable from the femoral head. In yet another more detailed embodiment, the implantable acetabular component includes an acetabular cup and an acetabular cup insert.

It is a twenty-second aspect of the present invention to provide a method of designing an orthopedic hip joint, the method comprising: (a) creating an implantable femoral component having a first resonant frequency; and, (b) creating an implantable acetabular component having a second resonant frequency, where a frequency resulting from interaction between the femoral component and the acetabular component is different from a resonant frequency of at least one of a femur, a pelvis, and connective tissue around a hip joint.

In a more detailed embodiment of the twenty-second aspect, the femoral component includes a femoral stem, a femoral neck, and a femoral head. In yet another more detailed embodiment, the acetabular component includes an acetabular cup and an acetabular cup insert.

DETAILED DESCRIPTION

The exemplary embodiments of the present disclosure are described and illustrated below to encompass orthopedic hip implants, components thereof, and methods of preparing native tissue for implantation of a foreign object, as well as methods of implanting foreign objects such as orthopedic hips and components thereof. Of course, it will be apparent to those of ordinary skill in the art that the preferred embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Figure 1:
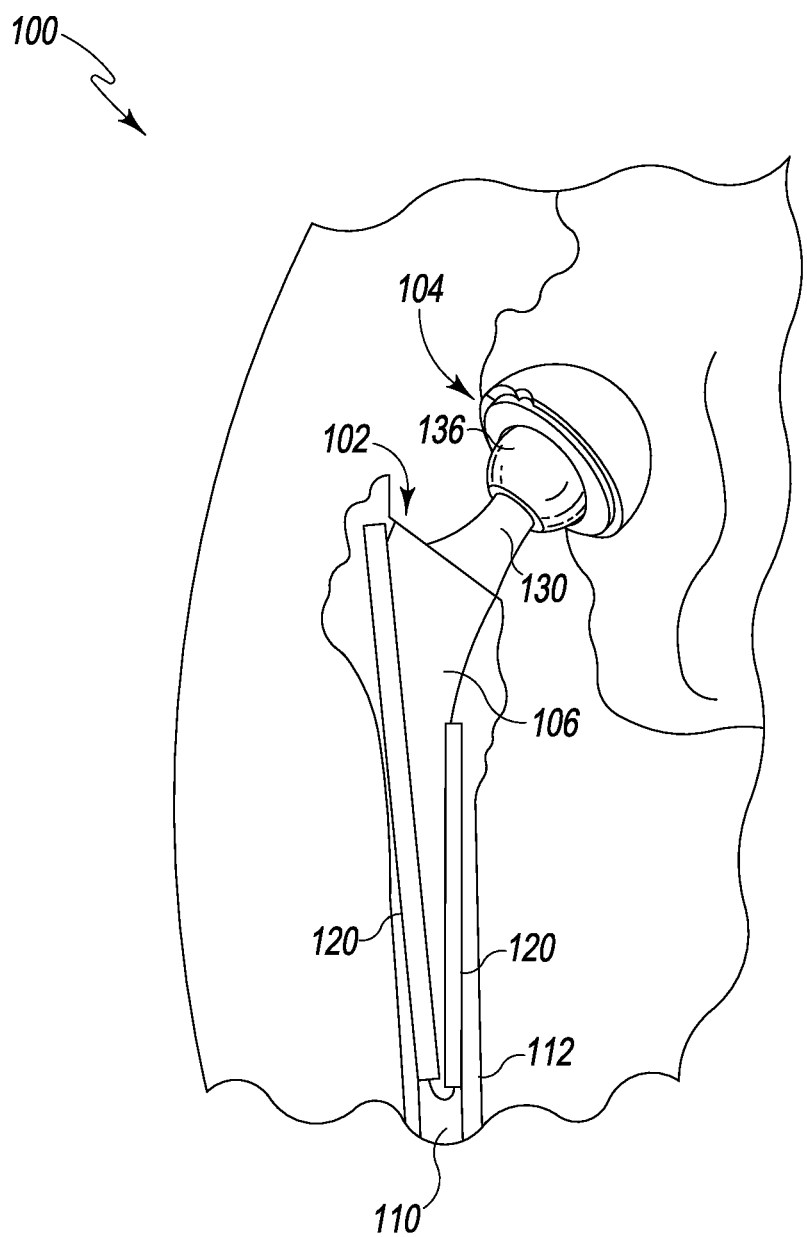
FIG. 1 is an elevated perspective view of a first exemplary prosthetic hip joint in accordance with the instant disclosure, shown with a ghost image of the patient's natural anatomy.

Referring to FIG. 1, a first exemplary prosthetic hip joint 100 includes a femoral component 102 cooperating with an acetabular component 104. In exemplary form, the femoral component 102 includes a femoral stem 106 for implantation into the proximal intramedullary canal 110 of a femur 112 in order to secure the femoral component to the femur. The femoral stem 106 may be fabricated from any feasible material, including metals such as, without limitation, titanium, cobalt chromium, and stainless steel. In this exemplary embodiment, the femoral stem 106 includes a stem damper 120 to reduce vibrations transmitted between the femoral stem and the femur 112 that might contribute to loosening of the femoral stem within the intramedullary canal. More specifically, the exemplary stem damper 120 is wrapped around the femoral stem 106 so that the damper interposes the stem and femur when implanted. In exemplary form, the damper 120 comprises a sleeve that may be fabricated from one or more materials that are biologically compatible and reduce vibrations transmitted between the femoral stem 106 and the femur 112 including, without limitation, silicone rubber, elastic silicone rubber, gutta percha, saline rubber, gore-tex, polystyrene, polytetrafluoroethylene, nylon, polyethylene, polyester, silk, polyethylene teraphthalate, polyvinyl alcohol-hydrogel. But this is not the only damper used as part of the first exemplary hip joint 100.

The stem damper 120 may also be inserted between a metal sleeve that is fixated with cement and/or a bone in-growth material, and the femoral stem 106. Therefore, the femoral stem 106 is locked into the metal sleeve and the damper 120 is inserted therebetween.

Figure 2:
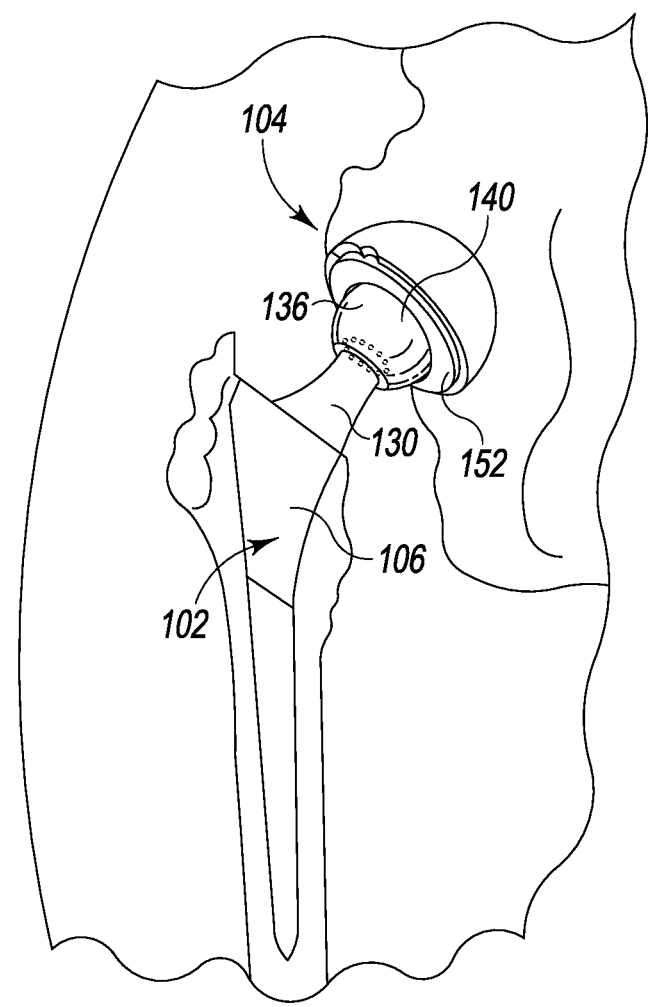
FIG. 2 is an elevated perspective view of the first exemplary prosthetic hip joint of FIG. 1, shown with a stem damper.

Referencing FIG. 2, the femoral component 102 (shown without the stem damper 120) also includes a neck 130 coupled to the femoral stem 106. In this exemplary embodiment, the neck 130 includes a frustoconical end (not shown) that engages a corresponding frustoconical cavity (not shown) formed within a ball 136. In this exemplary embodiment, the ball 136 may be fabricated from any feasible material, including metals and ceramics such as, without limitation, titanium, cobalt chromium, stainless steel, and alumina. In order to reduce vibrations transmitted between the neck 130 and the ball 136, the frustoconical end includes a damper 140 that interposes the neck and ball. The exemplary damper 140 comprises a cap that conforms to the shape of the frustoconical end. Alternatively, the damper 140 may be in the shape of a ring that circumscribes the neck 130 of the femoral component 102.

It should be noted that when the damper 140 is used, the frustoconical cavity formed within the ball 136 is large enough to accommodate both the cap and the frustoconical end. As with the foregoing damper, this exemplary damper 140 may be fabricated from one or more materials that are biologically compatible and reduce vibrations transmitted between the neck 130 and the ball 136 including, without limitation, silicone rubber, elastic silicone rubber, gutta percha, saline rubber, gore-tex, polystyrene, polytetrafluoroethylene, nylon, polyethylene, polyester, silk, polyethylene teraphthalate, polyvinyl alcohol-hydrogel. In addition to the dampers 120, 140 associated with the femoral component 102, the acetabular component 104 may also include its own dampers.

Figure 3:
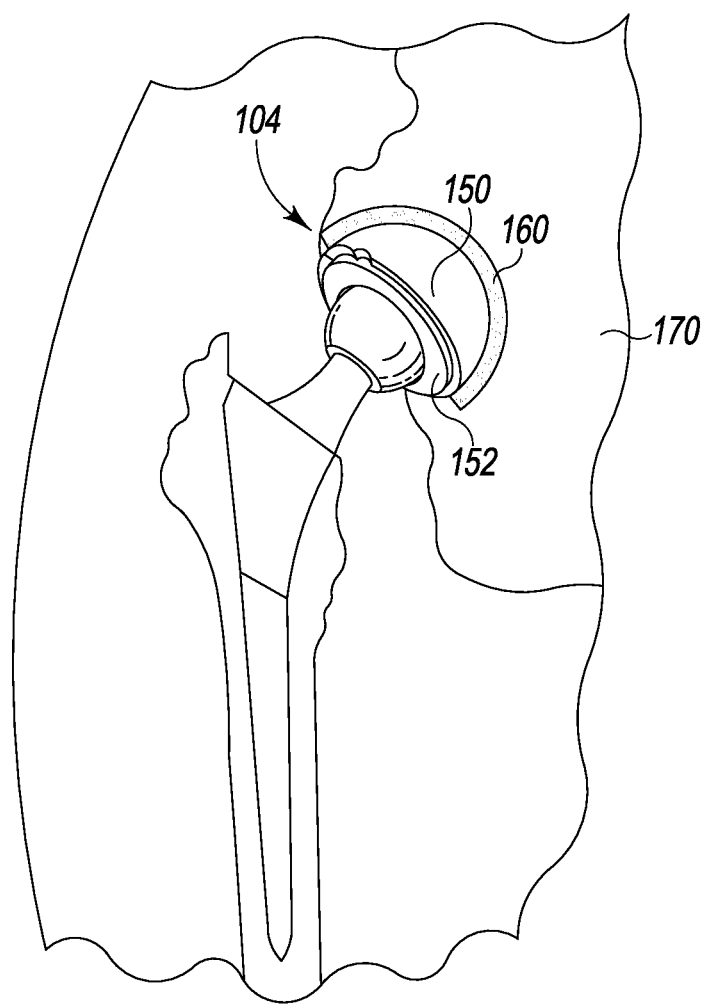
FIG. 3 is an elevated perspective view of the first exemplary prosthetic hip joint of FIG. 1, shown with an acetabular cup damper.

Referring to FIG. 3, the acetabular component 104 includes an acetabular cup 150 and an acetabular insert 152. The interior of the acetabular cup 150 includes a semispherical cavity that receives a semispherical aspect of the acetabular insert 152. The acetabular cup 150 includes a damper 160 that interposes the cup and a patient's pelvis 170. In this exemplary embodiment, the acetabular cup 150 may be fabricated from any feasible material, including metals such as, without limitation, titanium, cobalt chromium, and stainless steel. In exemplary form, the damper 160 is semicircular and is mounted to the rear of the acetabular cup 150. The overall area of this damper 150 can be very small, less than 1.0 mm² or can cover the full surface area of the acetabular cup. One or more dampers 150 may be used. By interposing the acetabular cup 150 and the pelvis 170, vibrations transmitted between the cup and pelvis are reduced. It is believed that vibrations transmitted between the cup 150 and pelvis 170 contribute to loosening of the cup and joint failure. The exemplary damper 160 may be fabricated from one or more materials that are biologically compatible and reduce vibrations transmitted between the cup 150 and the pelvis 170 including, without limitation, silicone rubber, elastic silicone rubber, gutta percha, saline rubber, gore-tex, polystyrene, polytetrafluoroethylene, nylon, polyethylene, polyester, silk, polyethylene teraphthalate, polyvinyl alcohol-hydrogel.

Figure 4:
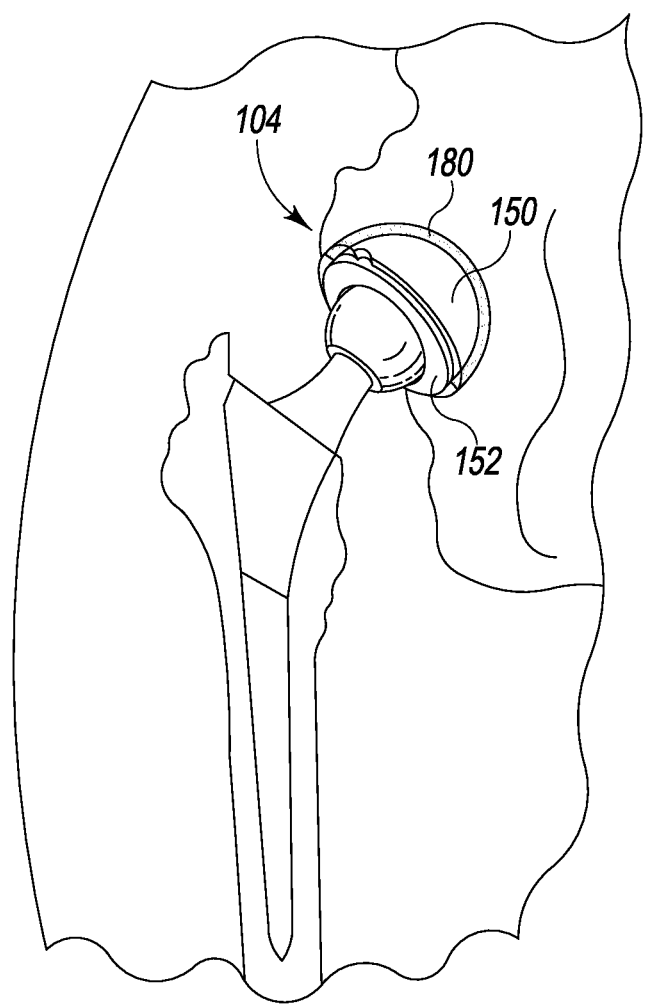
FIG. 4 is an elevated perspective view of the first exemplary prosthetic hip joint of FIG. 1, shown with an acetabular cup insert damper.

Referencing FIG. 4, in order to reduce vibrations transmitted between the acetabular component 104 and adjacent structures, a damper 180 interposes the acetabular insert 152 and the acetabular cup 150 (shown without the damper 160). In this exemplary embodiment, the acetabular insert 152 may be fabricated from any feasible material, including metals and ceramics such as, without limitation, titanium, cobalt chromium, stainless steel, and alumina. In exemplary form, the damper 180 is semicircular and is mounted to the backside of the acetabular insert 152. The overall area of this damper 180 may be very small, for example less than 1.0 mm$^2$, or can cover the full surface area of the acetabular cup. Either one or more dampers can be used. By interposing the acetabular cup 150 and the acetabular insert 152, vibrations transmitted between the cup and insert are reduced. It is believed that vibrations transmitted between the cup 150 and insert 152 contribute to loosening of the cup and joint failure. The exemplary damper 180 may be fabricated from one or more materials that are biologically compatible and reduce vibrations transmitted between the cup 150 and the insert 152 including, without limitation, silicone rubber, elastic silicone rubber, gutta percha, saline rubber, gore-tex, polystyrene, polytetrafluoroethylene, nylon, polyethylene, polyester, silk, polyethylene teraphthalate, polyvinyl alcohol-hydrogel.

The exemplary vibrational dampers 120, 140, 160, 180 may be utilized when the resonant frequencies of adjacent components are not the same. Due to the presence of hip separation and sliding of the femoral head within the acetabular cup, impulse loads and vibrational energy are transmitted and propagated throughout the hip joint.

The natural or resonant frequency of an object is the frequency at which that object will vibrate freely. If a varying force with a frequency equal to the natural frequency is applied to an object, the vibrations can become violent, a phenomenon known as resonance. Resonance is the buildup of large vibration amplitude that occurs when a structure or an object is excited at its natural frequency. Resonance can be either desirable or undesirable. In the context of acoustic resonance, a desirable resonance is exhibited by musical instruments. Conversely, undesirable resonance can lead to mechanical failures resulting in bridges collapsing and fracturing of aircraft wings.

The quality of the vibration and propagation of the vibration produced by a vibrating object is dependent upon the natural frequencies of the vibrational waves produced by the object. Some objects tend to vibrate at a single frequency, while other objects vibrate and produce more complex waves with a set of frequencies. If converted to a sound, these objects create sounds that could be described as noise. The actual frequency at which an object will vibrate at is determined by the following relationship: frequency=speed/wavelength. The inventor has found it beneficial to determine the natural frequency of THA implantable components and secondary structures (e.g., bone cement) to mitigate undesirable resonance.

A first exemplary method for determining resonant frequency of a component or tissue includes excitation of the component or tissue using, for example a speaker, amplifying different frequencies. For example, an accelerometer may be used on bones, attaching one tri-axial accelerometer rigidly to the bone and then when excited, the acceleration signal, once filtered, is used to determine the natural frequency of the bone.

Also, a Fourier Series may be used to determine the frequency of an object in question. The Fourier Series reveals how a mathematical series of sine and cosine terms can be used to analyze a waveform. Once the Fourier Series is written for a waveform then the components of the series completely describe the frequency content of the waveform. There are four conditions that must be met in order for the Fourier Series to be useful.

1. The waveform must be periodic. This waveform must repeat time for a Fourier Series to exist.
2. If the function has discontinuities, their number must be finite in any period.
3. The function must contain a finite number of maxima and minima during any period.
4. The function must be absolutely integrable in any period; that is, $$\int_0^T |x(t)| dt | \infty$$

Where x(t) describes that function.
The Fourier Series, in general is:

$$x(t) = a_0 + a_1 \cos \omega_0 t + a_2 \cos 2\omega_0 t + \ldots a_n \cos n\omega_0 t + \ldots b_1 \sin \omega_0 t + b_2 \sin 2\omega_0 t + \ldots b_n \sin n\omega_0 t \ldots$$

where the quantity $\omega_0$ is generally measured in radians per second, and is referred to as the circular frequency. Since the motion repeats itself in $2\pi$ radians, then $$\omega_0 = \frac{2\pi}{\tau} = 2\pi f_0,$$

where $\tau$ and $f$ are the period and frequency of the harmonic motion, usually measured in second and cycles per second, respectively.

The Fourier Series can also be written in a more general form as:

$$x(t) = a_0 + \sum_{n=1}^{\infty} [(a_n) \cos n\omega_0 t + b_n \sin n\omega_0 t].$$

First, $\omega_0$ is found from the period of x (t) and is equal to $$2\pi/T (\text{also}, f_0 = 1/T).$$

The $a_0$ coefficient is the DC (direct current) term and is equal to the average value of x(t) over one period. This is determined by $$a_0 = \frac{1}{T} \int_0^T x(t) dt.$$

The remaining coefficients, $a_n$ and $b_n$, are evaluated for n−1, 2, 3, . . . by $$a_n = \frac{2}{T} \int_0^T x(t) \cos n\omega_0 t / dt,$$

and $$b_n = \frac{2}{T} \int_0^T x(t) \sin n\omega_0 t / dt.$$

Those skilled in the art may be familiar with numerous other methods that may be used to determine resonant frequencies for bodily tissue, implantable components, and secondary structures.

When a patient experiences hip separation, once the femoral head slides back into the acetabular cup, an impulse load is been generated, which results in vibration being propagated throughout the hip joint. If these vibrations are at or near resonant frequencies of bone, the implanted components, and/or secondary structures, detrimental resonance can lead to premature failure. To reduce this premature failure and wear, vibrational dampers are positioned to absorb vibrations between adjacent components.

In order to determine whether vibrational dampers 120, 140, 160, 180 may be preferred, the exemplary orthopedic hip joint components may be tested to determine their respective resonant frequencies. When two or more hip joint components have the same or similar resonant frequencies, one or more vibrational dampers 120, 140, 160, 180 may be utilized. It is to be understood that testing of orthopedic components is not required as a prerequisite for including vibrational dampers 120, 140, 160, 180 as part of an orthopedic hip joint.

Figure 5:
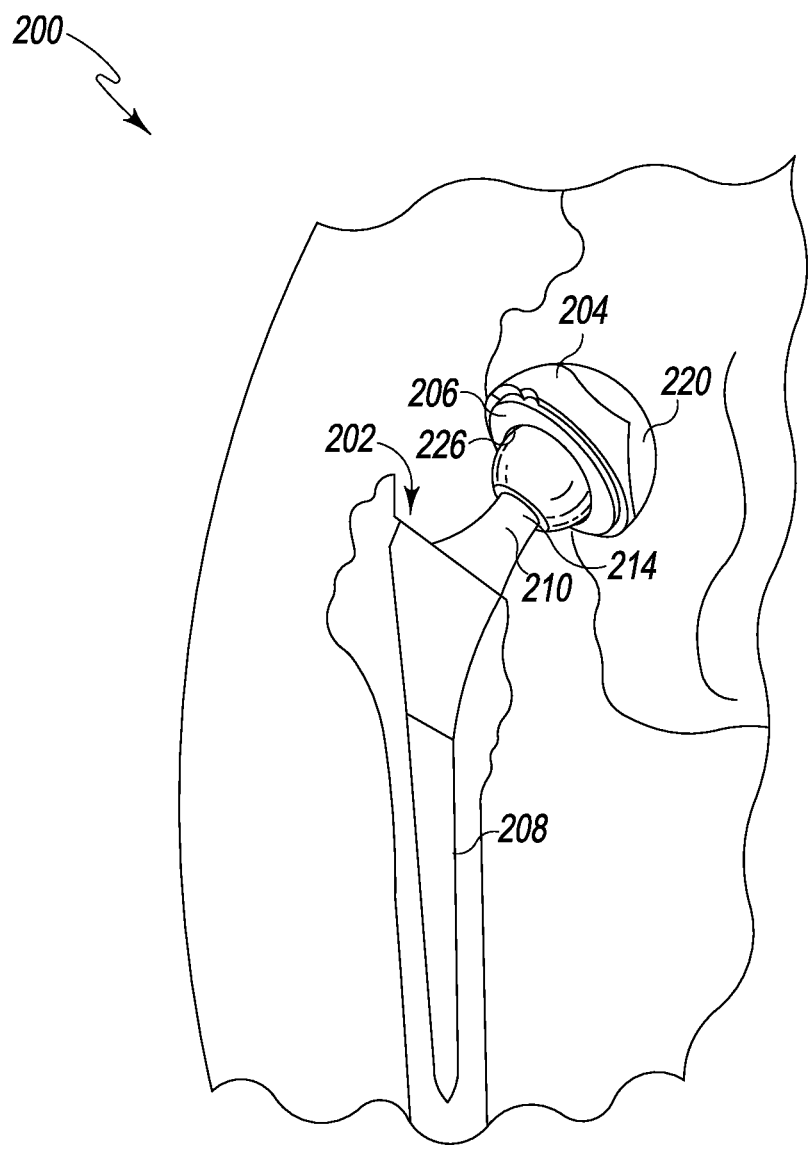
FIG. 5 is an elevated perspective view of a second exemplary prosthetic hip joint in accordance with the instant disclosure, shown with a ghost image of the patient's natural anatomy.

Referring to FIG. 5, an exemplary hip implant assembly 200 includes a femoral component 202, an acetabular cup 204, and an acetabular insert 206. Due to the presence of high bearing surface forces in total hip arthroplasty, the femoral component 202 may be totally or partially fabricated using highly magnetic materials that work in conjunction with highly magnetic materials that may be used to fabricate the acetabular cup 204 and/or acetabular insert 206 to reduce lower hip joint forces and/or hip separation.

In this exemplary embodiment, the femoral component 202 includes a femoral stem 208 that is adapted to be implanted into the femoral intramedullary canal after the femoral bone has been properly resected. Extending proximally from the femoral stem 208 is an integral neck 210 that includes a threaded or conical end (not shown) adapted to receive a femoral ball 214. The femoral ball 214 is fabricated to include a biologically compatible metallic coating (e.g., stainless steel, titanium, titanium alloy), which surrounds a neodymium magnetic core or other ferrous core. Alternatively, the femoral ball 214 may be fabricated to include one or more permanent magnets (e.g., neodymium magnet) embedded within a biologically compatible metal substrate (e.g., stainless steel, titanium, titanium alloy). In either circumstance, the magnetic field generated by the femoral ball 214 represents a magnetic North Pole, which is pulled toward any magnetic South Pole.

In order to retard dislocation of the femoral ball 214 from the acetabular insert 206, the acetabular cup 204 includes a biologically compatible metallic coating 220 (e.g., stainless steel, titanium, titanium alloy), which surrounds a ferrous core. Alternatively, the acetabular cup 204 may be fabricated to include one or more magnets embedded within a biologically compatible metal substrate (e.g., stainless steel, titanium, titanium alloy). In either circumstance, the magnetic field generated by the acetabular cup 204 represents a magnetic South Pole. Because the force between the North Pole and the South Pole is inversely proportional to the square of the distance between the magnetized surfaces, it is important to reduce the distances between the Poles.

Figure 6:
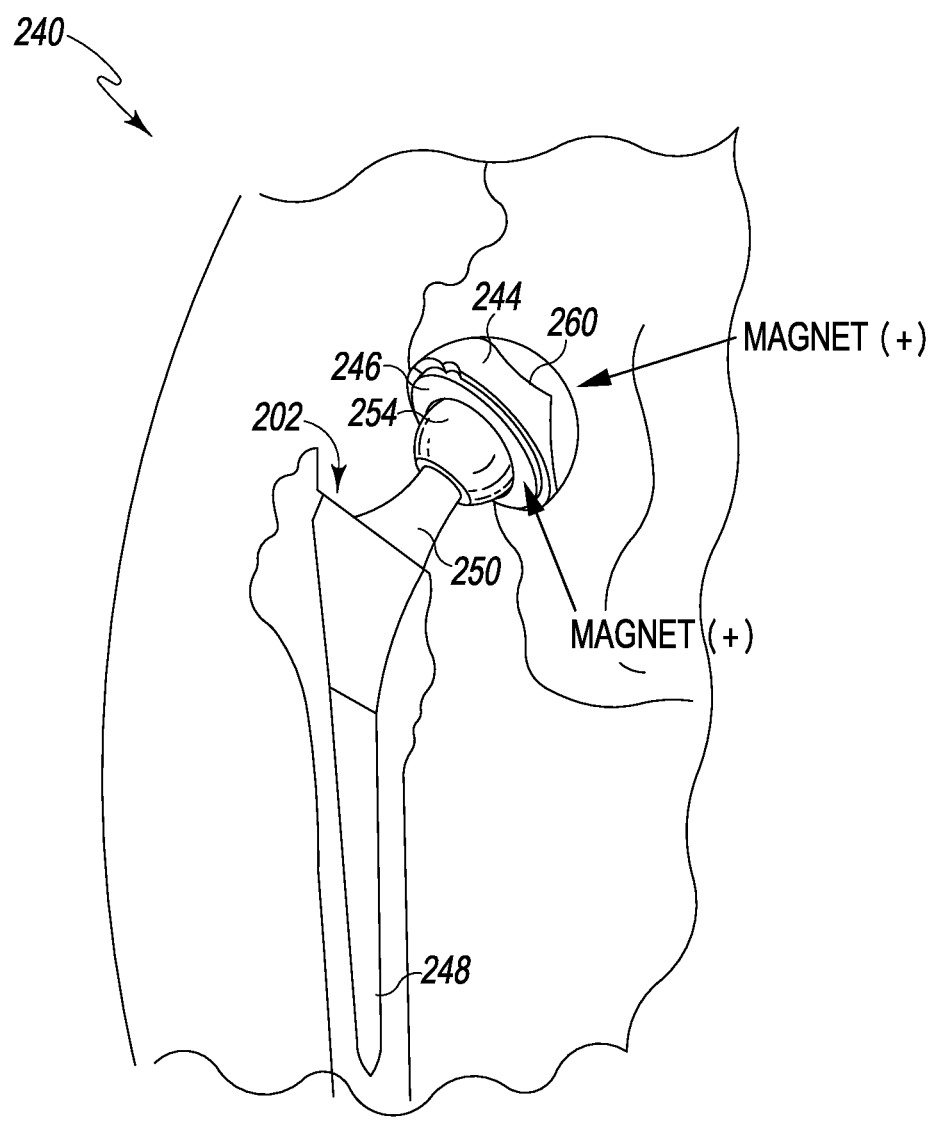
FIG. 6 is an elevated perspective view of an alternate exemplary prosthetic hip joint, shown with indicia indicating like magnetic fields to repel certain components.

In order to reduce the distances between the poles, the acetabular insert 206 may be fabricated using two considerations. First, the acetabular insert 206 may be fabricated to have a minimal thickness, thereby reducing the distance between the femoral ball 214 and the acetabular cup 204. Alternatively, or in addition, the acetabular insert 206 may itself house one or more magnets oriented so that the North Pole faces toward the acetabular cup 204 and the South Pole faces toward the femoral ball 214. In exemplary form, an acetabular insert 206 includes a bowl-shaped neodymium magnetic core or other ferrous magnetic core. This core is then overmolded or encapsulated in a biologically compatible polymer or ceramic to form a capsule 226 comprising the bearing surface of the cup 204. In exemplary form, the mean thickness of the capsule 226 is between 0.1 mm to 20 mm Referring to FIG. 6, an alternate exemplary hip implant assembly 240 includes a femoral component 242, an acetabular cup 244, and an acetabular insert 246. The femoral component 242 includes a femoral stem 248 having an integral neck 250 that includes a threaded or conical end (not shown) adapted to receive a femoral ball 254. The femoral ball 254 is fabricated to include a biologically compatible metallic coating (e.g., stainless steel, titanium, titanium alloy), which surrounds a neodymium magnetic core or other ferrous core. Alternatively, the femoral ball 254 may be fabricated to include one or more permanent magnets (e.g., neodymium magnet) embedded within a biologically compatible metal substrate (e.g., stainless steel, titanium, titanium alloy). In either circumstance, the magnetic field generated by the femoral ball 254 represents a magnetic North Pole.

In order to decrease impact forces between the femoral component 242 and the acetabular components 244, 246, the magnetic field of the femoral component and the acetabular components may be the same. Specifically, at least one of the acetabular insert 246 and the acetabular cup 244 includes a biologically compatible metallic coating 260 (e.g., stainless steel, titanium, titanium alloy), which surrounds a ferrous core. Alternatively, the acetabular cup 244 and acetabular insert 246 may be fabricated to include one or more magnets embedded within a biologically compatible metal substrate (e.g., stainless steel, titanium, titanium alloy). In either circumstance, the magnetic field generated by the acetabular cup 244 and acetabular insert 246 represents a magnetic North Pole. Because the North Poles of the femoral component 242 and the acetabular components 244, 246 operate to repel one another, the impact forces between the femoral component and the acetabular components may be reduced.

Figure 7:
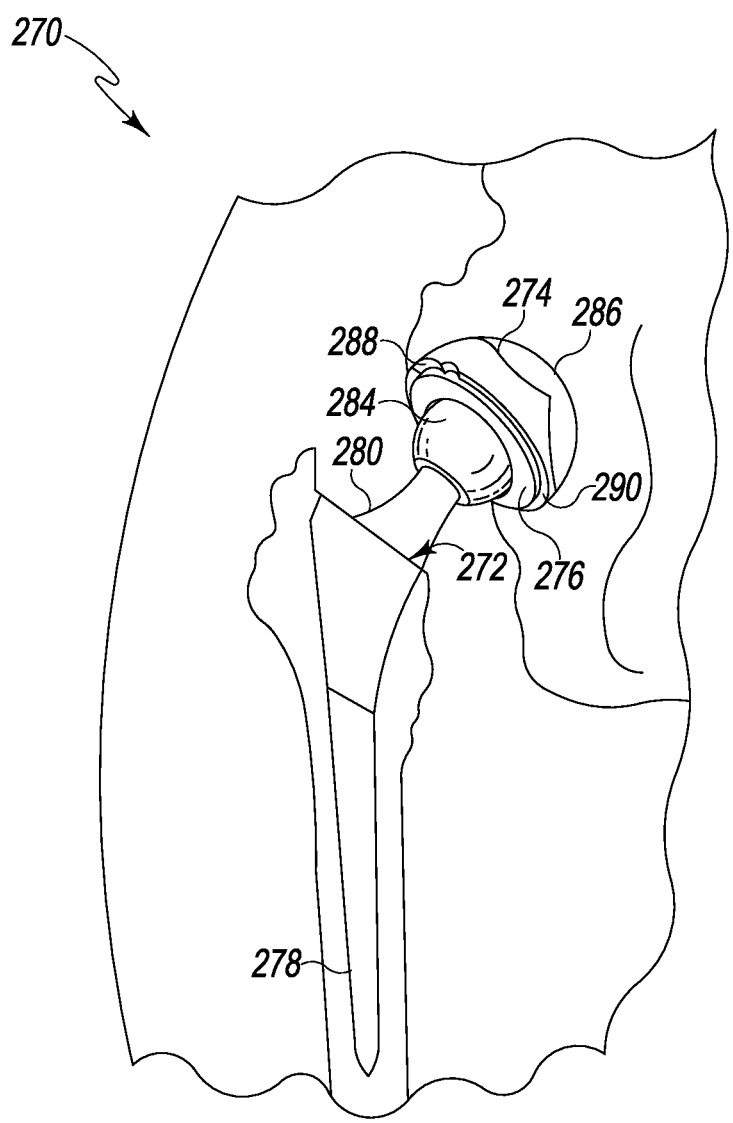
FIG. 7 is an elevated perspective view of another alternate exemplary prosthetic hip joint, shown with a ghost image of the patient's natural anatomy.

Turning to FIG. 7, another alternate exemplary hip implant assembly 270 includes a femoral component 272, an acetabular cup 274, and an acetabular insert 276. The femoral component 272 includes a femoral stem 278 having an integral neck 280 that includes a threaded or conical end (not shown) adapted to receive a femoral ball 284. In this embodiment, the femoral ball 284 and the most proximal aspect 286 of the acetabular cup 274 (farthest from the femoral shaft) both have a positive polarity (i.e., North Pole), but a distal medial 288 and distal lateral aspect 290 of the acetabular cup 274 have a negative polarity (i.e., South Pole). In exemplary form, the positive-positive polarity interaction operates to decrease the compressive forces during weight-bearing activity, while the positive-negative polarity interaction resists dislocation and femoral ball separation.

Figure 8:
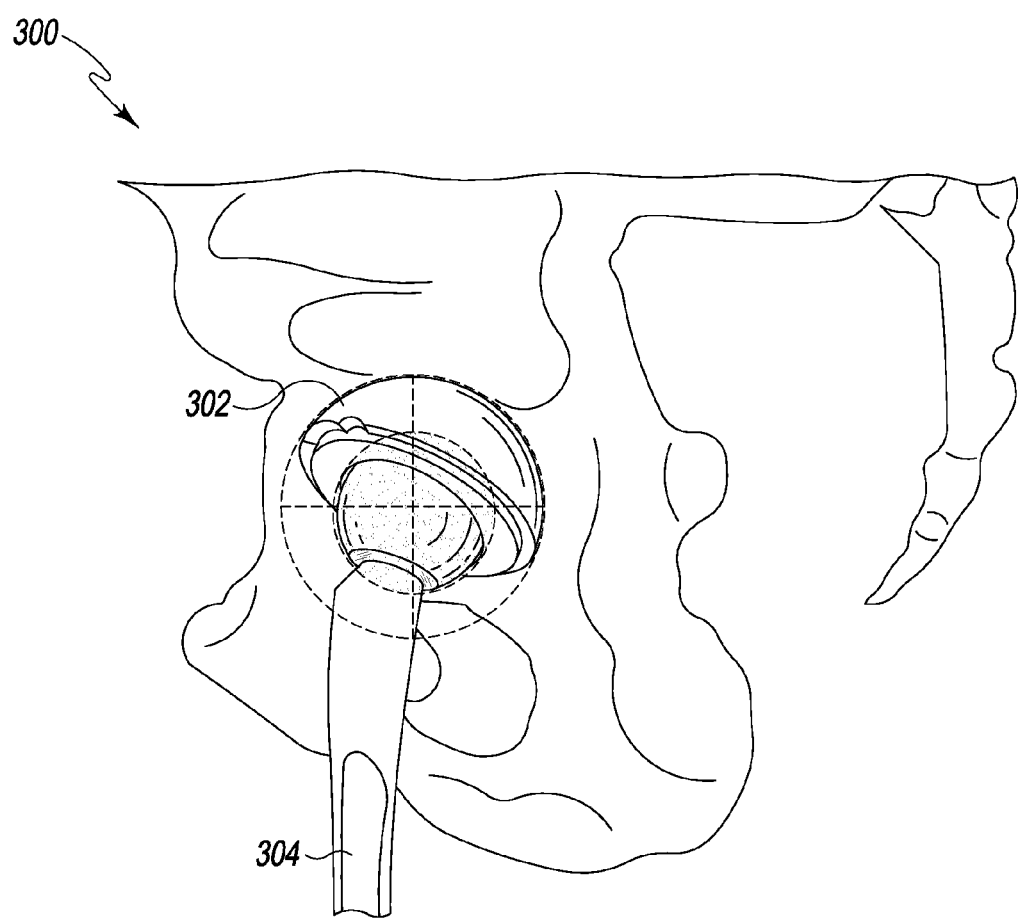
FIG. 8 is a profile view of a human pelvis and proximal femur showing concentric anatomical spheres.
Figure 9:
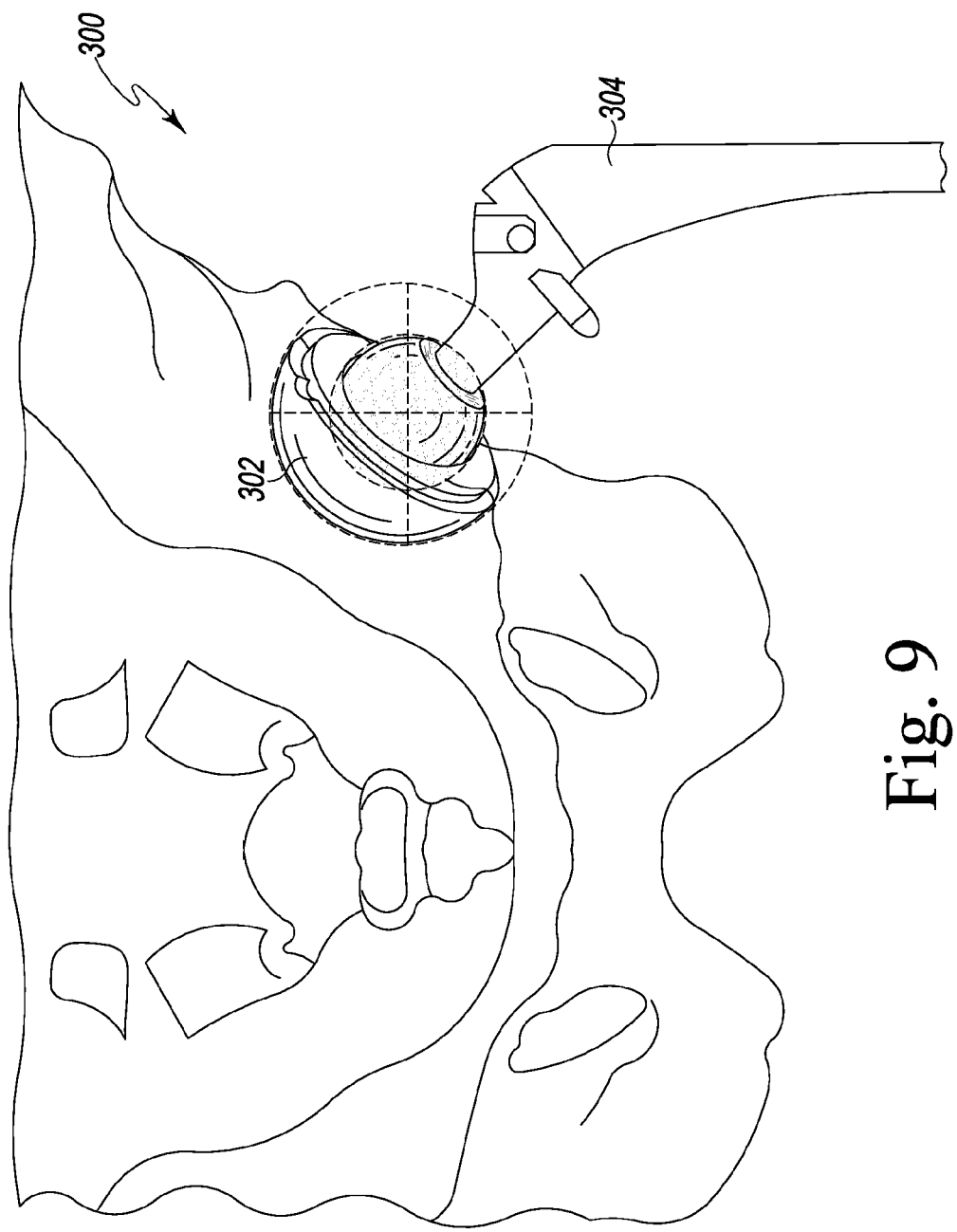
FIG. 9 is a frontal view of a human pelvis and proximal femur showing concentric anatomical spheres.
Figure 10:
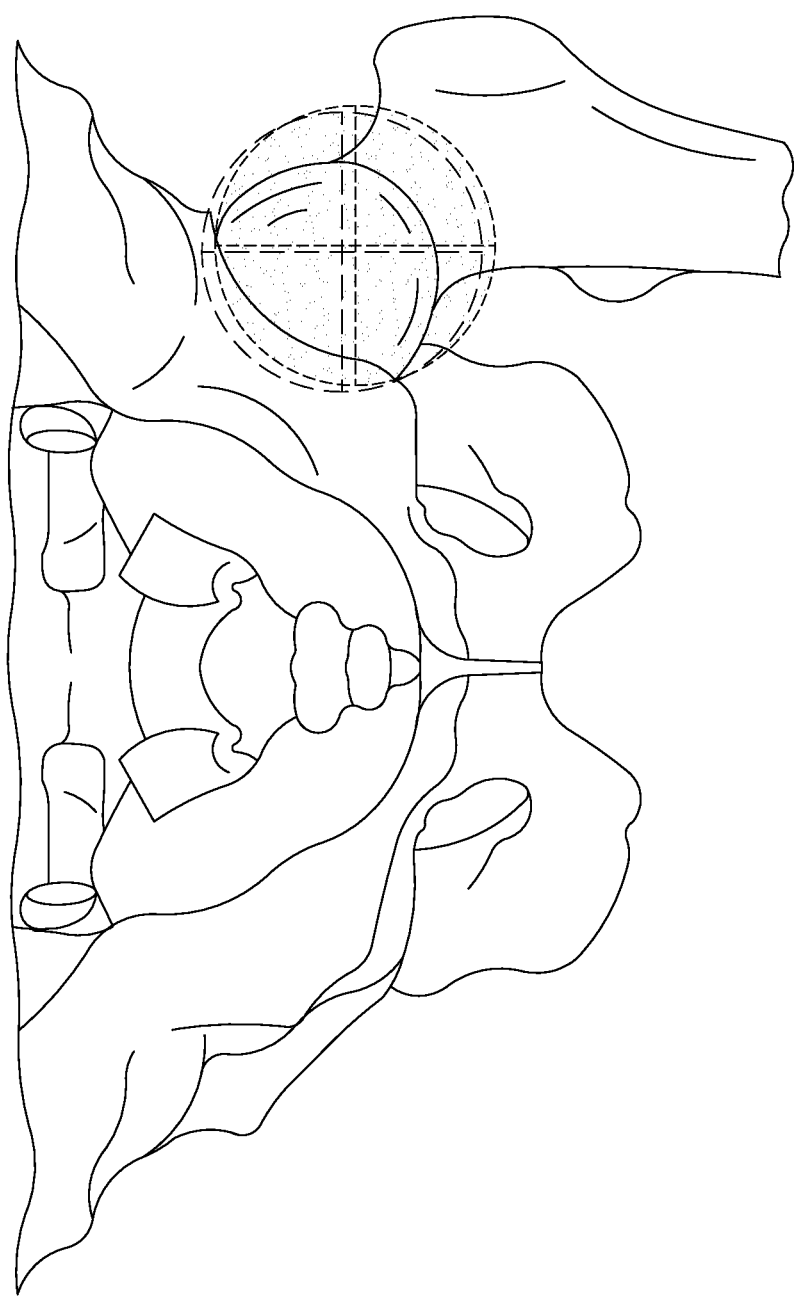
FIG. 10 is a frontal view of a human pelvis and proximal femur showing non-concentric anatomical spheres.
Figure 11:
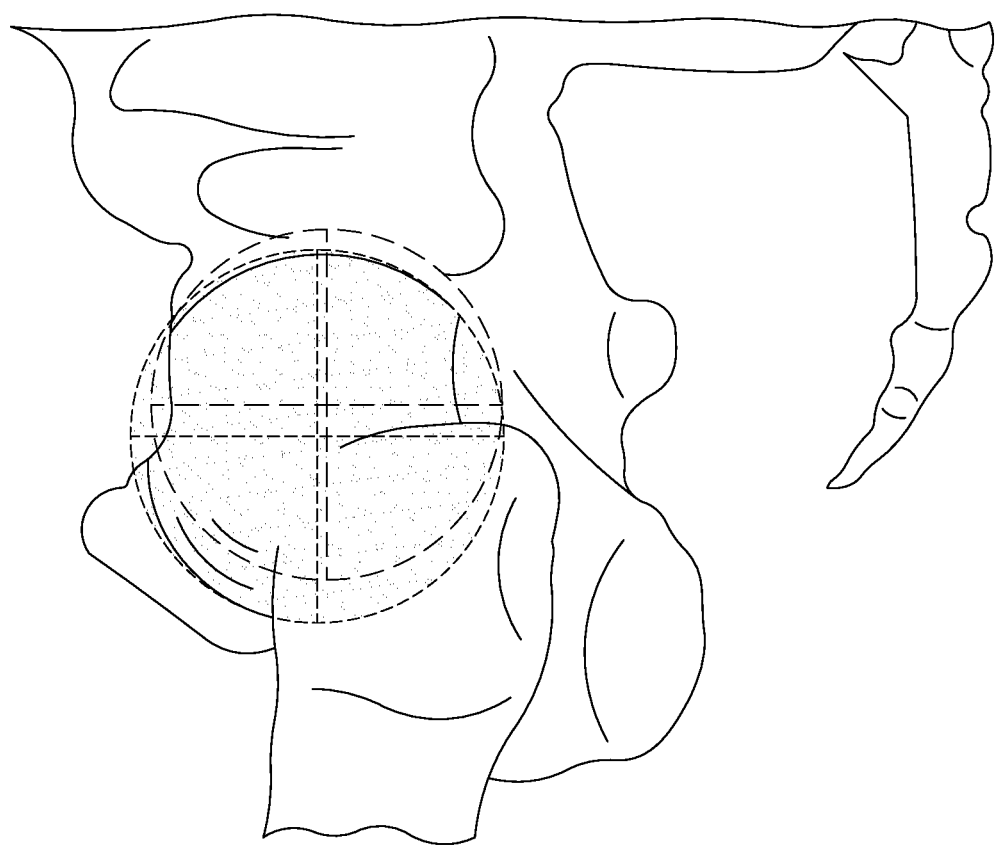
FIG. 11 is a profile view of a human pelvis and proximal femur showing non-concentric anatomical spheres.
Figure 12:
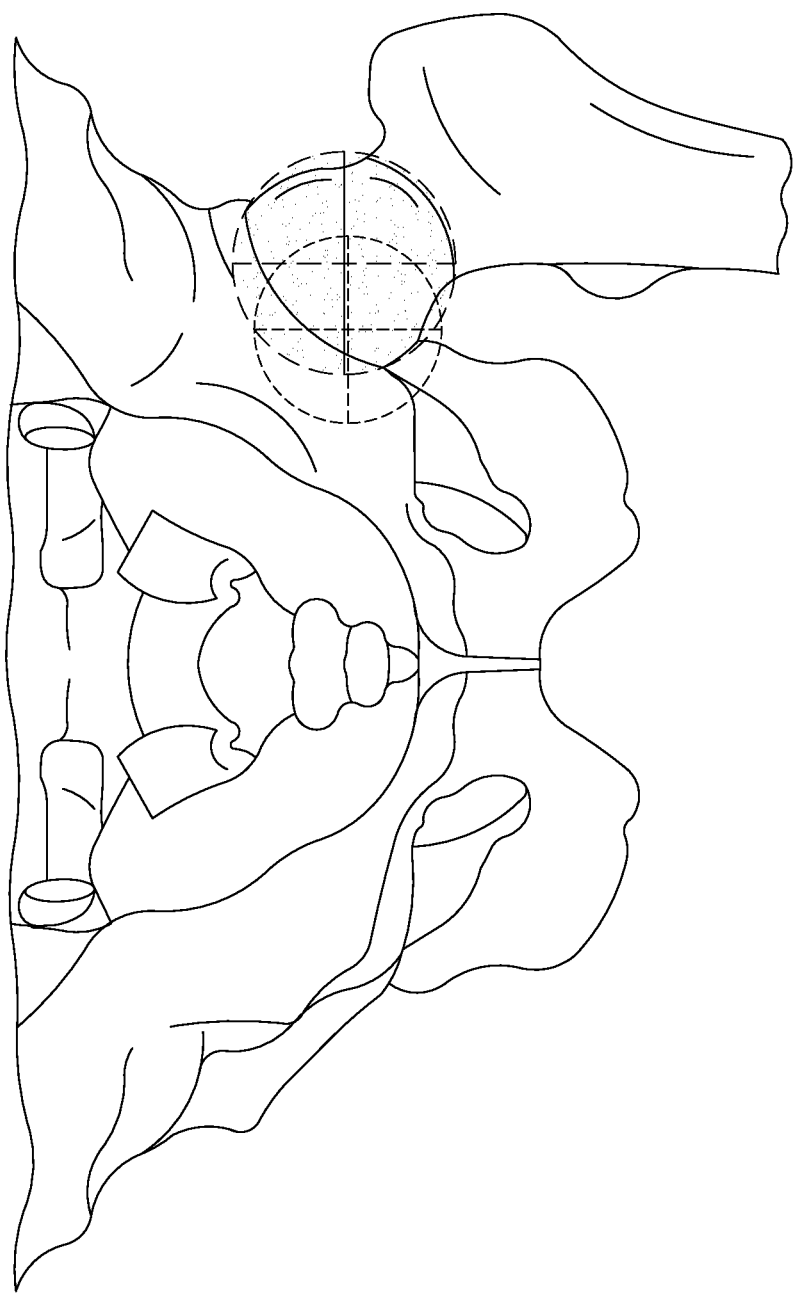
FIG. 12 is a frontal view of a human pelvis and proximal femur showing non-concentric anatomical spheres.
Figure 13:
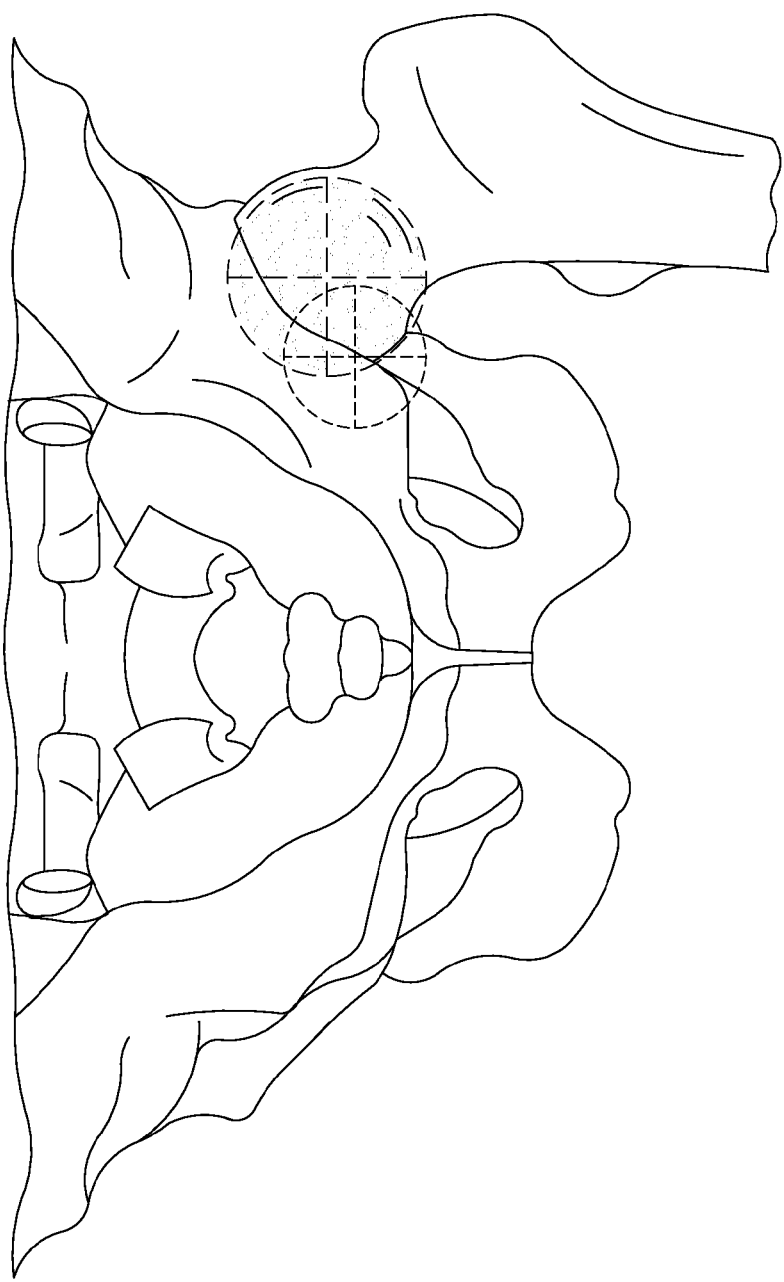
FIG. 13 is a frontal view of a human pelvis and proximal femur showing non-concentric anatomical spheres.
Figure 14:
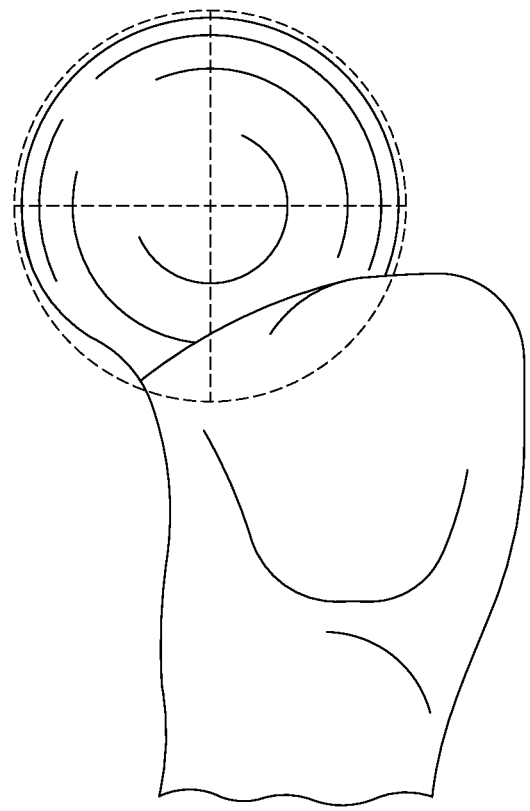
FIG. 14 is a profile view of a human proximal femur showing an anatomical sphere that is correctly selected.
Figure 15:
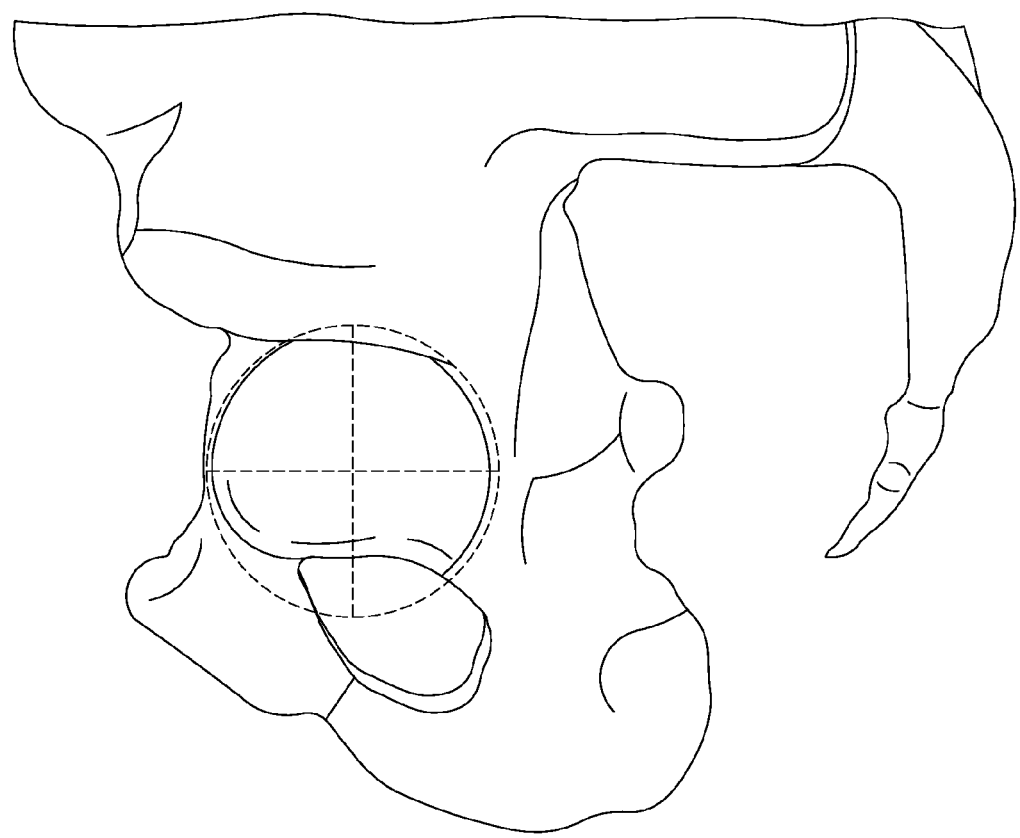
FIG. 15 is a profile view of a human pelvis showing an anatomical sphere that is correctly selected.
Figure 16:
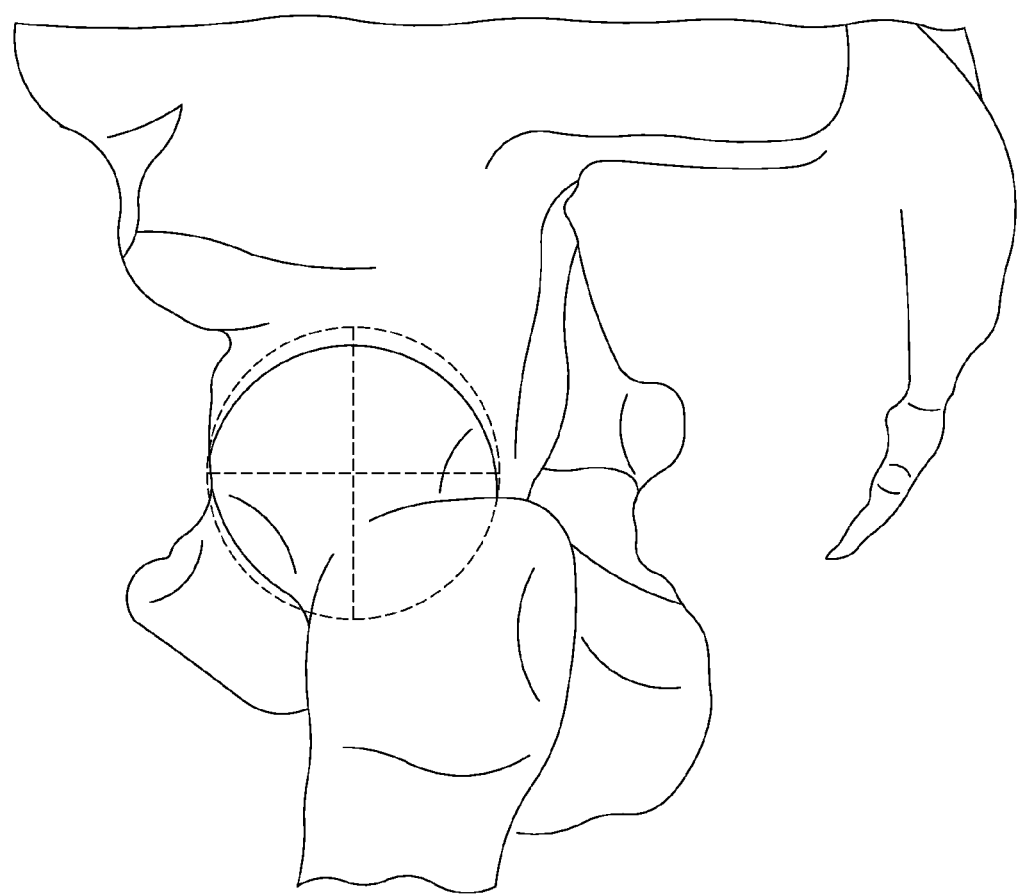
FIG. 16 is a profile view of a human pelvis and proximal femur showing a common anatomical sphere center.
Figure 17:
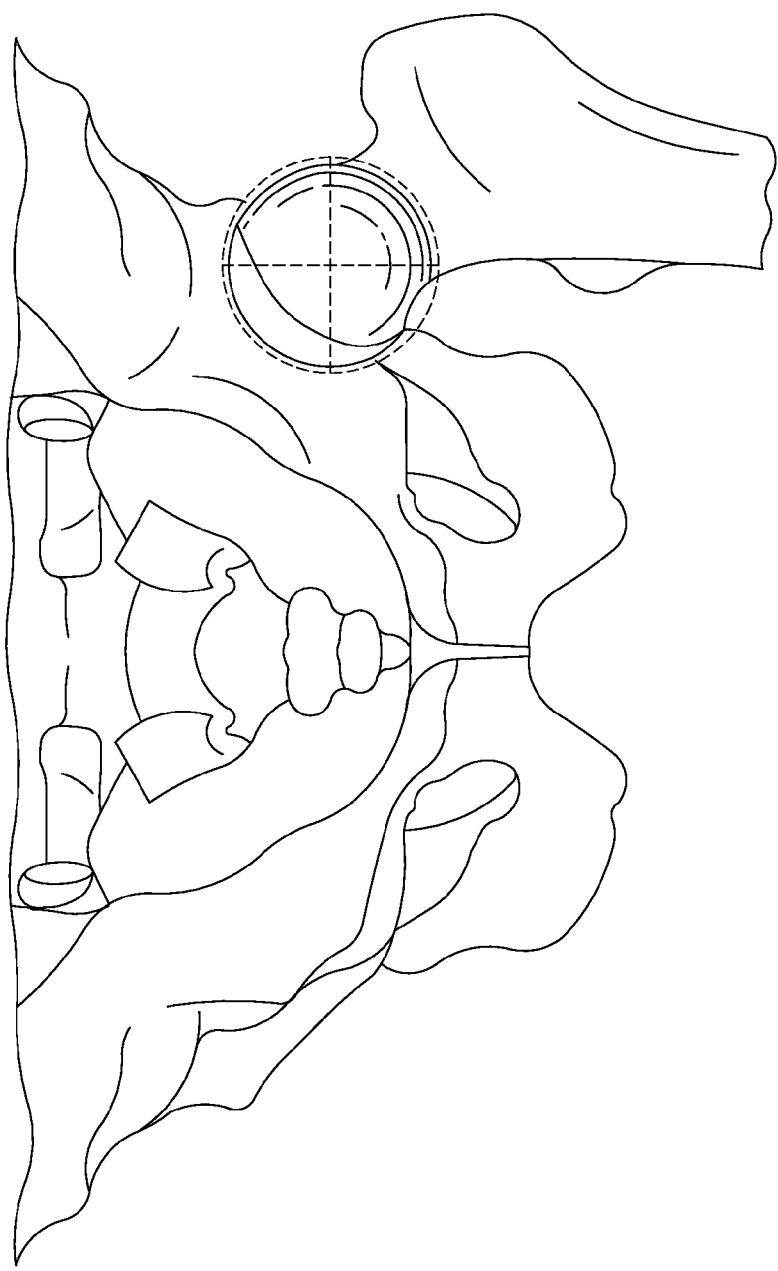
FIG. 17 is a frontal view of a human pelvis and proximal femur showing a common anatomical sphere center.

Referencing FIGS. 8 and 9, an additional exemplary orthopedic hip joint 300 comprises a cup component 302 and a femoral component 304 having concentric spheres. More specifically, the patient's anatomy is prepared to ensure both the cup component 302 and a femoral component 304 have a common spherical center with respect to the acetabulum.

Referring to FIGS. 10-13, although it has been stated in numerous publications that the human hip is a revolute joint, whereas only three sequential rotations are present, the actual shapes of the acetabulum and femoral head of the femur are not pure spheres. In fact, the position of numerous exterior points on the acetabulum and the femoral head can be recorded and computer algorithms applied to these points to create spheres whose surface best correlates with the recorded points. In a study conducted by the inventor, it was determined that numerous spheres can be derived using sets of points on the surface of the acetabulum and the femoral head. Therefore, in a conservative sense, using sets of points on the acetabulum and on the femoral head, one could easily derive at least fifty spheres for each of the acetabulum and the femoral head that at least partially correlated with the recorded points (i.e., at least some of the recorded points would comprise an exterior point on a sphere). Therefore, if fifty spheres for the acetabulum and fifty spheres for the femoral head were chosen, this would result in twenty-five hundred combinations of spheres. But the inventor has determined that the correct combination of spheres is a concentric combination derived from the bearing surface interfaces of the acetabulum and femoral head during walking, and is derived from the cartilage surface within the acetabulum and the cartilage surface on the femoral head.

Referring back to FIGS. 8 and 9, in order to design the cup component 302 and the femoral component 304, a kinematic analysis is conducted for the intended recipient of the orthopedic hip joint 300. This kinematic analysis defines points on recipient's natural femoral head in contact with the acetabulum and corresponding points on the acetabulum in contact with the femoral head.

An exemplary kinematic analysis is performed to determine these spheres while the joint is under dynamic, weight-bearing, in vivo conditions. During normal gait motion, these spheres maintain concentricity. Therefore, with present imaging technology, fluoroscopy is an exemplary method of use. But other imaging modalities, like ultrasound could be used to perform the kinematic analysis. Under fluoroscopic surveillance, the patient performs normal walking. Then, the patient undergoes a second clinical imaging test using CT, MRI, or ultrasound (other technologies could also be used). In the context of a CT scan, the scanned slices of the joint are used to create a three dimensional (3D) model of the patient's pelvis and femoral bones. Then, these 3D bones are overlaid onto the two dimensional fluoroscopic images. Once all of the fluoroscopic images, or a selected chosen few fluoroscopic images are converted to 3D, the patient's hip motion may be viewed in any chosen plane. Using a collision detection analysis, the point of the femoral head in contact with the pelvis and the points of the pelvis in contact with the femoral head are determined and mapped sequentially.

If one does not have the capability to determine the correct points on the acetabulum and the femoral head using the above mentioned kinematic analysis, one may alternatively use trial and error to derive the location of the concentric spheres by placing different sizes of spheres in different locations relative to the acetabulum and the femoral head for each patient until the spheres are concentric in multiple planes. Once the anatomical concentricity is established for that particular patient, the location can be mapped and relocated during surgery to ensure that the spherical centers of the implanted components are matched to the anatomical spherical centers.

Referring to FIGS. 14-17, spheres are superimposed onto the points that best conform to the mapped points on the pelvis and femoral head to create individual spheres. It is important to note that these spheres may be derived using the boney anatomy or on the cartilage. The correct sphere for each patient may be dependent on the quality of cartilage and/or the concentricity of the two spheres.

After the spheres are defined, the location of the center of these spheres is defined and used a target origin (or center) for the spheres of the implanted femoral head and the acetabular cup. The center of two derived spheres can be defined quite easily using numerous software packages and/or using a mathematical approach. It is important to then map out the location of the patient's anatomical sphere centers with respect to boney landmarks. The center of the chosen pelvis sphere needs to be tracked with respect to boney landmarks on the pelvis and the center of the femoral head sphere needs to be tracked with respect to boney landmarks on the femur bone.

Preparation of the bones to receive prosthetic components should be done with respect to maintaining the patient's anatomical spheres. Therefore, after the bones have been prepared for the implanted components, the implanted components are implanted to maintain these spherical centers. Alternatively, a surgical navigation system or an imaging modality may be used to locate the patient's spherical center(s) and ensure that the implanted components are implanted to maintain the spherical center(s).

Unlike the foregoing exemplary embodiment that is patient-specific, cost considerations may require a finite set of implant components that differ in size from one another. This finite set of implant components may include gender and ethnicity considerations, depending upon the population utilized to model the implant components. By doing so, it is anticipated that there will be more than three acetabulum spheres (presently, patients normally received a femoral head having either a 28 or 32 or 36 mm sizing) needed to fit everyone requiring a TKA. Then, knowing the proper acetabulum sphere sizes, the center of these spheres is defined and used to develop proper sizing for the acetabular cup, cup insert, and femoral ball/head components. Proper sizes for the acetabular cup, cup insert, and femoral ball/head are designed to maintain spherical concentricity throughout normal gait.

Maintaining proper spherical centers also leads to the femoral stem being implanted properly so that the center of femoral head sphere is located at the origin of the acetabular cup sphere. The centers for both of these spheres (head and cup) are thus coincident with the anatomical center of the acetabulum sphere taking into account the cartilage surface.

It is understood that in most sizing analysis of implants, if a bell curve is used, there is a set number of sizes that will include 90% of the subjects requiring that type of implant. Unfortunately, in a total hip arthroplasty (THA), unlike other prosthesis, such as a total knee arthroplasty (TKA), all patients receive one of three sizes. Therefore, in a perfect world, the best outcome would be that 30% of the patients receive a THA implant that may maintain concentric spheres. Unfortunately, this is not the case because a slight misalignment of the implanted components will lead to the pelvis and femoral head spheres not being concentric. Therefore, it is important to understand and derive proper spheres that allow at least 90% of the population to receive a THA with the ability to maintain their anatomic sphere concentricity. Using an exemplary kinematic analysis as discussed previously herein, one determines spherical sizes for the pelvis and spherical sizes for the femoral head that fit a predetermined percentage of patients. Although present day sizes are only 28, 32 and 36 mm femoral heads that are then mated with the acetabular cup liner, this analysis may reveal that 10 to 12 sizes of femoral heads and acetabular cup liners should be produced so that 90% of the subjects under the bell curve could receive proper femoral head and acetabular cup sizes that maintain their spherical concentricity. These sizes may not be whole numbers, but rather decimal numbers. Again, it is important that each patient receive a femoral head and acetabular component that maintains spherical concentricity after THA implantation. Using the wrong femoral head and/or acetabular cup insert size leads to these implanted spheres not being concentric with the patient's anatomical spherical concentricity. This improper sizing may lead to the inducement of shear forces, further leading to femoral head separation and/or dislocation.

The shape of present day femoral stems is not able to accommodate spherical concentricity due to limited options. Therefore, it is understood that multiple neck lengths and neck angles with respect to the femoral stem may be available to the surgeon. Therefore, once the anatomical spherical center is found, it may be relocated using the spherical centers of the implanted components by utilizing various stem neck options. This may be of particular concern in case where a surgeon removes too much or not enough bone and/or the femoral cut and/or the stem is fixated into the femoral bone at an offset angle.

Figure 18:
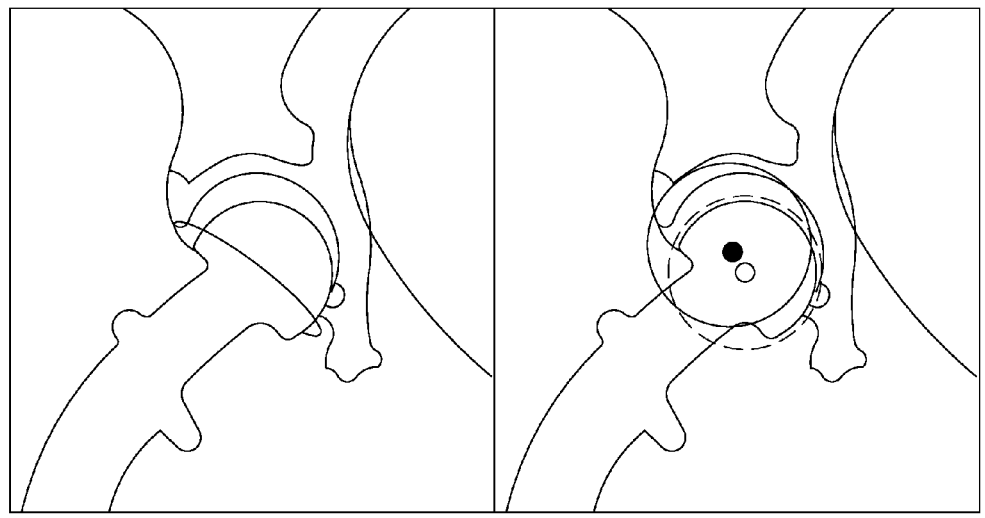
FIG. 18 is an X-ray image of a preexisting hip implant failing to have concentric centers.
Figure 19:
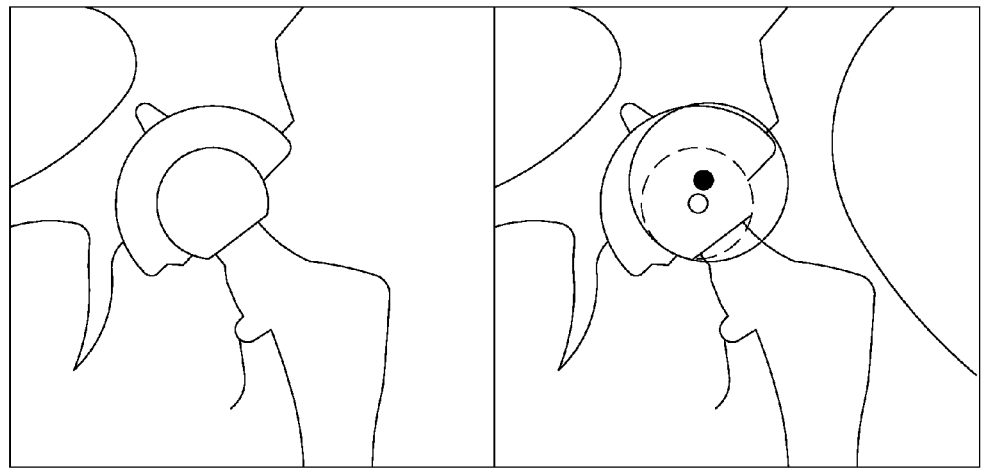
FIG. 19 is another X-ray image of a different preexisting hip implant failing to have concentric centers.

Referring to FIGS. 18 and 19, femoral head separation in present-day THA is induced by the acetabular cup and the femoral head being implanted in a position and/or orientation that does not coincide with the proper spherical center of patient. Thus, this misplacement of these components induce shear forces so that the patient's muscular structure attempts to realign the prosthetic components to the patient's proper anatomical spherical center. FIGS. 18 and 19 show examples of present-day implants that were implanted and how these implants have not maintained the patient's proper anatomical spherical center. The dotted circle represents the implanted femoral head sphere for this patient. The half dot represents the center of this implanted femoral head sphere. The solid circle represents the anatomical acetabulum sphere derived from the weight-bearing contact points, on the cartilage, for this subject during normal walking. The solid dot represents the center of this anatomical based acetabulum sphere. Unfortunately, after implantation, the femoral head is no longer rotating around this patient's anatomical spherical center. But the patient's muscular structure around the hip joint is wed to this anatomical spherical center and attempts to rotate the hip implant around this patient's anatomical spherical center. Because the patient's anatomical sphere center and prosthetic sphere centers (for ball and socket) are not coincident, shear forces are created in the implanted hip joint that lead to hip separation and/or hip dislocation.

Figure 20:
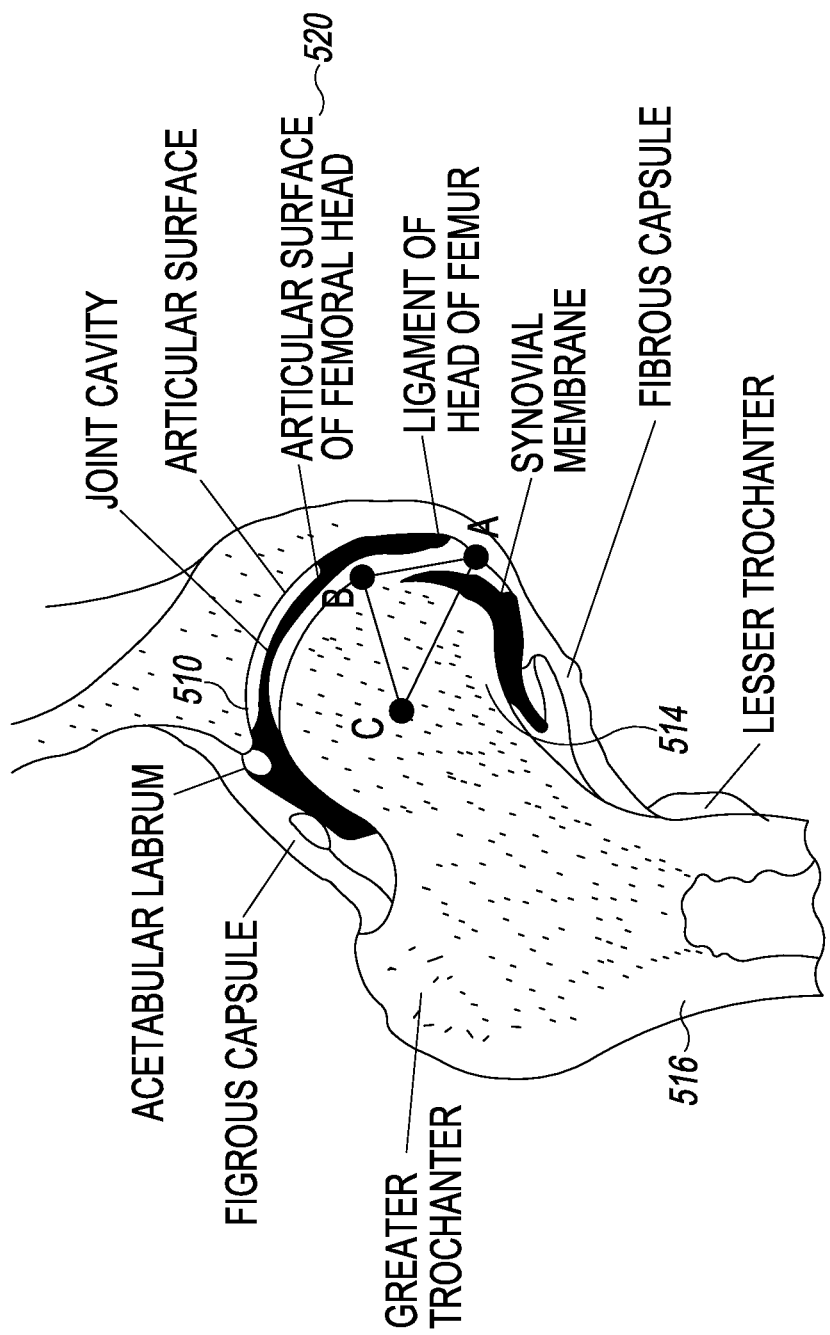
FIG. 20 is a diagram of the proximal femur and acetabulum of the pelvis.
Figure 21:
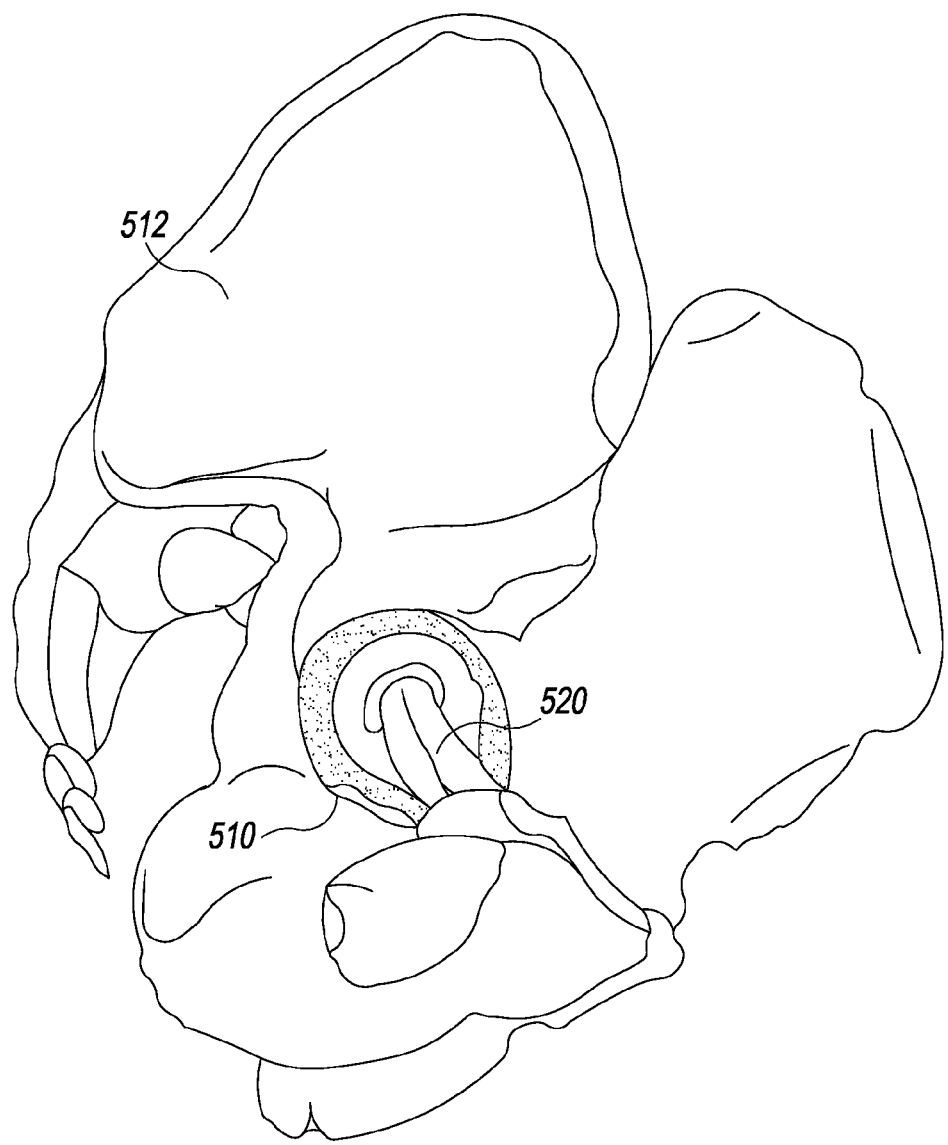
FIG. 21 is a profile view of a pelvis showing a femoral head ligament extending from and attached to the acetabulum.

As shown in FIGS. 20 and 21, the patient's native anatomy includes an acetabulum 510 in the pelvis 512 that is adapted to receive femoral head 514 at the proximal end of the femur 516, so the femoral head is received within a cavity defined by the acetabulum to form a ball and socket joint. In a patient's native hip joint, the acetabulum 510 defines a cavity having a spherical center that is concentric with the spherical center of the femoral head 514. As the femoral head 514 pivots with respect to the acetabulum 510, this common spherical center orientation is maintained. But preexisting orthopedic hip joints do not maintain this common spherical center orientation between the cavity of the acetabulum and the femoral head.

An exemplary approach for determining and maintaining this common spherical center orientation uses human anatomical landmarks, such as the femoral head ligament 520. The femoral head ligament 520 is a major constraint that is currently removed without any attempt by the surgeon to utilize its location to define cup orientation. In contrast, this exemplary technique includes retention of certain features of the acetabulum before an instrument may be used to define the location of the femoral head ligament.

Figure 22:
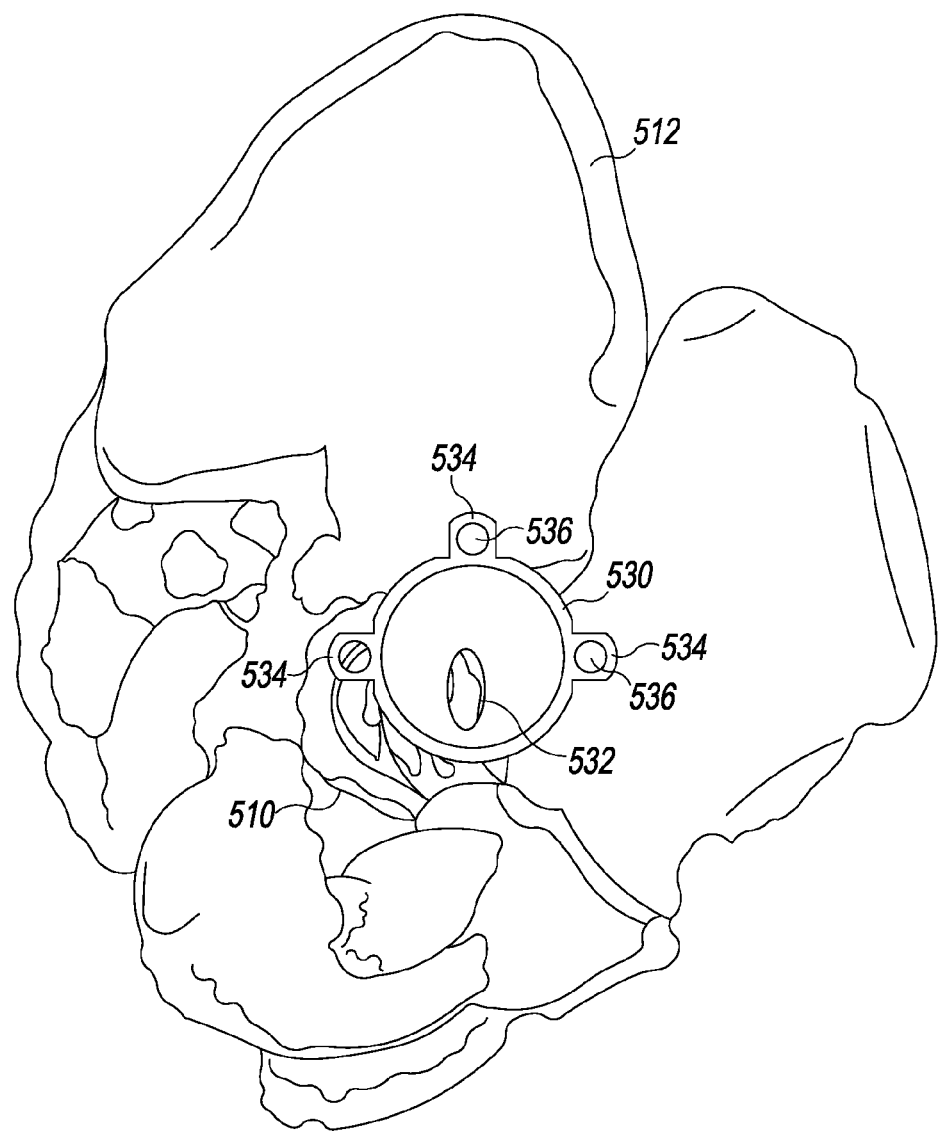
FIG. 22 is an overhead view of a landmark cup in accordance with the instant disclosure shown prior to insertion into the acetabulum.

Referring to FIG. 22, a landmark cup or jig 530 includes an orifice 532 sized accommodate a portion of the femoral head ligament 520 that remains attached to the acetabulum 510. In this exemplary embodiment, the landmark cup 530 is bowl-shaped and includes a plurality of tabs 534. Each tab 534 includes a through hole 536 that corresponds to the location of a fastener used to secure an acetabular cup to the pelvis 512.

Figure 23:
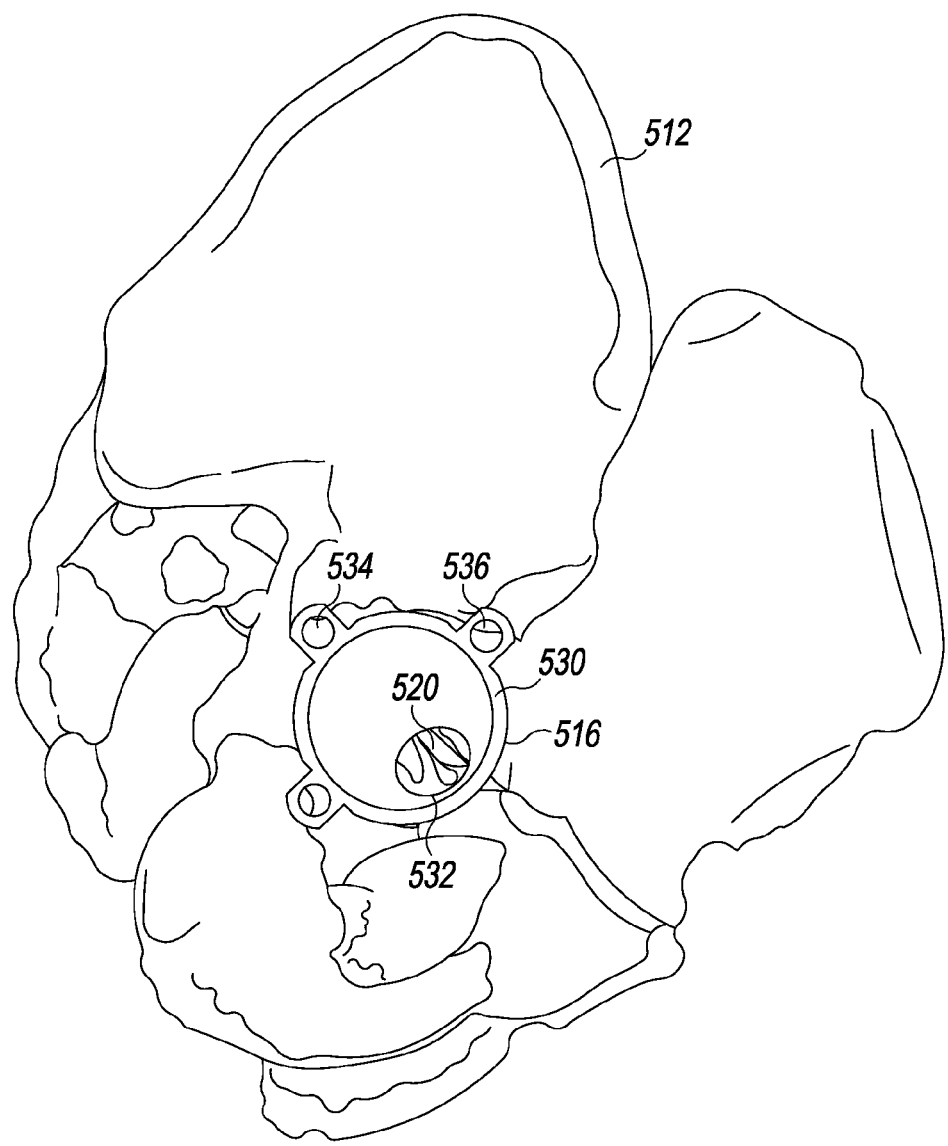
FIG. 23 is an overhead view of the landmark cup of FIG. 22, shown subsequent to insertion into the acetabulum.

Referencing FIG. 23, the landmark cup 530 is positioned over the acetabulum 510 so that the orifice 532 overlies the location of the femoral head ligament 520. The orifice 532 may take on various sizes and various positions within the cup 530 to mark the location of the femoral head ligament and may be used on multiple patients having variable femoral head ligament locations in the acetabulum. More specifically, after the orifice 532 is positioned to overlie the femoral head ligament 520, the cup 530 is pushed against the acetabulum 510, with the femoral head ligament extending through the orifice. Thereafter, holes are drilled into the pelvis 512 using the tab holes 536 as guides.

It should be noted, however, that while the landmark cup 530 is generally in the shape of an acetabular cup, this shape is not critical. The cup 530 may be any shape, such as circular, elliptical, square, rectangular, etc., and could be of any size. What is critical is retention of at least one of the anatomical reference points associated with the acetabulum 510 so that mounting locations and/or acetabular cup orientation can be established prior to reaming of the acetabulum.

Figure 24:
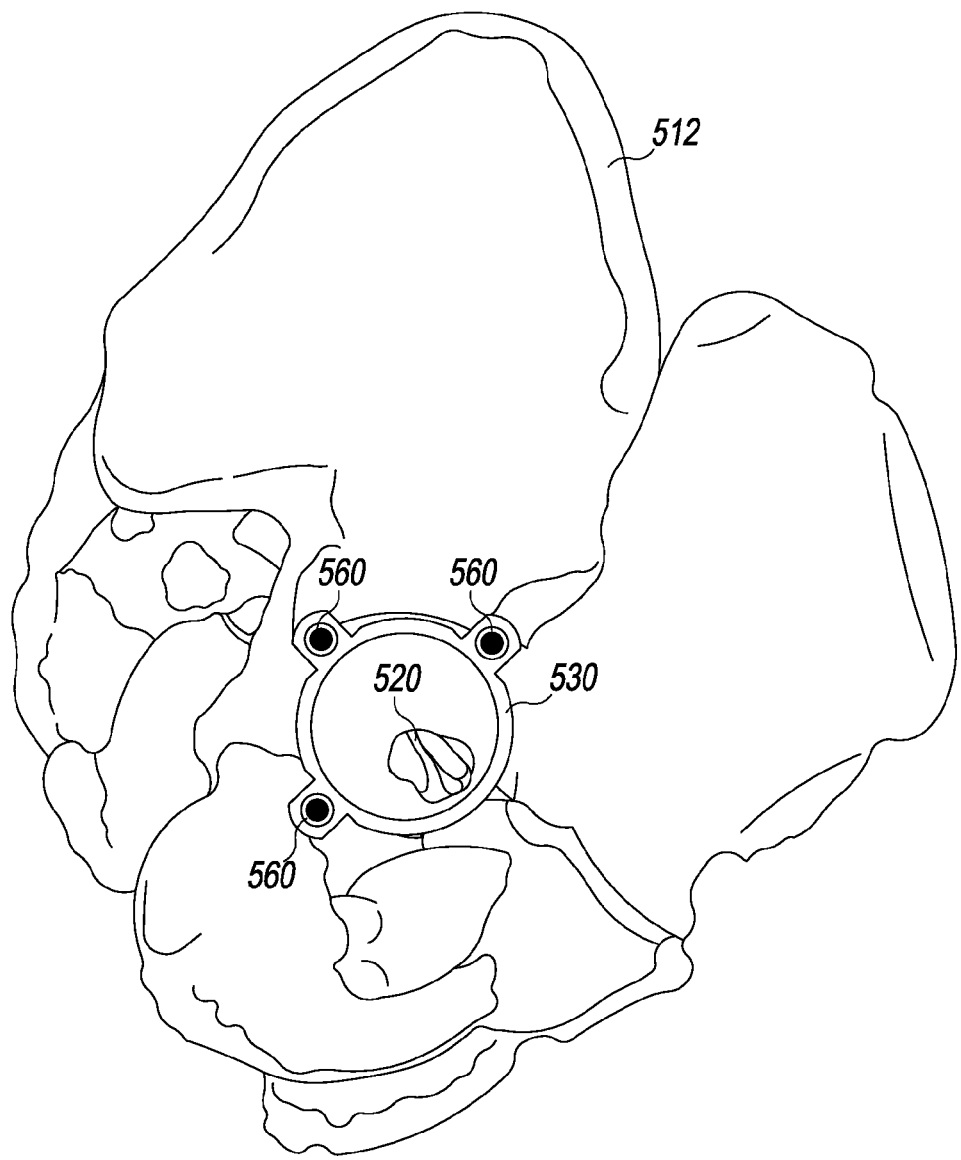
FIG. 24 is an overhead view of the landmark cup of FIG. 22, shown subsequent to insertion into the acetabulum and with the pins inserted.

Referring to FIG. 24, after the holes in the pelvis 512 are drilled, pins 560 are inserted into the holes. The landmark cup 530 is also removed, which allows for this same orientation to be utilized later in the surgery for reaming and permanent acetabular cup 570 positioning (see FIG. 29).

Figure 25:
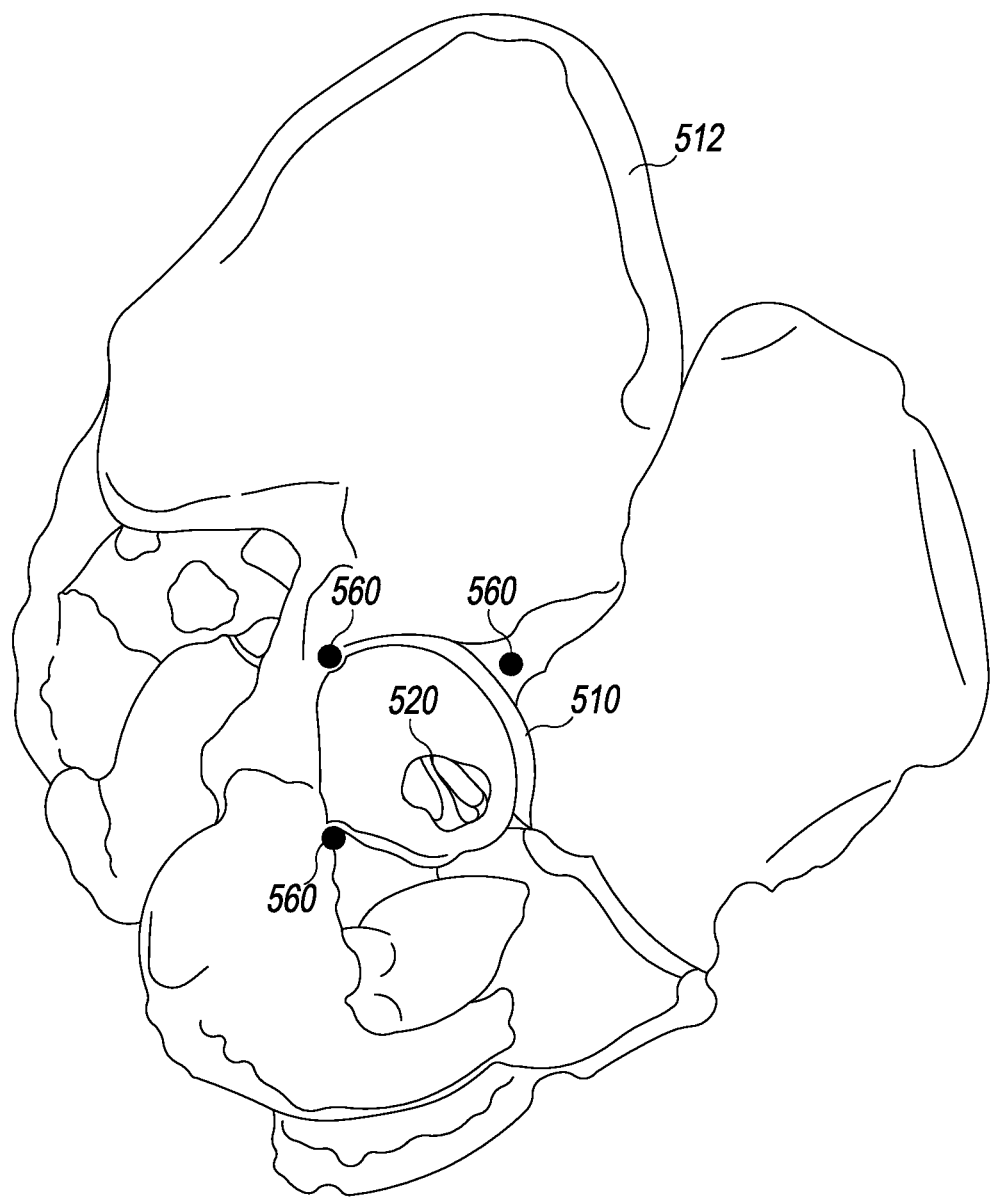
FIG. 25 is a profile view of the acetabulum after the landmark cup has been removed.

Referencing FIG. 25, the pins 560 remain in the pelvis 512 after the landmark 530 is removed. Thereafter, as shown in FIG. 26, the acetabulum 510 is prepared to receive the permanent acetabular cup 570 (see FIG. 29).

Figure 26:
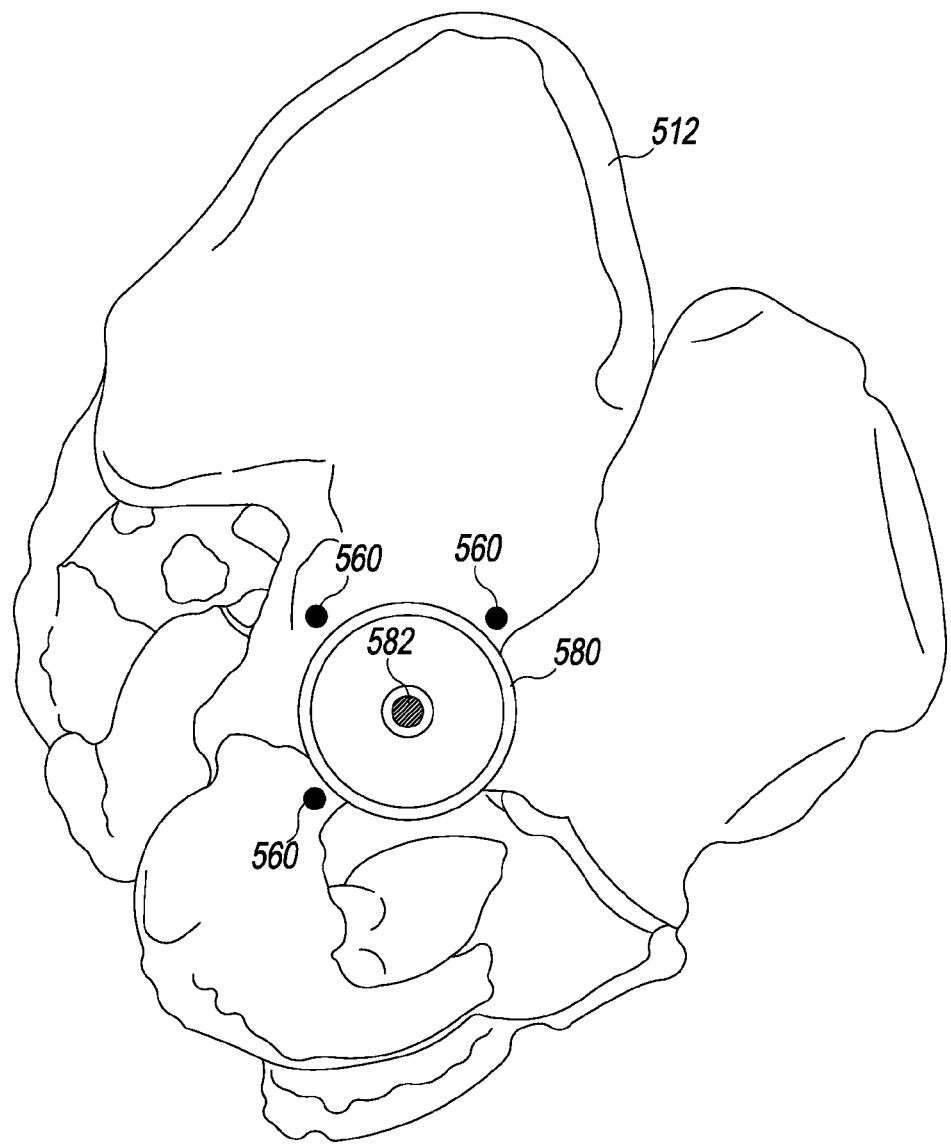
FIG. 26 is an overhead view of an exemplary guide pin cup and guide pin used to orient a reamer reaming the acetabulum.
Figure 27:
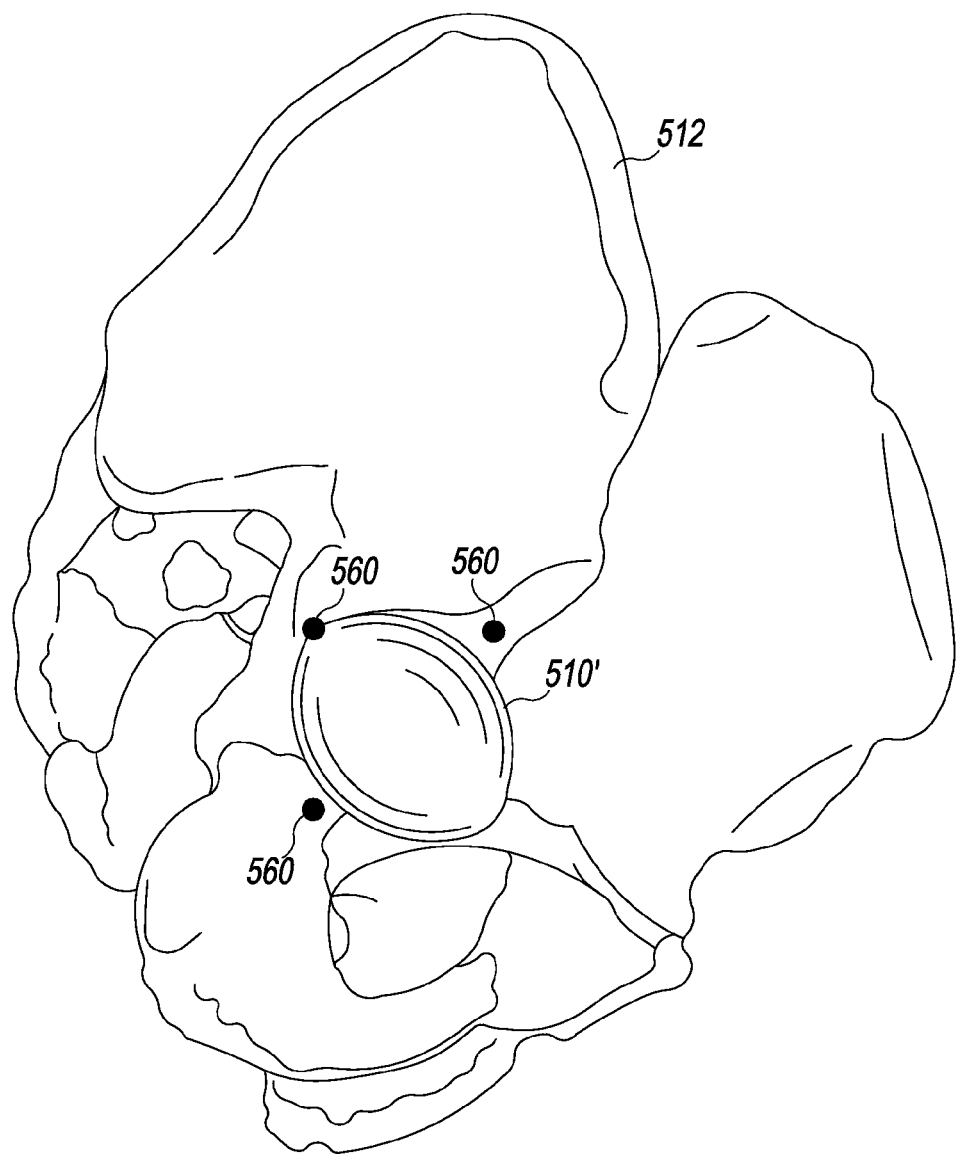
FIG. 27 is a profile view of a reamed acetabulum.

Referring to FIGS. 26 and 27, it is currently difficult for the surgeon to properly ream out the acetabulum so the acetabular cup and cup insert are positioned correctly. To help the surgeon properly ream out the acetabulum, after the landmark cup 530 has been removed, a guide pin cup 580 is secured to the acetabulum using the pins 560 that extend through corresponding openings in the guide pin cup. The guide pin cup 580 includes an opening exposing a portion of the acetabulum where the femoral head ligament is located. After the guide pin cup 580 is in position, a guide pin 582 is secured to the acetabulum at the center of the socket, referenced with respect to the femoral head ligament, and/or other bone or soft-tissue landmarks. This guide pin 582 may be 1.0 cm to 20 cm in length and have diameter from 0.1 cm to 3.0 cm, for example. The guide pin 582 may be fabricated from numerous materials such as, without limitation, cobalt chrome, steel, titanium, tantalum, and ceramics. Thereafter, the guide pin cup 580 is removed from over top of the guide pin 582 and the ancillary pins 560, which leaves the guide pin 582 mounted to the acetabulum. Using the guide pin 582 and the ancillary pins 560 on the pelvic bone, a reamer (not shown) is inserted in the socket and the acetabulum is reamed uniformly and in the correct direction to create a revised acetabulum 510 (see FIG. 27). After reaming, the reamer and guide pin 560 are both removed, while the ancillary pins 560 are retained to guide the implanted cup into the socket.

Figure 28:
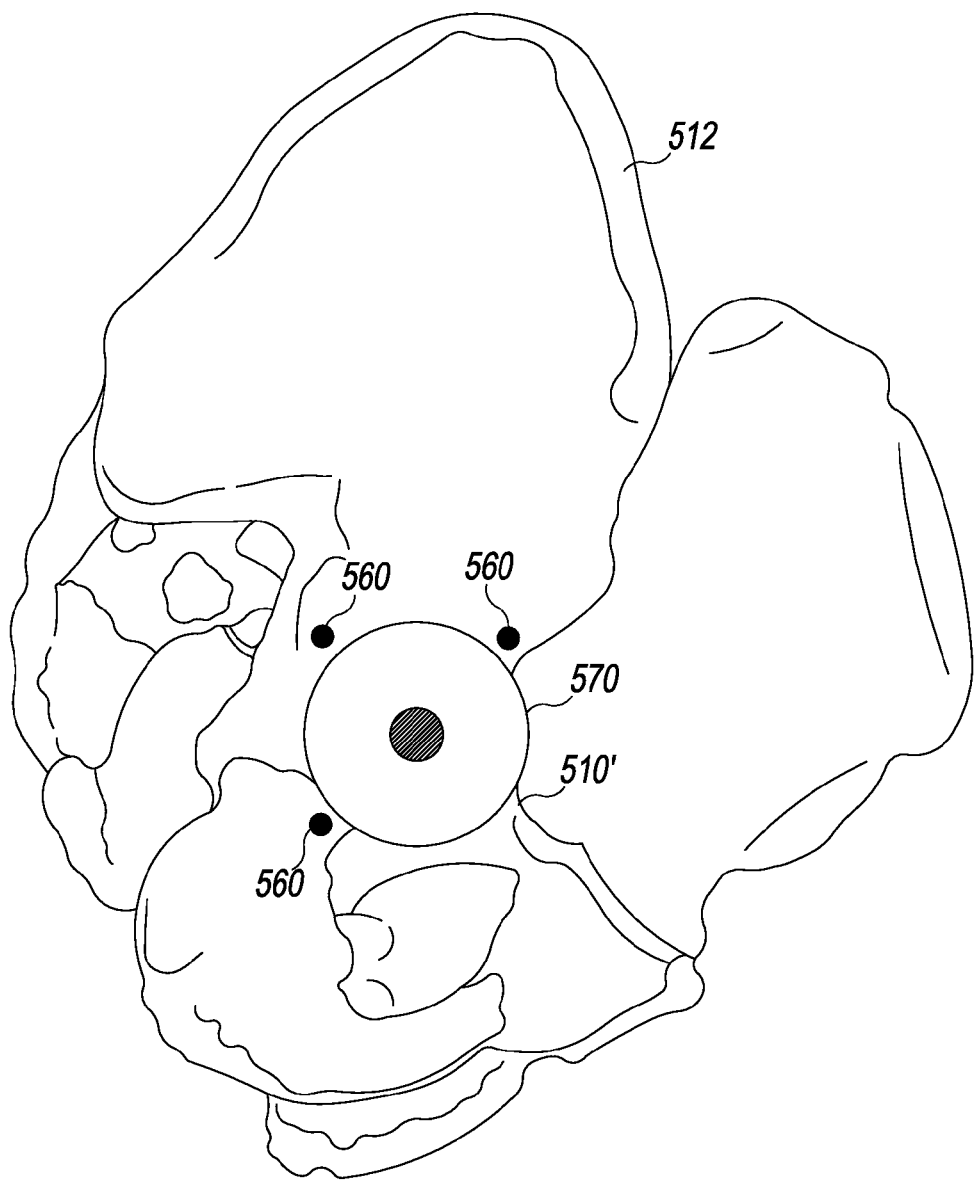
FIG. 28 is an overhead view of a permanent acetabular cup mounted to the pelvis.

Referring to FIG. 28, the permanent acetabular cup 570 is inserted into the revised acetabulum 510' using the guide pins 560 so as to maintain the proper orientation necessary to produce concentricity with the femoral head.

Figure 29:
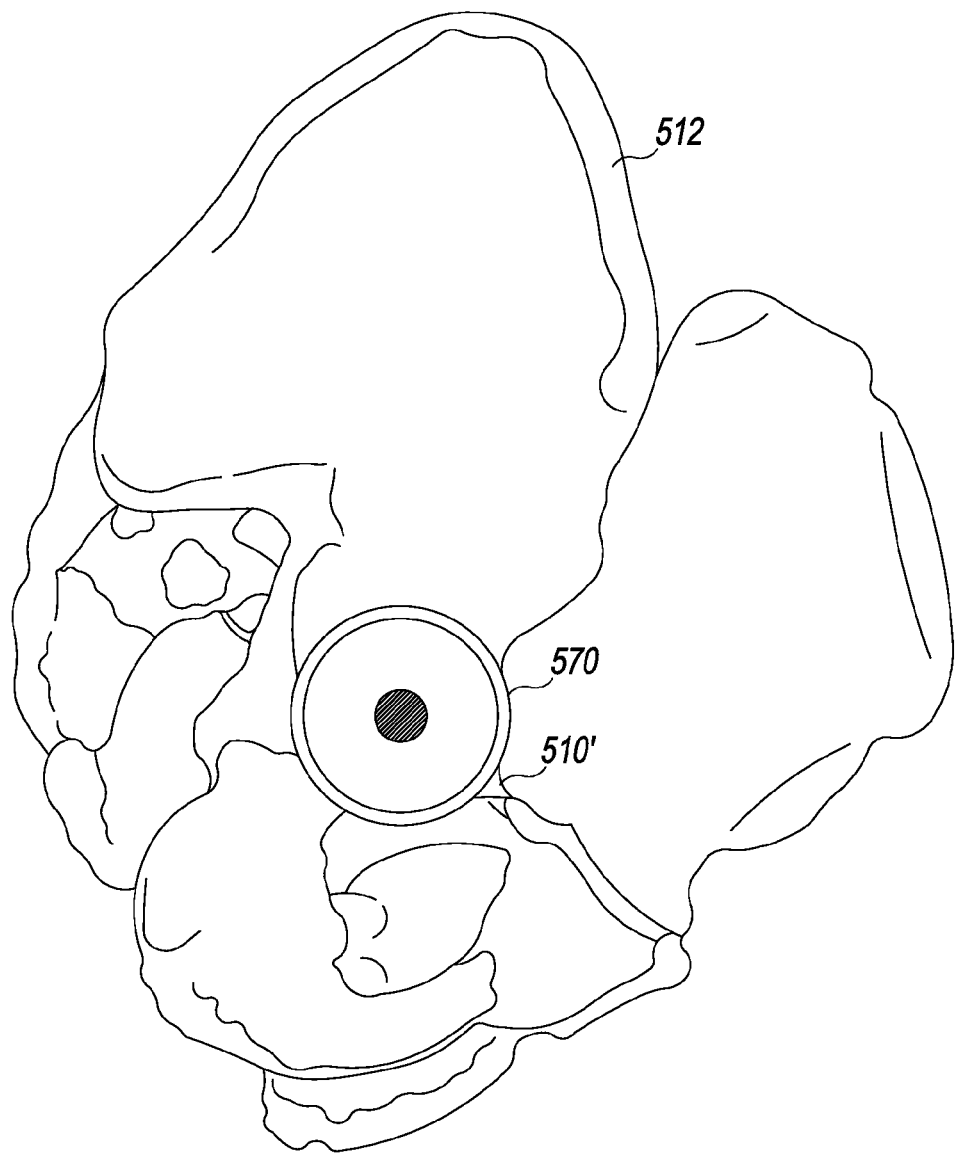
FIG. 29 is an overhead view of the permanent acetabular cup of FIG. 28, with the guide pins removed.

Referring to FIG. 29, after the acetabular cup 570 is securely in place within the revised acetabulum 510, the guide pins 560 are removed and the corresponding holes filled.

Referring back to FIG. 20, during weight-bearing gait, the femoral head ligament 520 remains taught so that the ligament distance throughout the weight-bearing portion of the gait cycle remains constant. The location of the femoral head ligament 520 attachment site in the acetabulum 510 is identified as point A. The location of the femoral head ligament attachment 520 site on the femoral head 514 is identified as point B, Therefore, if the line constructed from point A to point B is constant throughout the weight-bearing portion of the gait cycle, then one may use this line to define the location of the proper acetabulum sphere. Since points B and C are on the same bone, a fixed body, then the distance from points B to C is always constant. Therefore, by knowing the distances from points A to B and B to C, one may construct a line from point A to point C, which is also a constant. Although this analysis is planar in nature, a fourth out-of-plane point may be used to align the longitudinal direction of the cup. By identifying the location of the femoral head ligament 520 in the acetabulum 510, prior to the acetabulum being prepared during surgery, the distance from the femoral head ligament 520 to the spherical center of the acetabular cup 570 (see FIG. 29) and the femoral head 514 is measured to ensure that the proper spherical center has been maintained. The femoral head ligament 520 is the only landmark within the acetabulum 510 that can be used to define the location of the proper spherical center. Knowing the distance from the femoral head ligament 520 attachment site, within the acetabulum 510 to the proper spherical center is crucial to the surgical alignment and implantation of the acetabular cup 570 and femoral head 514.

Although the example just described may be used to define concentric spheres during surgery, one could use a number of methodologies to located and/or maintain concentric spheres post THA. In an exemplary simplistic methodology, one could attempt to define and maintain concentricity using static x-rays, but this method would be in two-dimensions and may not properly define concentricity in three-dimensions. This method may only allow one to define similar circular centers. One could also use pre-operative planning and/or imaging, such as MRI, CT scans, ultrasound and/or any other imaging modality. Most of the imaging modalities that can presently be used are static and may subject the patient to radiation exposure. One could also use intra-operative surgical navigation and/or imaging modalities to locate and/or maintain concentric spheres. Most importantly, it is important to ensure that proper cup and femoral stem orientation is chosen to ensure concentric spheres post THA surgery.

Figure 30:
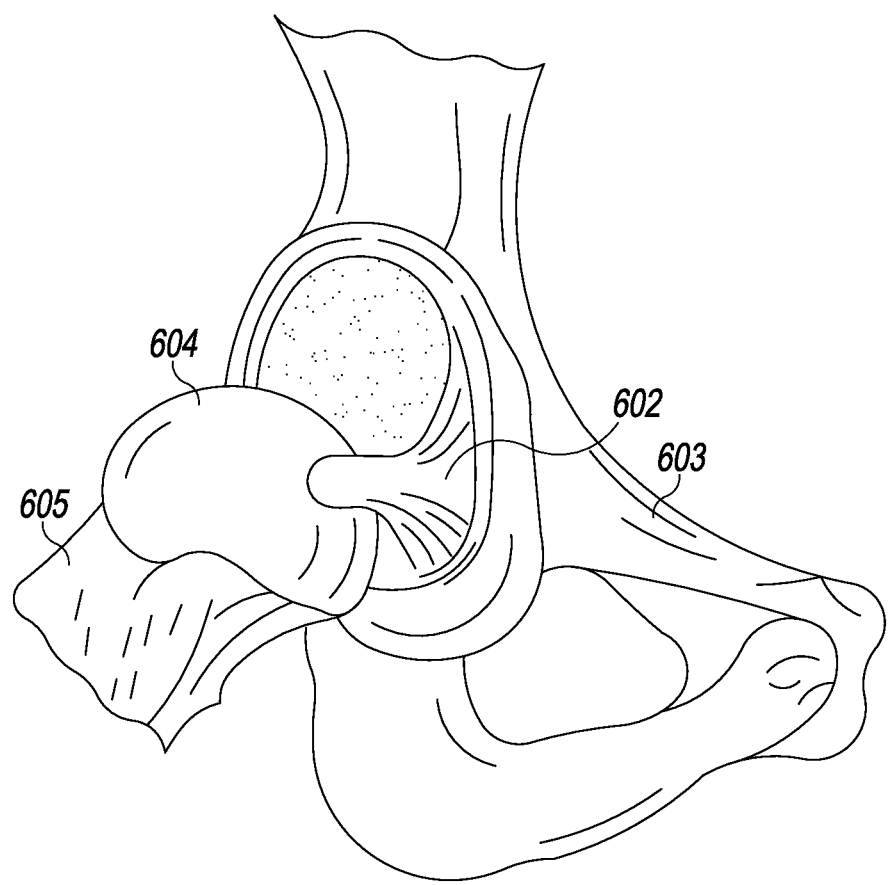
FIG. 30 is a profile view of a natural human hip joint.

Referring to FIG. 30, all present-day THA surgeries require removal of the femoral head ligament 602. But this exemplary embodiment of a prosthetic hip joint retains the femoral head ligament 602 if it is healthy. As stated previously, the femoral head ligament 602 is a stabilizing mechanism in the hip joint that couples the pelvis 603 to the femur 605.

If the femoral head ligament 602 is not healthy, an artificial structure may be used to reinforce the femoral head ligament. This artificial structure may be comprised of any number of materials such as, without limitation, twine, silicone rubber, elastic silicone rubber, gutta percha, saline rubber, gore-tex, polystyrene, polytetrafluoroethylene, nylon, polyethylene, polyester, silk, polyethylene teraphthalate, and polyvinyl alcohol-hydrogel. This material may be wrapped around the femoral head ligament 602, attached to the base of the femoral head ligament attachment site in the acetabulum, inter twined within the femoral head ligament, or used in another manner to reinforce the strength of the femoral head ligament.

Figure 31:
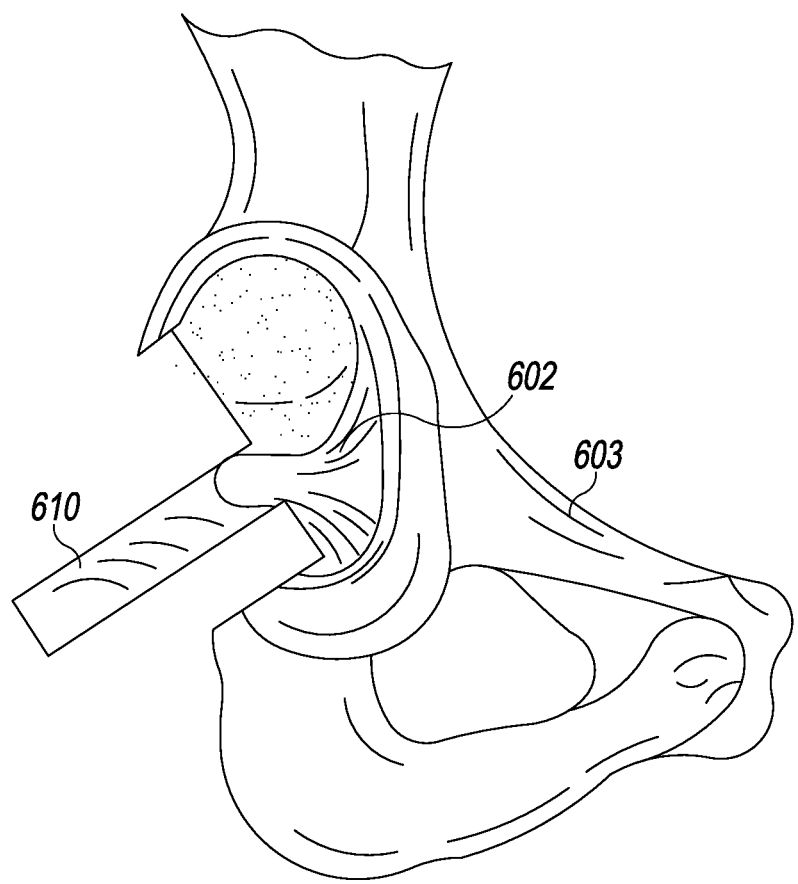
FIG. 31 is a profile view showing a femoral aspect of a further exemplary hip joint in accordance with the instant disclosure, while attached to the native pelvis.

Referencing FIGS. 30 and 31, initially, the femoral head 604 is severed from the remainder of the femur 605. A cutting instrument (not shown) is then used to shape a bone segment 610 from the femoral head 604, where the bone segment remains attached to the femoral head ligament 602. In exemplary form, the bone segment 610 is cut into a cylindrical shape having the same length as the native femoral head 604, with one end of the cylinder being mounted to the femoral head ligament 602. It should be noted that the cylindrical shape is not critical and other shapes and sizes such as, without limitation, rectangular, triangular, and rounded may be utilized as part retaining the bone segment.

Figure 32:
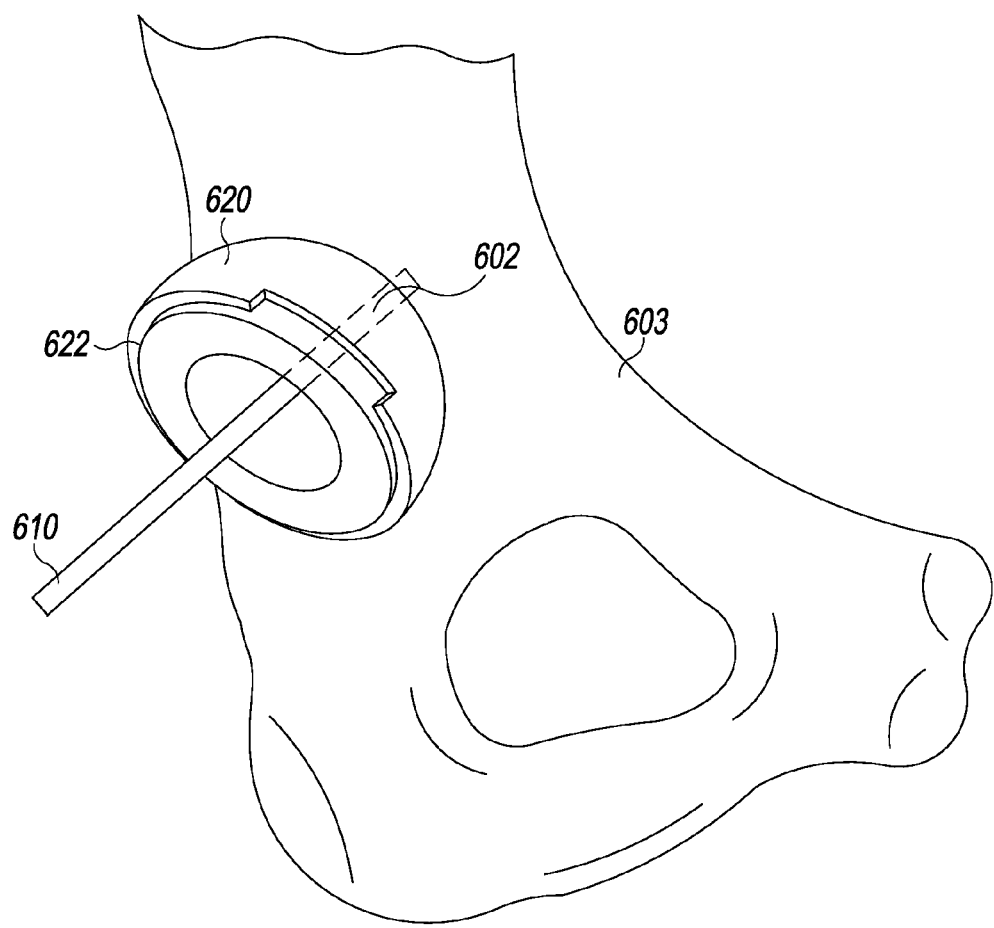
FIG. 32 is a profile view showing the femoral aspect and an acetabular component of the further exemplary hip joint in accordance with the instant disclosure, while attached to the native pelvis.
Figure 33:
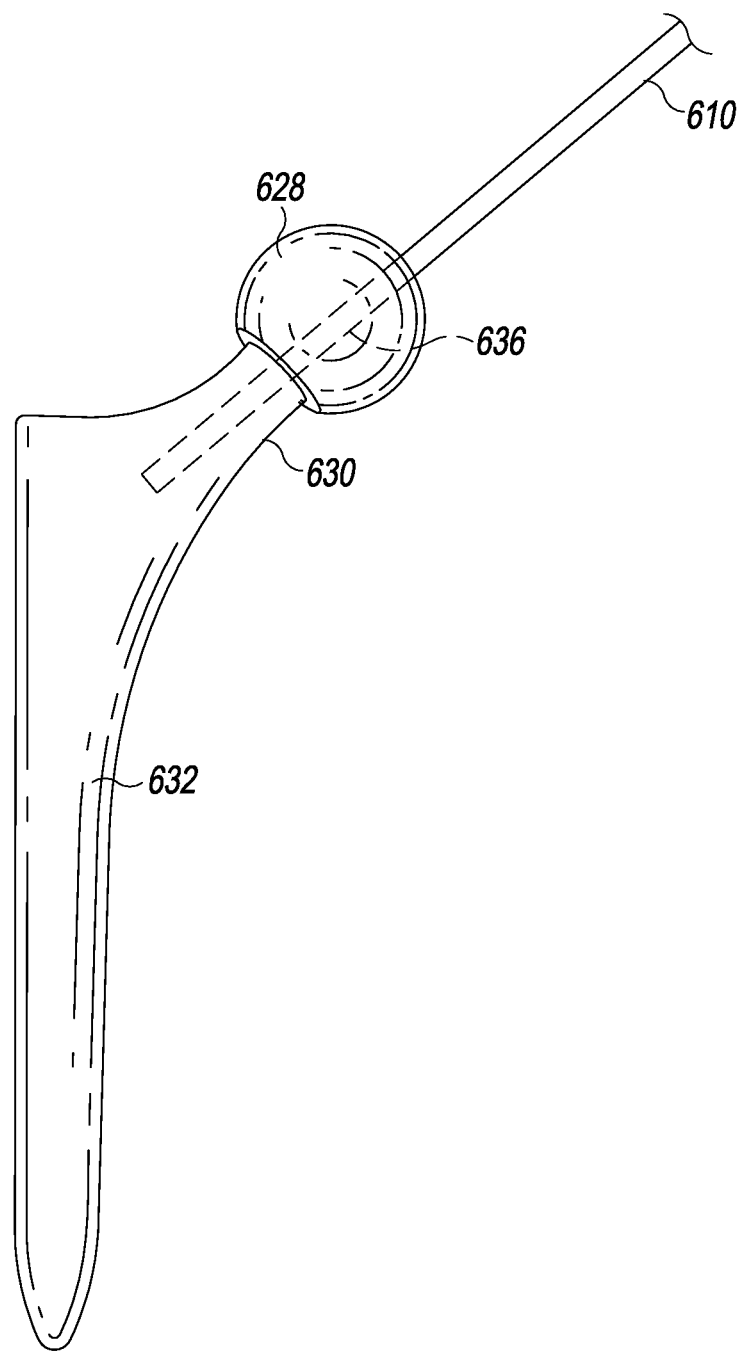
FIG. 33 is a profile view showing the femoral aspect of the further exemplary hip joint, prior to insertion into a femoral component.
Figure 34:
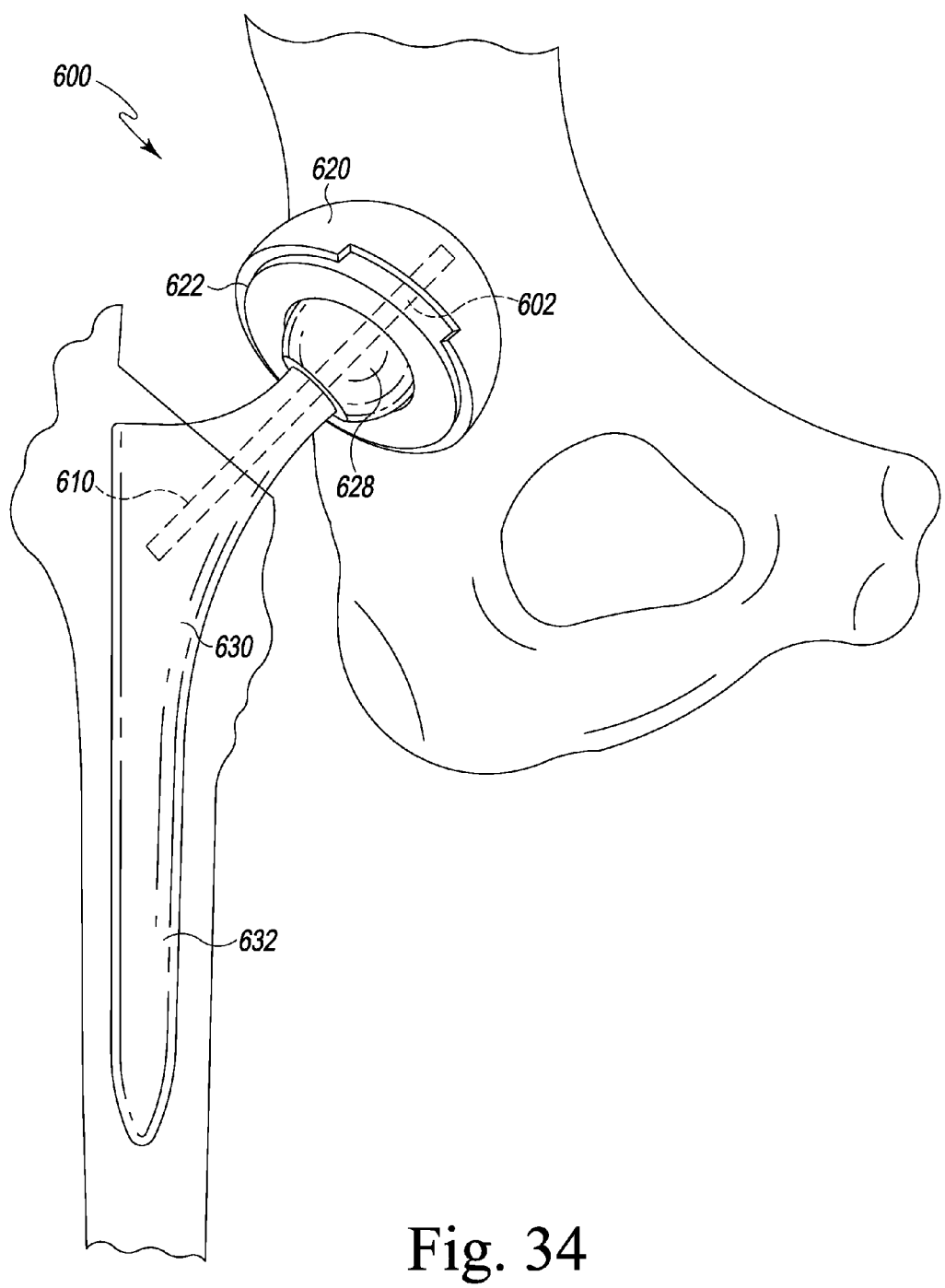
FIG. 34 is a profile view showing the femoral component, femoral aspect, and an acetabular component of the further exemplary hip joint, while attached to the native pelvis and femur.

Referring to FIGS. 32-34, the exemplary prosthetic hip joint 600 comprises an acetabular cup 620 and an acetabular cup liner 622 each having a through orifice (not shown) that is sized to allow throughput of the femoral head ligament 602 and the bone segment 610. The exemplary prosthetic hip joint 600 also comprises a femoral ball 628, a femoral neck 630, and a femoral stem 632, where the femoral neck is integrally formed with the femoral stem. The femoral ball 628 includes a through hole (not shown) that is sized to allow insertion of the bone segment 610 so the portion of the bone segment to which the femoral head ligament is mounted is substantially flush with the exterior arcuate surface of the ball. The neck 630 includes a cavity 636 axially aligned with the through hole in order to receive a portion of the bone segment 610. In this exemplary embodiment, the cavity 636 is cylindrical.

Referring to FIGS. 32-34, implantation of the exemplary prosthetic hip joint 600 includes utilizing a cutting instrument to create a bone segment 610 that is mounted at one end to the femoral head ligament 602 and free at an opposing end. The femoral head ligament 602 during this process remains attached to the pelvis 603. After the bone segment 610 is cut, the bone segment and a portion of the femoral head ligament 602 are thread through the through orifice of the acetabular cup 620. The acetabular cup 620 is then mounted to the pelvis 603. The bone segment 610 and a portion of the femoral head ligament 602 are next thread through the through orifice of the acetabular cup liner 622. The acetabular cup liner 622 is then mounted to the acetabular cup 620. Then, the bone segment 610 is thread through the through hole of the femoral ball 628 so that the end of the bone segment mounted to the femoral head ligament 602 is substantially flush with the bearing surface of the femoral ball. And at least a portion of the remaining bone segment 610 not received within the femoral ball 628 is received within the femoral neck cavity 636.

The bone segment 610 may be attached to the femoral neck 630 using numerous methodologies and techniques. An exemplary method for use with the instant exemplary embodiment 600 includes applying bone cement in between the bone segment 610 and the wall(s) of the femoral neck 630 that delineate the cavity 636. Another exemplary method includes interposing bone ingrowth material between the bone segment 610 and the wall(s) of the femoral neck 630 that delineate the cavity 636.

The femoral ball 628 may alternatively be tapered to create a cap-like indentation at the site where femoral head bone is received. The location on the femoral ball 628, where the femoral head bone is received thus does not have to be tapered and does not have be a cylindrical hole. In other words, the cavity on the femoral ball 628 to receive the modified femoral head bone may be any of a number of shapes.

The amount of bone retained from the femoral head bone may be of any size and shape. The length of this retained femoral head bone may be long enough to be fixated within only the femoral ball 628, or it can be longer to insert through the femoral ball and into the femoral neck 630 of the femoral prosthesis. Alternatively, the retained femoral head bone may be long enough so that the distal end of the bone can pass through the femoral ball 628, through the femoral neck 630, through a portion of the femoral stem and into or through the femoral shaft 632. This technique may allow for blood supply to be maintained within the retained femoral head bone and the femoral head ligament, thus allowing the retained femoral head bone to grow into the femur.

Figure 35:
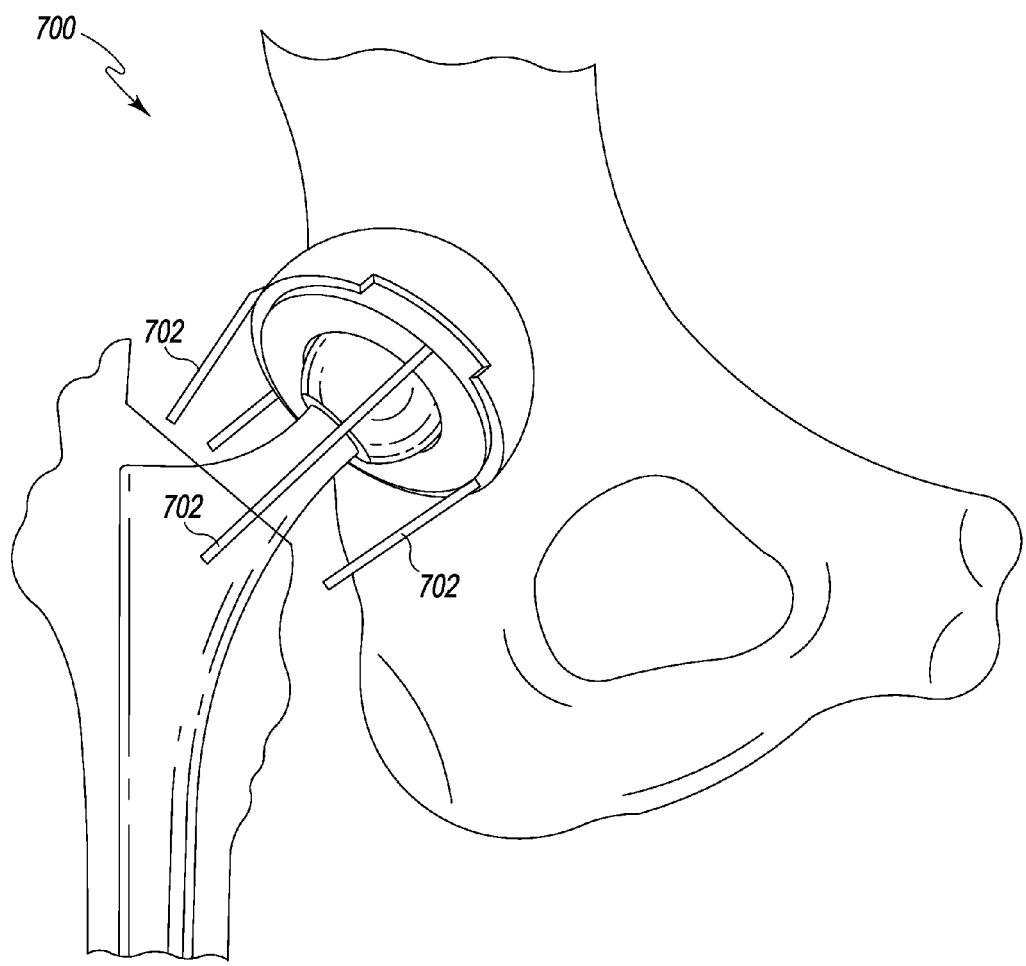
FIG. 35 is a profile view showing an even further exemplary hip joint, while attached to the native pelvis and femur.

Referring to FIG. 35, an alternate exemplary embodiment 700 is the same as the foregoing prosthetic hip joint 600, except for the addition of sutures or other retention lines 702 extending between at least two of the acetabular cup, acetabular cup liner, the femur, the femoral neck and the pelvis. These sutures or retention lines 702 may be utilized like suspenders, wrapping around the acetabular cup, between the cup and the bone and then either attaching to the femoral implant component or to the femoral bone. The acetabular cup may include grooves 704 to allow the sutures or other retention lines 702 to fit between the cup and the bone and then be securely cemented to the implant and the bone or allow for the bone to grow into the cup and/or the artificial structure.

Figure 36:
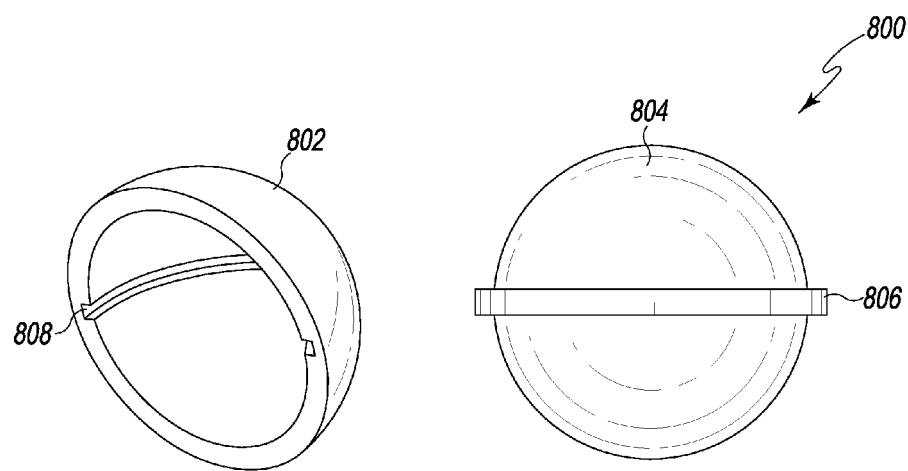
FIG. 36 includes an elevated perspective view of an exemplary acetabular cup and a bottom view of an exemplary acetabular cup insert.
Figure 37:
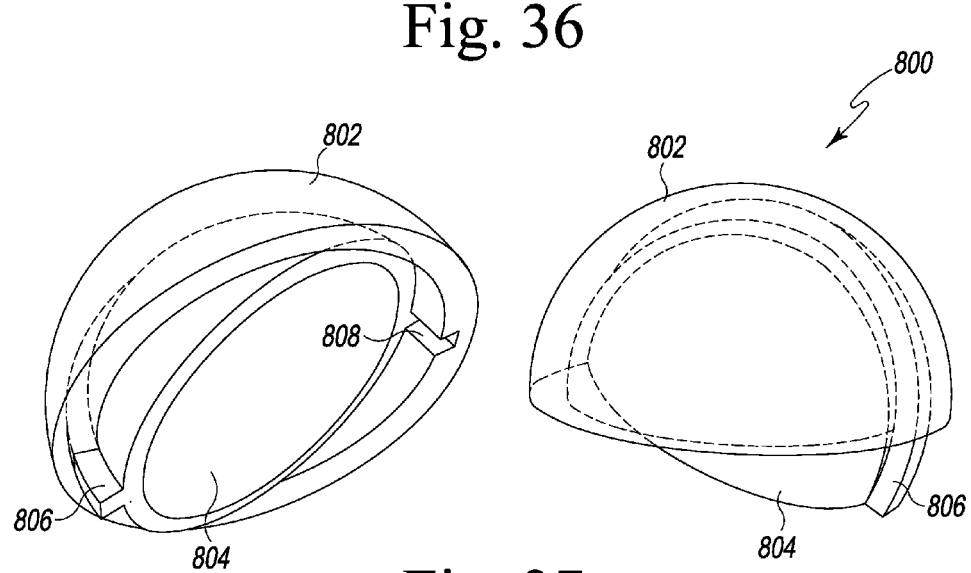
FIG. 37 comprises two perspective views showing some of the movement possible between the acetabular cup and acetabular cup insert of FIG. 36.
Figure 38:
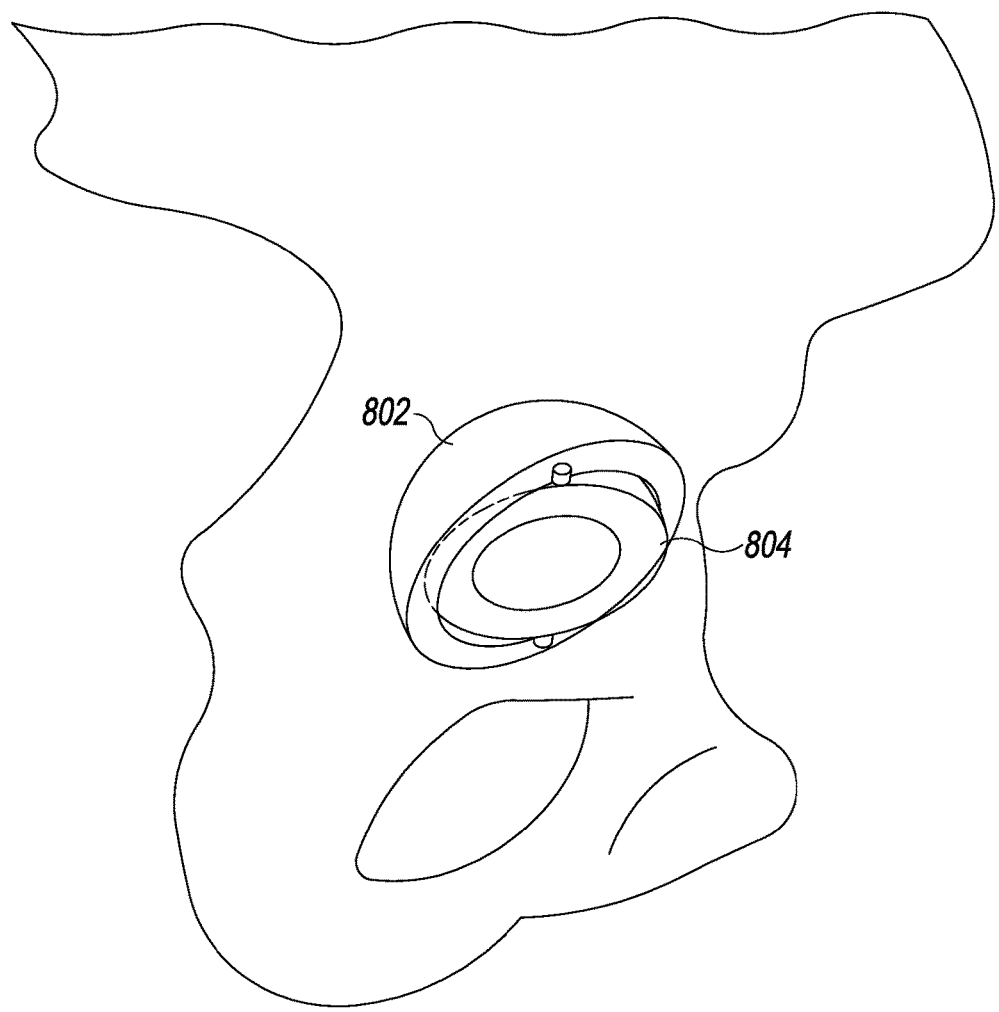
FIG. 38 is a perspective view of the acetabular cup and acetabular cup insert of FIG. 36, shown mounted to a pelvis.

Referencing FIGS. 36-38, an exemplary mobile bearing acetabular component 800 comprises an acetabular cup 802 and a repositionable cup insert 804. The repositionable cup insert 804 includes a semicircular rib 806 having a dove tail cross-section that extends circumferentially on the cup insert's exterior surface. This rib 806 is adapted to be at least partially received within a corresponding semicircular groove 808 formed on the interior of the cup 802. In this exemplary embodiment, the groove 808 takes on a dove tail shape. It should be noted, however, that other rib 806 and groove 808 shapes may be utilized such as, without limitation, the rib 806 having a T-shape and the groove 808 having a corresponding cavity to receive and retain the rib. Moreover, it is within the scope of the disclosure for the rib 806 to be located on the interior of the acetabular cup 802, while the groove 808 is located circumferentially on the cup insert 804.

In this exemplary embodiment, during weight-bearing activities, the cup insert 804 is locked and cannot slide and/or extend and remains in a fixed orientation with respect to the cup 802. During non weight-bearing activities, especially those that contribute to dislocation, the cup insert 804 is allowed to translate along one axis. Specifically, the rib 806 is repositionable within the groove 808, thereby allowing the cup insert 804 to translate along one axis with respect to the cup 802. Therefore, pre-operatively, if preferred, one may determine the correct cup 802 orientation so that the cup insert 804 will perfectly translate along an axis that the patient normally uses to perform the activities that cause femoral head dislocation. The cup insert 804 slides and/or extends in both directions along that chosen axis. Thus, when the patient performs non-weight bearing tasks, the cup insert 804 extends outside of the acetabular cup 802, ensuring that the femoral head does not dislocate. This cup insert 804 may have full freedom to translate and/or rotate along one axis within the cup 802 or the cup insert 804 may be constrained with some stopping and/or locking mechanism. This stopping and/or locking mechanism may constrain the translation in either direction and allow differing amounts of translation for each patient, depending on the amount of translation needed for each patient.

Figure 39:
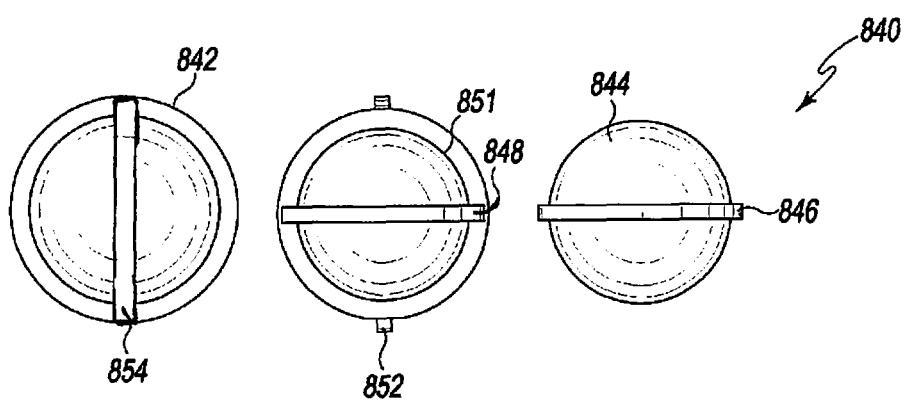
FIG. 39 includes a top view of an exemplary acetabular cup, a top view of an intermediate liner, and a bottom view of an exemplary acetabular cup insert.
Figure 40:
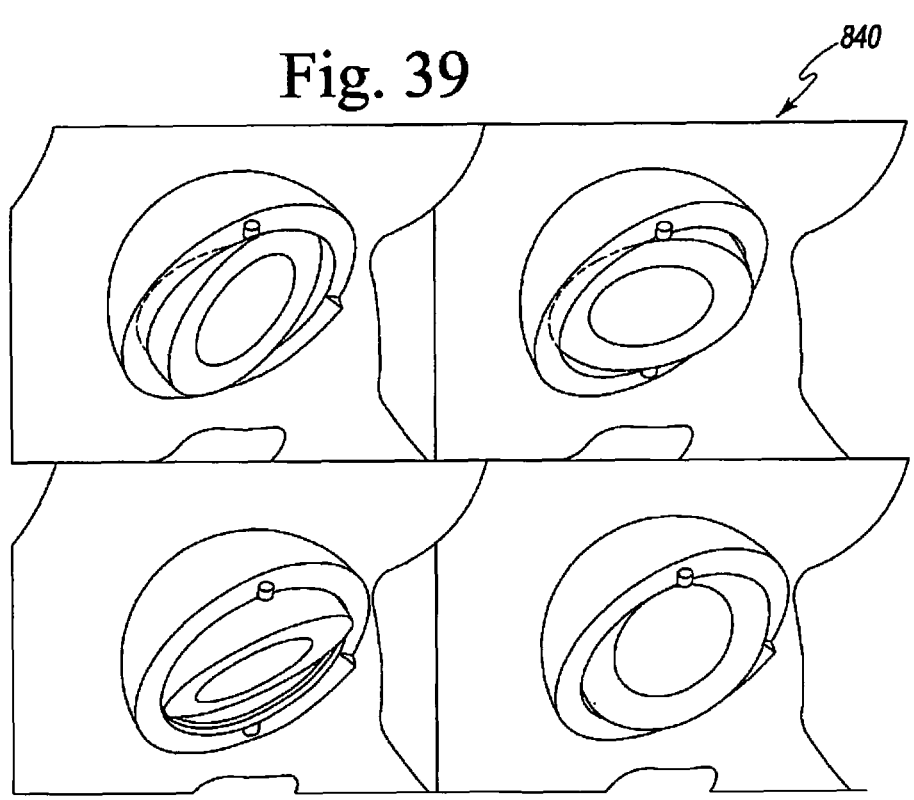
FIG. 40 are perspective views of the acetabular cup, acetabular liner, and acetabular cup insert of FIG. 39, shown mounted to a pelvis.

Referring to FIGS. 39 and 40, a second exemplary mobile bearing acetabular component 840 comprises an acetabular cup 842 and a repositionable cup insert 844. The repositionable cup insert 844 includes a semicircular rib 846 having a dove tail cross-section that extends circumferentially on the cup insert's exterior surface. This rib 846 is adapted to be at least partially received within a corresponding semicircular groove 848 formed on the interior of a semicircular track (not shown). In this exemplary embodiment, the groove 848 takes on a dove tail shape. It should be noted, however, that other rib 846 and groove 848 shapes may be utilized such as, without limitation, the rib 846 having a T-shape and the groove 848 having a corresponding cavity to receive and retain the rib. Moreover, it is within the scope of the disclosure for the rib 846 to be part of the track, while the groove 848 is located circumferentially on the cup insert 844.

Another way for this implant to achieve translation in two directions is to include an intermediate liner 851 (see FIG. 39) that fits between the acetabular cup 842 and the insert liner 844. This intermediate liner 851 can be polyethylene, metal, ceramic or any other bearing surface material. The intermediate liner 851 allows for the insert liner 844 to translate along one direction with respect to the intermediate liner, while the intermediate liner 844 translates along a second direction (e.g. perpendicular to the first direction) within the acetabular cup 842.

In this exemplary embodiment, the liner 851 includes a projection 852 formed on its circumferential exterior that is received within a corresponding semicircular groove 854 formed on the interior of the cup 842. In this exemplary embodiment, the groove 854 takes on a dove tail shape. It should be noted, however, that other projection 852 and groove 854 shapes may be utilized such as, without limitation, the projection 852 having a T-shape and the groove 854 having a corresponding cavity to receive and retain the projection. Moreover, it is within the scope of the disclosure for the projection 852 to be located on the interior of the acetabular cup 842, while the groove 854 is located on the circumferential exterior of the track 850.

The semicircular track 850 in FIG. 39 is rotationally offset ninety degrees from the groove 854 on the interior of the circumferential cup 842. It should be noted, however, that the track 850 need not be offset to precisely ninety degrees and may be offset at a variety of angles. In the manner shown in FIG. 39, the cup insert 844 may slide toward an east or west direction with respect to the semicircular track 850 and with respect to the acetabular cup 842, thereby sliding the cup insert in an east or west arcuate direction. At the same time, the track 850 may slide toward a north or south direction with respect to the acetabular cup 842, thereby sliding the cup insert 844 in a north or south arcuate direction. In other words, the net result is that there are two degrees of freedom for net movement of the cup insert 844 with respect to the cup 842. A first degree of freedom is an arcuate motion in a north or south direction, and the second degree of freedom is an arcuate motion in an east or west direction, where the degrees of freedom are independent of one another any may be exercised individually or in tandem.

Figure 41:
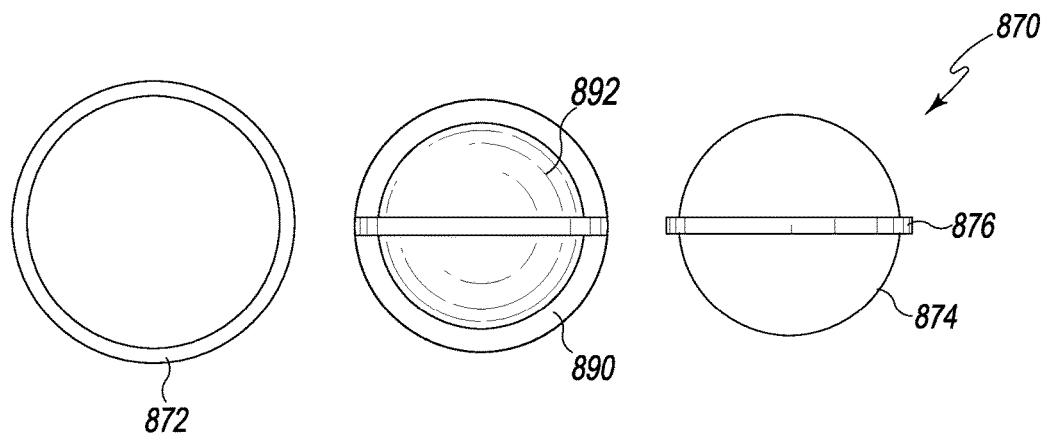
FIG. 41 includes a top view of an exemplary acetabular cup, a top view of an intermediate liner, and a bottom view of an exemplary acetabular cup insert.

Referring to FIG. 41, a third exemplary mobile bearing acetabular component 870 comprises an acetabular cup 872 and a repositionable cup insert 874. The repositionable cup insert 874 includes a semicircular rib 876 having a dove tail cross-section that extends circumferentially on the cup insert's exterior surface. This rib 876 is adapted to be at least partially received within a corresponding semicircular groove 878 formed on the interior of a semicircular track 880. In this exemplary embodiment, the groove 878 takes on a dove tail shape. It should be noted, however, that other rib 876 and groove 878 shapes may be utilized such as, without limitation, the rib 876 having a T-shape and the groove 878 having a corresponding cavity to receive and retain the rib. Moreover, it is within the scope of the disclosure for the rib 876 to be part of the track 880, while the groove 878 is located circumferentially on the cup insert 874.

In this exemplary embodiment, the semicircular track 880 includes a projection 882 formed on its circumferential exterior that is received within a corresponding semicircular groove 884 formed on the interior of the cup 872. In this exemplary embodiment, the groove 884 takes on a dove tail shape. It should be noted, however, that other projection 882 and groove 884 shapes may be utilized such as, without limitation, the projection 882 having a T-shape and the groove 884 having a corresponding cavity to receive and retain the projection. Moreover, it is within the scope of the disclosure for the projection 882 to be located on the interior of the acetabular cup 872, while the groove 854 is located on the circumferential exterior of the track 850.

The semicircular track 880 is rotationally repositionable with respect to the groove 884 on the interior of the circumferential cup 872. In this manner, the cup insert 874 may slide toward an east or west direction with respect to the semicircular track 880 and with respect to the acetabular cup 872, thereby sliding the cup insert in an east or west arcuate direction. In addition, the cup insert 874 is rotatable with respect to the acetabular cup 872 in 360 degrees. At the same time, the track 880 may slide toward a north or south direction with respect to the acetabular cup 872, thereby sliding the cup insert 874 in a north or south arcuate direction. In other words, the net result is that there are three degrees of freedom for net movement of the cup insert 874 with respect to the cup 872. A first degree of freedom is an arcuate motion in a north or south direction, a second degree of freedom is an arcuate motion in an east or west direction, and a third degree of freedom is axial rotation, where the degrees of freedom are independent of one another any may be exercised individually, at once, or in tandem.

Another manner for this implant 870 to achieve translation and rotation could be through the use of an intermediate liner 890 that rotates freely with respect to the acetabular cup 872, but includes a groove 892 that allows the cup insert 874 to freely translate along one direction. Since the intermediate liner 890 can freely rotate, the direction of the insert liner translation may be in any direction with respect to the acetabular cup 872 and/or the patient's natural anatomy.

Although most THA acetabular cups are designed to be a sphere, the cup may alternatively be elliptical allowing for the insert to translate and/or rotate to a greater amount, if deemed necessary.

Figure 42:
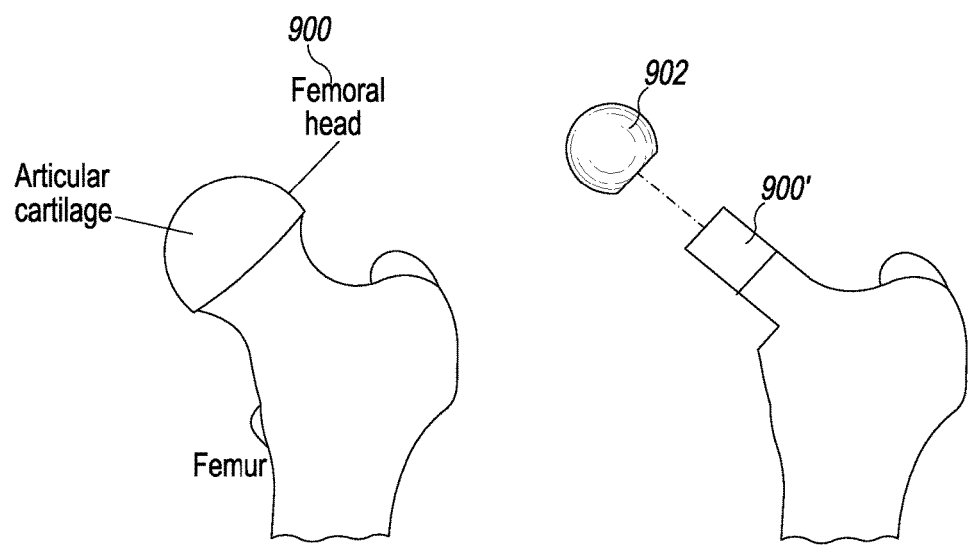
FIG. 42 includes comparison views of a femoral head prior to reshaping of the femoral neck.

Referring to FIG. 42, an exemplary process for use with hip joint surgery includes removing the native femoral head 900 of a patient to reshape the neck of the femoral neck bone. After the femoral head is removed, an implanted femoral head is inserted into and/or around the reshaped femoral neck bone, resembling an implanted hip stem and femoral head. While the shaped femoral head 900 is shown as having a cylindrical shape, it should be understood that the femoral head may be shaped in a rectangular, spherical, cylindrical, trapezoidal, or another other shape that could be beneficial for attaching a femoral ball 902 to the native bone. Although not shown in this figure, the femoral head may have a stem that inserts into the femoral neck bone. Also, the full femoral head bone anatomy does not have to be removed and the implanted femoral head may be attached onto the femoral head bone.

Figure 43:
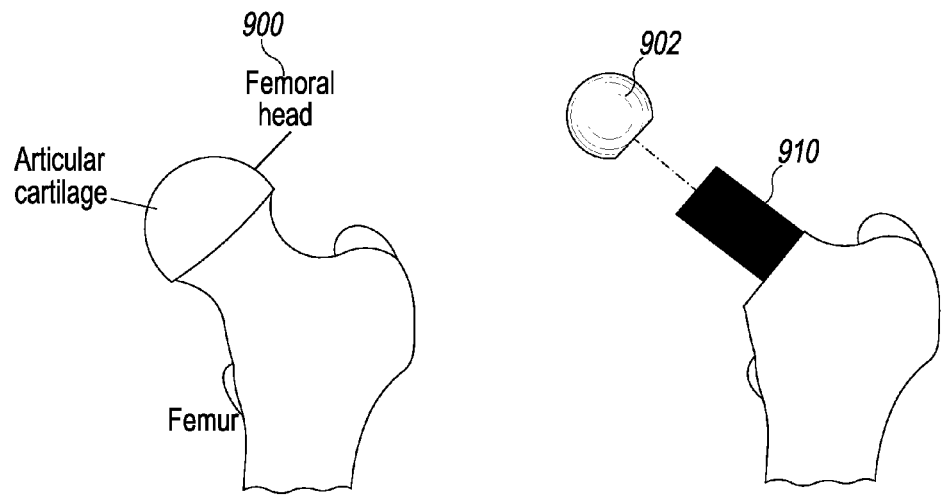
FIG. 43 includes comparison views of a femoral head prior to reshaping of the femoral neck in mounting thereto a cylindrical sleeve.

Referencing FIG. 43, another exemplary process for use with hip joint surgery includes removing or reshaping the native femoral head 900 of a patient to resemble the neck of a prosthetic femoral component. Thereafter, a metal, ceramic or any other implantable material cylindrical sleeve 910 is positioned to circumscribe the reshaped bone 900' (see FIG. 42) for stabilization. After the sleeve 910 is mounted to the reshaped femoral head 900, a prosthetic femoral ball 902 is mounted to the reshaped femoral head and/or femoral neck.

Figure 44:
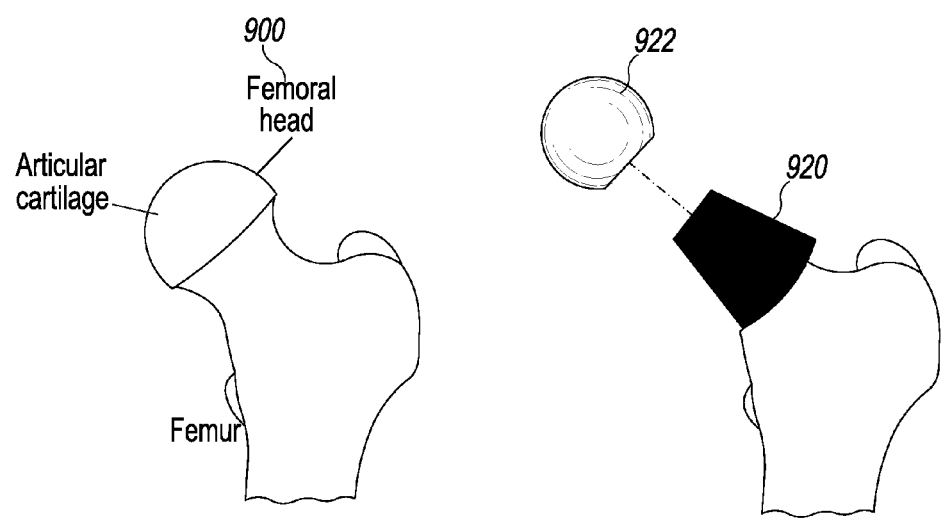
FIG. 44 includes comparison views of a femoral head prior to reshaping of the femoral neck in mounting thereto a conical sleeve.

Referring to FIG. 44, a further exemplary process for use with hip joint surgery includes removing and/or reshaping the native femoral head and/or neck 900 of a patient to resemble the neck of a prosthetic femoral component. In this exemplary process, the femoral head 900 is reshaped and a trapezoidal sleeve 920 is positioned to circumscribe the reshaped bone for stabilization. After the sleeve 920 is mounted to the reshaped femoral head, a prosthetic femoral ball 922 is mounted to the reshaped femoral head.

In the foregoing exemplary processes of FIGS. 42 and 43, it is also within the scope of the disclosure that the sleeve 910, 920 and the femoral ball 902, 922 comprise a single, integral component. Likewise, the femoral head can slide over the bone and/or the femoral sleeve, or it can also have an internal like stem that could go into the bone of the femur. It should also be noted that while the femoral head and femoral sleeve are shown as two separate pieces, the femoral head and femoral sleeve may also be one piece and/or modular to allow for these aspects to be attached creating one secure piece.

Referring to FIGS. 45-49, a surgeon improperly reaming out the acetabulum may lead to the placement of the acetabular cup at a location not allowing for concentricity with the femoral head of the femoral implant. Since concentricity of these components is essential to minimize or eliminate both hip dislocation and/or femoral head separation, an irregular acetabular cup or cup insert may be required to accommodate for the improper reaming. Specifically, the exemplary irregular acetabular cup or cup insert 1000 does not have uniformity in wall thickness, radius and/or shape. This non-uniformity of either the acetabular cup and/or cup insert allows for spherical center realignment to ensure concentricity between the acetabular cup and femoral head centers.

Figure 45:
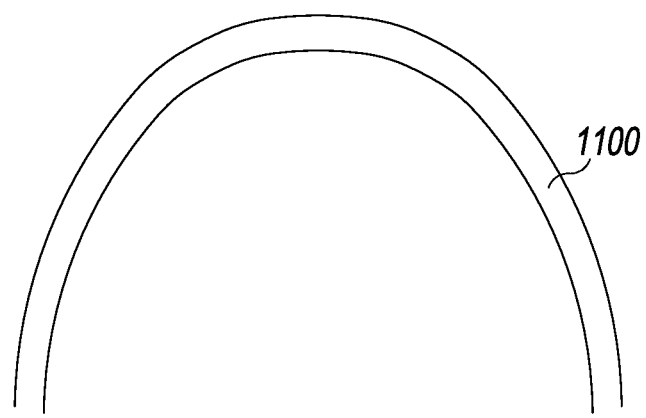
FIG. 45 is a vertical cross-section of a present day acetabular cup or cup insert having a uniform wall thickness.

Referring to FIG. 45, present day acetabular cups 1100 all have a uniform wall thickness.

Figure 46:
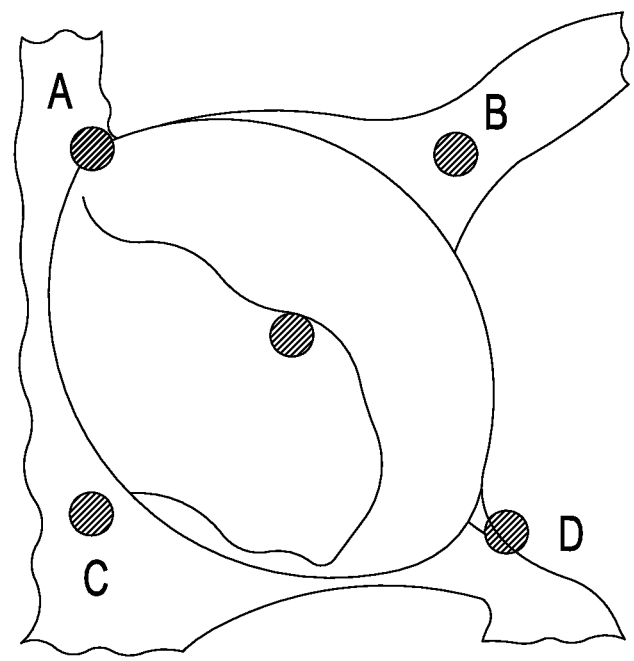
FIG. 46 is an overhead view of an acetabulum shown with various reference markings, A-E.
Figure 47:
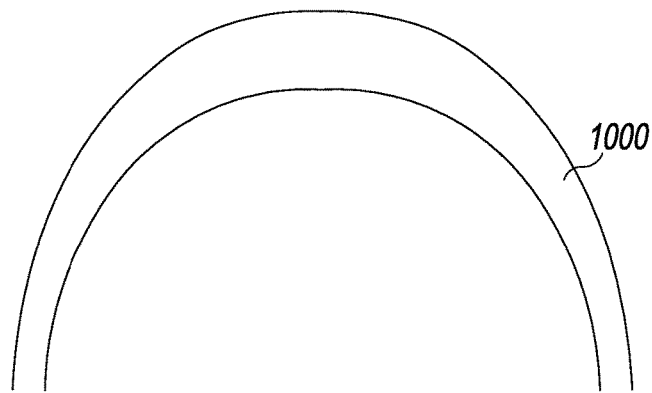
FIG. 47 is a vertical cross-section of an exemplary acetabular cup or cup insert that has a non-uniform wall thickness and shape.
Figure 48:
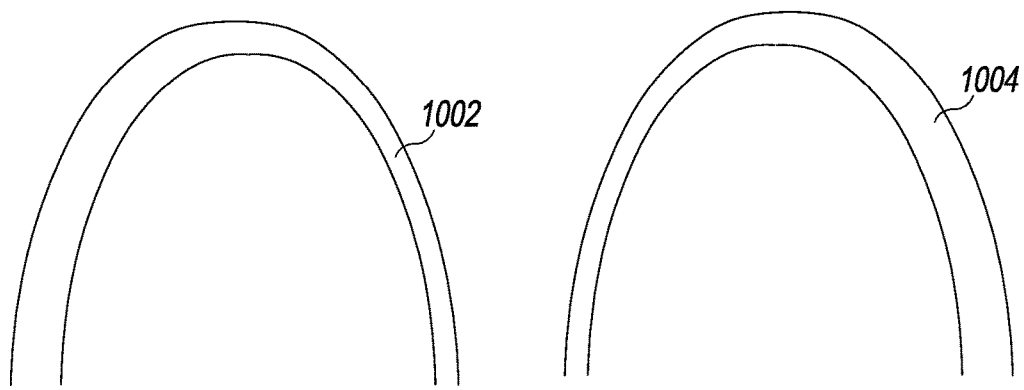
FIG. 48 are vertical cross-sections of exemplary acetabular cups or cup inserts that have a non-uniform wall thickness and shape.

Referencing FIGS. 46-48, if a surgeon reams out too much bone from one or more regions (e.g., points A-E in FIG. 46) of the acetabulum, then the surgeon can use a non-uniform acetabular cup and/or cup insert 1000, 1002, 1004. The non-uniform acetabular cup and/or cup insert 1000, 1002, 1004 has a non-uniform shape and wall thickness. The non-uniformity is used to shift the spherical center in various directions, such as, without limitation, proximal, distal, medial, and lateral. In this manner, the spherical center of the femoral component is aligned with the spherical center of the acetabular component.

Figure 49:
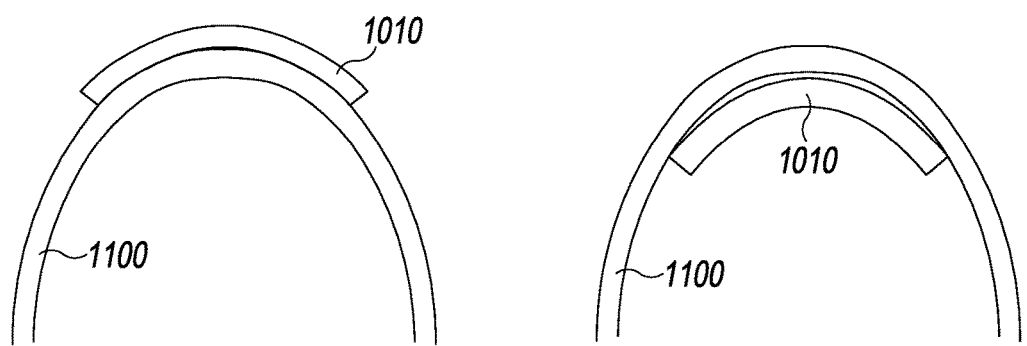
FIG. 49 are vertical cross-sections of present day acetabular cups or cup inserts shown with an attached insert to shift the spherical center of the acetabular component.

Referring to FIG. 49, the surgeon who reams out too much bone from the acetabulum may need a spacer 1010 that allows for the center of the acetabular cup or cup insert 1100 to be repositioned into alignment. This spacer 1010 may be mounted to the front side or back side of the acetabular cup and/or cup insert 1100. And the spacer 1010 may have a uniform of non-uniform wall thickness and shape. The spacer 1010 may be of any shape necessary to shift the spherical center in the proper direction. Exemplary materials for fabricating the spacer 1010 include, without limitation, titanium, cobalt chromium, high density polyethylene, and stainless steel.

Referencing FIGS. 46-49, if the surgeon reams away too much bone in the region between points A and B, B and C, C and D or A and D of FIG. 46, the surgeon may use either a non-uniform acetabular cup or cup insert 1000, 1002, 1004 or a spacer 1010 to shift the acetabular cup spherical center to the desired direction. It is also within the scope of the disclosure to use spacers 1010 with one or more of the non-uniform acetabular cup or cup insert 1000, 1002, 1004 to further shift the acetabular cup spherical center to the desired direction.

Though the above exemplary embodiments have all been discussed with respect to the hip joint, it is also within the scope of the disclosure to apply these same principles to other joints of the body including, without limitation, shoulder joint, elbow joint, and ankle joint. In other words, the shoulder joint, elbow joint, and ankle joint may be inserted wherever the foregoing describes a hip joint. And those skilled in the art should thus understand that the teachings and embodiments are equally applicable to shoulder joints, elbow joints, ankle joints, and hip joints.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A method of assembling a mobile bearing acetabular prosthetic component of a prosthetic hip joint, the method comprising:
   implanting an acetabular prosthetic cup including a rim surface, a concave curved inner surface extending inwardly from the rim surface to define an aperture in the acetabular prosthetic cup, and a first groove defined in the concave curved inner surface, the first groove extending along a first axis from a first opening defined in the rim surface to a second opening defined in the rim surface;
   mounting a first acetabular prosthetic cup insert to the acetabular prosthetic cup, the first acetabular cup insert including a convex curved outer surface, a concave curved inner surface positioned opposite the convex curved outer surface, a second groove defined in the concave curved inner surface of the first acetabular prosthetic cup insert that extends along a second axis, and a first elongated tab extending outwardly from the convex curved outer surface of first acetabular prosthetic cup insert, wherein mounting the first acetabular prosthetic cup insert to the acetabular prosthetic cup includes inserting the first elongated tab into the first opening in the first groove defined in the acetabular prosthetic cup to advance the first acetabular prosthetic cup insert into the aperture defined in the acetabular prosthetic cup and repositioning the first acetabular prosthetic cup insert with respect to the acetabular prosthetic cup such that the first acetabular prosthetic cup insert extends outwardly from the second opening beyond the rim surface of the acetabular prosthetic cup; and
   mounting a second acetabular prosthetic cup insert to the first acetabular prosthetic cup insert, the second acetabular prosthetic cup insert including a second elongated tab and a cavity sized to receive a prosthetic femoral ball, wherein mounting the second acetabular prosthetic cup insert to the first prosthetic acetabular prosthetic cup includes inserting the second elongated tab into the second groove defined in the first acetabular prosthetic cup insert and repositioning the second acetabular prosthetic cup insert with respect to the first acetabular prosthetic cup insert without disengaging the second acetabular prosthetic cup insert from the first acetabular prosthetic cup insert,
   wherein the first axis extends orthogonal to the second axis when the mobile bearing acetabular prosthetic component is assembled such that the first acetabular prosthetic cup insert is configured to tilt along the second axis and the second acetabular prosthetic cup insert is configured to tilt along the first axis orthogonal to the second axis.

2. The method of claim 1, wherein:
   repositioning the first acetabular prosthetic cup insert with respect to the acetabular prosthetic cup includes sliding the first acetabular prosthetic cup insert against the acetabular prosthetic cup along the first axis; and
   repositioning the second acetabular prosthetic cup insert with respect to the first acetabular prosthetic cup insert includes sliding the second acetabular prosthetic cup insert against the first acetabular prosthetic cup insert along the second axis.

3. The method of claim 1, wherein:
   repositioning the first acetabular prosthetic cup insert with respect to the acetabular prosthetic cup includes rotating the first acetabular prosthetic cup insert against the acetabular prosthetic cup along the first axis; and repositioning the second acetabular prosthetic cup insert with respect to the first acetabular prosthetic cup insert includes sliding the second acetabular prosthetic cup insert against the first acetabular prosthetic cup insert along the second axis.

4. The method of claim 1, wherein:

repositioning the first acetabular prosthetic cup insert with respect to the acetabular prosthetic cup includes sliding the first acetabular prosthetic cup insert against the acetabular prosthetic cup along the first axis; and repositioning the second acetabular prosthetic cup insert with respect to the first acetabular prosthetic cup insert includes rotating the second acetabular prosthetic cup insert against the first acetabular prosthetic cup insert along the second axis.

5. A method of assembling a mobile bearing acetabular prosthetic component of a prosthetic hip joint, the method comprising:

implanting an acetabular prosthetic cup including a rim surface, a concave curved inner surface extending inwardly from the rim surface to define an aperture in the acetabular prosthetic cup, and a first groove defined in the concave curved inner surface, the first groove extending along a first axis from a first opening defined in the rim surface to a second opening defined in the rim surface;

mounting a first acetabular prosthetic cup insert to the acetabular prosthetic cup, the first acetabular cup insert including a convex curved outer surface, a concave curved inner surface positioned opposite the convex curved outer surface, a second groove defined in the concave curved inner surface of the first acetabular prosthetic cup insert that extends along a second axis, and a first elongated tab extending outwardly from the convex curved outer surface of first acetabular prosthetic cup insert, wherein mounting the first acetabular prosthetic cup insert to the acetabular prosthetic cup includes inserting the first elongated tab into the first opening in the first groove defined in the acetabular prosthetic cup to advance the first acetabular prosthetic cup insert into the aperture defined in the acetabular prosthetic cup; and mounting a second acetabular prosthetic cup insert to the first acetabular prosthetic cup insert, the second acetabular prosthetic cup insert including a cavity sized to receive a prosthetic femoral ball.

6. The method of claim 5, wherein repositioning the first acetabular prosthetic cup insert with respect to the acetabular prosthetic cup includes sliding the first acetabular prosthetic cup insert against the acetabular prosthetic cup in the first axis.

7. The method of claim 5, wherein mounting the first acetabular prosthetic cup insert to the acetabular prosthetic cup includes repositioning the first acetabular prosthetic cup insert with respect to the acetabular prosthetic cup such that the elongated tab extends outwardly from the second opening beyond the rim surface of the acetabular prosthetic cup.

* * * * *